(12) United States Patent
Barlaam et al.

(10) Patent No.: US 8,530,470 B2
(45) Date of Patent: Sep. 10, 2013

(54) CHROMENONE DERIVATIVES

(75) Inventors: Bernard Christophe Barlaam, Reims, Cedex (FR); Sebastien Louis Degorce, Reims, Cedex (FR); Christine Marie Paul Lambert-Van Der Brempt, Reims, Cedex (FR); Jean-Jacques Marcel Lohmann, Reims, Cedex (FR); Patrick Ple, Reims, Cedex (FR)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 13/444,221

(22) Filed: Apr. 11, 2012

(65) Prior Publication Data
US 2012/0264731 A1    Oct. 18, 2012

(30) Foreign Application Priority Data
Apr. 13, 2011    (EP) .................................... 11290187

(51) Int. Cl.
*A61K 31/535*    (2006.01)
*C07D 413/14*    (2006.01)
(52) U.S. Cl.
USPC ...................................... 514/235.5; 544/141
(58) Field of Classification Search
USPC ...................................... 544/141; 514/235.5
See application file for complete search history.

(56) References Cited

U.S. PATENT DOCUMENTS
2011/0098271 A1    4/2011    Barlaam et al.

FOREIGN PATENT DOCUMENTS
| WO | 90/06921 A1 | 6/1990 |
|---|---|---|
| WO | 2004/016607 A1 | 2/2004 |
| WO | 2005/056014 A1 | 6/2005 |
| WO | 2008/064244 A2 | 5/2008 |
| WO | 2011/051704 A1 | 5/2011 |

OTHER PUBLICATIONS

Abid et al, "Vascular Endothelial Growth Factor Activates P13K/Akt/Forkhead Signaling in Endothelial Cells", Arterioscler Thromb Vasc Biol, 2004, pp. 294-300, vol. 24.
Blume-Jenson et al, "Oncogenic Kinase Signalling", Nature, 2001, pp. 355-365, vol. 411.
Bradshaw, "Cell Transformation: the role of oncogenes and growth factors", Mutagenesis, 1986, pp. 91-97, vol. 1 No. 2.
Chen et al, "Characterization of structurally distinct, isoform-selective phosphoinositide 3'-kinase inhibitors in combination with radiation in the treatment of gliobastoma", Mol Cancer Ther, 2008, pp. 841-850, vol. 7, No. 4.
Coussens et al, "Inflammation and Cancer", Nature, 2002, pp. 860-867, vol. 420.
Fan et al, "A dual PI3 kinase/mTOR inhibitor reveals emergent efficacy in glioma", Cancer Cell, 2006, pp. 341-349, vol. 9.

Foster et al, "The phosphoinositide (PI) 3-kinase family", Journal of Cell Science, 2003, pp. 3037-3040, vol. 116.
Harari et al, "Molecular mechanisms underlying ErbB/HER2 action in breast cancer", Oncogene, 2000, pp. 6102-6114, vol. 19.
Herman et al, "Phosphatidylinositol 3-kinase-δ inhibitor CAL-101 shows promising preclinical activity in chronic lymphocytic leukemia by antagonising intrinsic and extrinsic cellular survival signals", Blood, 2010, pp. 2078-2088, vol. 116, No. 12.
Hoellenriegel et al, "The phosphoinositide 3'-kinase delta inhibitor, CAL-101, inhibits B-cell receptor signaling and chemokine networks in chronic lymphocytic leukemia", Blood, 2011, pp. 3603-3612, vol. 118.
Ikeda et al, "PI3K/p11δ is a novel therapeutic target in multiple myeloma", Blood, 2010, pp. 1460-1468, vol. 116, No. 9.
Katso et al, "Cellular Function of Phosphoinositide 3-Kinases: Implications for Development, Immunity, Homeostasis, and Cancer", Annu Rev. Cell Dev. Biol, 2001, pp. 615-675, vol. 17.
Kauffmann-Zeh et al, "Suppression of c-Myc-induced apoptosis by Ras signalling through PI(3)K and PKB", Nature, 1997, pp. 544-548, vol. 385.
Koyasu, "The role of PI3K in immune cells", Nature Immunology, 2003, pp. 313-319, vol. 4, No. 4.
Lannutti et al, "CAL-101, a p110δ selective phosphatidylinositol-3-kinase inhibitor for the treatment of B-cell malignancies, inhibits P13K signaling and cellular viability", Blood, 2011, pp. 591-594, vol. 117, No. 2.
Larson et al, "New Approaches to Antitumor Therapy", Annual Reports in Medicinal Chemistry, 1989, Chapter 13, p. 121-128, vol. 24.
Ma et al, "PIK3CA as an oncogene in cervical cancer", Oncogene, 2000, pp. 2739-2744, vol. 19.
Nicholson et al, "The protein kinase B/Akt signalling pathway in human malignancy", Cellular Signalling, 2002, pp. 381-395, vol. 14.
Philp et al, "The Phosphatidylinositol 3'-kinase p85α Is an Oncogene in Human Ovarian and Colon Tumors", Cancer Research, 2001, pp. 7426-7429, vol. 61.
Prasad et al, "Role of Phosphoinositide 3-Kinase in Cardiac Function and Heart Failure", Trends in Cardiovascular Medicine, 2003, pp. 206-212, vol. 13, No. 5.

(Continued)

*Primary Examiner* — Rebecca Anderson

(57) ABSTRACT

The invention concerns chromenone compounds of Formula I;

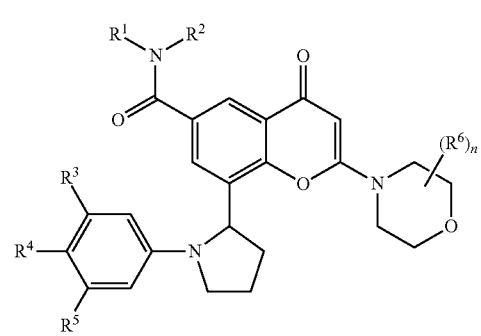

or pharmaceutically-acceptable salts thereof, wherein each of $R^1$, $R^2$, $R^3$, $R^4$, $R^5$, n and $R^6$ has any of the meanings defined hereinbefore in the description; processes for their preparation, pharmaceutical compositions containing them and their use in the manufacture of a medicament for use in the treatment of cell proliferative disorders.

17 Claims, 4 Drawing Sheets

(56) References Cited

OTHER PUBLICATIONS

Samuels et al, "High Frequency of Mutations of the PIK3CA Gene in Human Cancers", Science, 2004, p. 554, vol. 304.

Sawyer, "Cancer metastasis therapeutic targets and drug discovery: emerging small-molecule protein kinase inhibitors", Expert Opinion Investigational Drugs, 2004, pp. 1-19, vol. 13, No. 1.

Shayesteh et al, "PIK3CA is implicated as an oncogene in ovarian cancer", Nature Genetics, 1999, pp. 99-102, vol. 21.

Simpson et al, "PTEN: Life as a Tumor Suppressor", Experimental Cell Research, 2001, pp. 29-41, vol. 264.

Torbett et al, "A chemical screen in diverse breast cancer cell lines reveals genetic enhancers and suppressors of sensitivity to PI3K isoform-selective inhibition", Biochem J, 2008, pp. 97-110, vol. 415.

Vanheasebroeck et al, "Phosphoinositide 3-kinases: a conserved family of signal transducers", Trends in Biological Science, 1997, pp. 267-272, vol. 22.

Vara et al, "PI3K/Akt signalling pathway and cancer", Cancer Treatment Reviews, 2004, pp. 193-204, vol. 30.

Vivanco et al, "The Phosphatidylinositol 3-Kinase-AKT pathway in human cancer", Nature Reviews Cancer, 2002, pp. 489-501, vol. 2.

Wilks et al, "Protein Tyrosine Kinase Growth Factor Receptors and their ligands in development, differentiation and cancer", Advances in Cancer Research, 1993, pp. 43-71, vol. 60.

Wymann et al, "Phosphoinositide 3-kinase signalling—which way to target?", Trends in Pharmacological Sciences, 2003, pp. 366-376, vol. 24, No. 7.

Yarden, "Growth Factor Receptor Tyrosine Kinases", Ann. Rev. Biochem, 1988, pp. 443-478, vol. 57.

DSC Thermogram of Example 1.03b Form B

CHROMENONE DERIVATIVES

This application claims the benefit under 35 U.S.C. §119 (a)-(d) of Application No. 11290187.1 (EP) filed on 13 Apr. 2011.

The invention concerns certain novel chromenone compounds, or pharmaceutically-acceptable salts thereof, which possess anti-cancer activity and are accordingly useful in methods of treatment of the human or animal body. The invention also concerns processes for the manufacture of said chromenone compounds, pharmaceutical compositions containing them and their use in therapeutic methods, for example in the manufacture of medicaments for use in the prevention or treatment of cancers in a warm-blooded animal such as man, including use in the prevention or treatment of cancer.

The present invention also relates to chromenone compounds that are selective inhibitors of phosphoinositide (PI) 3-kinase β, and are, for example, useful for anti-tumour therapy. Further, the present invention also relates to the use of chromenone compounds of the invention that are selective inhibitors of phosphoinositide (PI) 3-kinase β, in anti-tumour therapy. Inhibitors of PI 3-kinase β may be effective in the treatment of tumours which are deficient in the gene PTEN (phosphatase and tensin homologue deleted on chromosome 10) and this relates to a further feature of the invention.

The present invention also relates to chromenone compounds that are selective inhibitors of phosphoinositide (PI) 3-kinase δ, and are, for example, useful for anti-tumour therapy; as well as chromenone compounds that are selective inhibitors of both PI 3-kinase β and PI 3-kinase δ. Such dual PI 3-kinase β/δ inhibitors are also useful in the treatment of tumours.

In the area of cancer it has in recent years been discovered that a cell may become cancerous by virtue of the transformation of a portion of its DNA into an oncogene, that is a gene which, on activation, leads to the formation of malignant tumour cells (Bradshaw, *Mutagenesis*, 1986, 1, 91). Several such oncogenes give rise to the production of peptides, which are receptors for growth factors. Activation of the growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al., *Ann. Reports in Med. Chem.*, 1989, Chpt. 13). The first group of tyrosine kinases to be identified arose from such viral oncogenes, for example pp60$^{v\text{-}Src}$ tyrosine kinase (otherwise known as v-Src), and the corresponding tyrosine kinases in normal cells, for example pp60$^{c\text{-}Src}$ tyrosine kinase (otherwise known as c-Src).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43-73) based on families of growth factors, which bind to different receptor tyrosine kinases. The classification includes Class I receptor tyrosine kinases comprising the EGF family of receptor tyrosine kinases such as the EGF, TGFα, Neu and erbB receptors.

It is also known that certain tyrosine kinases belong to the class of non-receptor tyrosine kinases which are located intracellularly and are involved in the transmission of biochemical signals such as those that influence tumour cell motility, dissemination and invasiveness and subsequently metastatic tumour growth. Various classes of non-receptor tyrosine kinases are known including the Src family such as the Src, Lyn, Fyn and Yes tyrosine kinases.

Further, it is also known that certain kinases belong to the class of serine/threonine kinases which are located intracellularly and downstream of tyrosine kinase activation and are involved in the transmission of biochemical signals such as those that influence tumour cell growth. Such serine/threonine signalling pathways include the Raf-MEK-ERK cascade and those downstream of PI 3-KINASE such as PDK-1, AKT and mTOR (Blume-Jensen and Hunter, *Nature*, 2001, 411, 355).

It is also known that certain other kinases belong to the class of lipid kinases, which are located intracellularly and are also involved in the transmission of biochemical signals such as those that influence tumour cell growth and invasiveness. Various classes of lipid kinases are known including the aforementioned PI 3-kinase family, which is alternatively known as the phosphatidylinositol-3-kinase family.

It is now well understood that deregulation of oncogenes and tumour-suppressor genes contributes to the formation of malignant tumours, for example by way of increased cell proliferation or increased cell survival. It is also now known that signalling pathways mediated by the PI 3-kinase family have a central role in a number of cell processes including proliferation and survival, and deregulation of these pathways is a causative factor a wide spectrum of human cancers and other diseases (Katso et al., *Annual Rev. Cell Dev. Biol.*, 2001, 17: 615-617 and Foster et al., *J. Cell Science*, 2003, 116: 3037-3040).

The PI 3-kinase family of lipid kinases is a group of enzymes that phosphorylate the 3-position of the inositol ring of phosphatidylinositol (PI). Three major groups of PI 3-kinase enzymes are known which are classified according to their physiological substrate specificity (Vanhaesebroeck et al., *Trends in Biol. Sci.*, 1997, 22, 267). Class III PI 3-kinase enzymes phosphorylate PI alone. In contrast, Class II PI 3-kinase enzymes phosphorylate both PI and PI 4-phosphate [abbreviated hereinafter to PI(4)P]. Class I PI 3-kinase enzymes phosphorylate PI, PI(4)P and PI 4,5-bisphosphate [abbreviated hereinafter to PI(4,5)P2], although only PI(4,5) P2 is believed to be the physiological cellular substrate. Phosphorylation of PI(4,5)P2 produces the lipid second messenger PI 3,4,5-triphosphate [abbreviated hereinafter to PI(3,4,5)P3]. More distantly related members of this superfamily are Class IV kinases such as mTOR and DNA-dependent kinase that phosphorylate serine/threonine residues within protein substrates. The most studied and understood of these lipid kinases are the Class I PI 3-kinase enzymes.

Class I PI 3-kinase is a heterodimer consisting of a p110 catalytic subunit and a regulatory subunit, and the family is further divided into Class Ia and Class Ib enzymes on the basis of regulatory partners and mechanism of regulation. Class Ia enzymes, include PI 3-kinase β, and consist of three distinct catalytic subunits (p110α, p110β and p110δ) that dimerise with five distinct regulatory subunits (p85α, p55α, p50α, p85β and p55γ), with all catalytic subunits being able to interact with all regulatory subunits to form a variety of heterodimers. Class Ia PI 3-kinase enzymes are generally activated in response to growth factor-stimulation of receptor tyrosine kinases, via interaction of the regulatory subunit SH2 domains with specific phospho-tyrosine residues of the activated receptor or adaptor proteins such as IRS-1. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzymes are activated in response to G-protein coupled receptor (GPCR) systems as well as by the mechanisms described above.

There is now considerable evidence indicating that Class Ia PI 3-kinase enzymes, which include PI 3-kinase β, contribute to tumourigenesis in a wide variety of human cancers, either directly or indirectly (Vivanco and Sawyers, *Nature Reviews Cancer,* 2002, 2, 489-501). For example, the p110α subunit is amplified in some tumours such as those of the ovary (Shayesteh et al., *Nature Genetics,* 1999, 21: 99-102) and cervix (Ma et al., *Oncogene,* 2000, 19: 2739-2744). Activating mutations within the catalytic site of p110α have been associated with various other tumours such as those of the colorectal region and of the breast and lung (Samuels et al., *Science,* 2004, 304, 554). Tumour-related mutations in p85α have also been identified in cancers such as those of the ovary and colon (Philp et al., *Cancer Research,* 2001, 61, 7426-7429). PI 3 kinase-δ plays a critical role in B-cell function and has been shown to be a mediator of survival signalling in a range of B-cell malignancies. This includes, but may not be limited to, chronic lymphocytic leukaemia (CLL), acute lymphoblastic leukaemia (ALL), follicular lymphoma, diffuse large B-cell lymphoma (DLBCL) and mantle cell lymphoma (Ikeda et al., *Blood,* 2010, 116, 1460-1468; Herman et al., *Blood,* 2010, 116, 2078-2088; Lannutti et al., *Blood,* 2011, 117, 591-594; Hoellenriegel et al., *Blood,* 2011, 118, 3603-3612). In addition to direct effects, it is believed that activation of Class Ia PI 3-kinase contributes to tumourigenic events that occur upstream in signalling pathways, for example by way of ligand-dependent or ligand-independent activation of receptor tyrosine kinases, GPCR systems or integrins (Vara et al., *Cancer Treatment Reviews,* 2004, 30, 193-204). Examples of such upstream signalling pathways include over-expression of the receptor tyrosine kinase Erb2 in a variety of tumours leading to activation of PI 3-kinase-mediated pathways (Harari et al., *Oncogene,* 2000, 19, 6102-6114) and over-expression of the oncogene Ras (Kauffmann-Zeh et al., *Nature,* 1997, 385, 544-548). In addition, Class Ia PI 3-kinases may contribute indirectly to tumourigenesis caused by various downstream signalling events. For example, loss of the effect of the PTEN tumour-suppressor phosphatase that catalyses conversion of PI(3,4,5)P3 back to PI(4,5)P2 is associated with a very broad range of tumours via deregulation of PI 3-kinase-mediated production of PI(3,4,5)P3 (Simpson and Parsons, *Exp. Cell Res.,* 2001, 264, 29-41). Furthermore, augmentation of the effects of other PI 3-kinase-mediated signalling events is believed to contribute to a variety of cancers, for example by activation of Akt (Nicholson and Anderson, *Cellular Signalling,* 2002, 14, 381-395).

In addition to a role in mediating proliferative and survival signalling in tumour cells, there is also good evidence that Class Ia PI 3-kinase enzymes will also contribute to tumourigenesis via its function in tumour-associated stromal cells. For example, PI 3-kinase signalling is known to play an important role in mediating angiogenic events in endothelial cells in response to pro-angiogenic factors such as VEGF (Abid et al., *Arterioscler. Thromb. Vasc. Biol.,* 2004, 24, 294-300). As Class I PI 3-kinase enzymes are also involved in motility and migration (Sawyer, *Expert Opinion Investig. Drugs,* 2004, 13, 1-19), PI 3-kinase inhibitors should provide therapeutic benefit via inhibition of tumour cell invasion and metastasis.

In addition, Class I PI 3-kinase enzymes play an important role in the regulation of immune cells with PI 3-kinase activity contributing to pro-tumourigenic effects of inflammatory cells (Coussens and Werb, *Nature,* 2002, 420, 860-867).

These findings suggest that pharmacological inhibitors of Class I PI 3-kinase enzymes should be of therapeutic value for treatment of the various forms of the disease of cancer comprising solid tumours such as carcinomas and sarcomas and the leukaemias and lymphoid malignancies. In particular, inhibitors of Class I PI 3-kinase enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, brain, head and neck, kidney, liver, gastrointestinal tissue, oesophagus, ovary, pancreas, skin, testes, thyroid, uterus, cervix and vulva, and of leukaemias (including ALL, CLL and CML [Chronic Myelogenous Leukaemia]), multiple myeloma and lymphomas (including non-Hodgkin's lymphomas such as diffuse large B-cell lymphoma [DLBCL], follicular lymphoma, and mantle cell lymphoma).

Generally, investigators have explored the physiological and pathological roles of the PI 3-kinase enzyme family using the aforementioned PI 3-kinase inhibitors LY294002 and wortmannin. Although use of those compounds may suggest a role for PI 3-kinase in a cellular event, they are not sufficiently selective within the PI 3-kinase family to allow dissection of the individual roles of the family members. For this reason, more potent and selective pharmaceutical PI 3-kinase inhibitors would be useful to allow a more complete understanding of PI 3-kinase function and to provide useful therapeutic agents.

In addition to tumourigenesis, there is evidence that Class I PI 3-kinase enzymes play a role in other diseases (Wymann et al., *Trends in Pharmacological Science,* 2003, 24, 366-s 376). Both Class Ia PI 3-kinase enzymes and the single Class Ib enzyme have important roles in cells of the immune system (Koyasu, *Nature Immunology,* 2003, 4, 313-319) and thus they are therapeutic targets for inflammatory and allergic indications. Inhibition of PI 3-kinase is also, as described earlier, useful to treat cardiovascular disease via anti-inflammatory effects or directly by affecting cardiac myocytes (Prasad et al., *Trends in Cardiovascular Medicine,* 2003, 13, 206-212) Inhibition of PI 3-kinase is also useful to treat thrombosis. WO2004016607 provides a method of disrupting platelet aggregation and adhesion occurring under high shear conditions, and a method for inhibiting platelet activation induced by shear, where both methods comprise the administration of a selective PI 3-kinase β inhibitor. WO2004016607 also provides an antithrombotic method comprising administering an effective amount of a selective PI 3-kinase β inhibitor. According to the method, specific inhibition of thrombosis can be obtained without affecting normal haemostasis by targeting PI 3-kinase β that is important for shear-induced platelet activation. Said antithrombotic method therefore does not involve side effects caused by disruption of normal haemostasis, such as extending of bleeding time. Thus inhibitors of Class I PI 3-kinase enzymes, including inhibitors of PI 3-kinase β, are expected to be of value in the prevention and treatment of a wide variety of diseases in addition to cancer.

The compounds, i.e. the chromenone compounds, of the invention have now surprisingly been found to possess potent anti-tumour activity, being useful in inhibiting the uncontrolled cellular proliferation which arises from malignant disease. Without wishing to imply that the compounds disclosed in the present invention possess pharmacological activity only by virtue of an effect on a single biological process, it is believed that the compounds provide an anti-tumour effect by way of inhibition of Class I PI 3-kinase enzymes, particularly by way of inhibition of the Class Ia PI 3-kinase enzymes and/or the Class Ib PI 3-kinase enzyme, more particularly by way of inhibition of the Class Ia PI 3-kinase enzymes, which include inhibition of PI 3-kinase β.

The compounds of the present invention are also useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, benign prostatic hypertrophy (BPH), hypersensitivity reactions of the skin, blood vessel diseases (for example atherosclerosis and restenosis), allergic asthma, insulin-dependent diabetes, diabetic retinopathy and diabetic nephropathy.

Generally, the compounds of the present invention possess potent inhibitory activity against Class I PI 3-kinase enzymes, particularly against Class Ia PI 3-kinase enzymes, including against of PI 3-kinase β, whilst possessing less potent inhibitory activity against tyrosine kinase enzymes such as the receptor tyrosine kinases, for example EGF receptor tyrosine kinase and/or VEGF receptor tyrosine kinase, or against non-receptor tyrosine kinases such as Src. Furthermore, certain compounds of the present invention possess substantially better potency against Class I PI 3-kinase enzymes, particularly against Class Ia PI 3-kinase enzymes, including against of PI 3-kinase β, than against EGF receptor tyrosine kinase or VEGF receptor tyrosine kinase or Src non-receptor tyrosine kinase. Such compounds possess sufficient potency against Class I PI 3-kinase enzymes that they may be used in an amount sufficient to inhibit Class I PI 3-kinase enzymes, particularly to inhibit Class Ia PI 3-kinase enzymes, including PI 3-kinase β, whilst demonstrating little activity against EGF receptor tyrosine kinase or VEGF receptor tyrosine kinase or Src non-receptor tyrosine kinase.

In addition, particular compounds of the invention demonstrate potent inhibitory activity against both PI 3-kinase β and PI 3-kinase δ, whilst possessing less potent inhibitory activity against tyrosine kinase enzymes such as the receptor tyrosine kinases, for example EGF receptor tyrosine kinase and/or VEGF receptor tyrosine kinase, or against non-receptor tyrosine kinases such as Src. Furthermore, certain compounds of the present invention possess substantially better potency against both PI 3-kinase β and PI 3-kinase δ than against EGF receptor tyrosine kinase or VEGF receptor tyrosine kinase or Src non-receptor tyrosine kinase. Such compounds possess sufficient potency against both PI 3-kinase β and PI 3-kinase δ that they may be used in an amount sufficient to inhibit PI 3-kinase β and PI 3-kinase δ, whilst demonstrating little activity against EGF receptor tyrosine kinase or VEGF receptor tyrosine kinase or Src non-receptor tyrosine kinase.

According to one aspect of the invention there is provided a chromenone derivative of the Formula I:

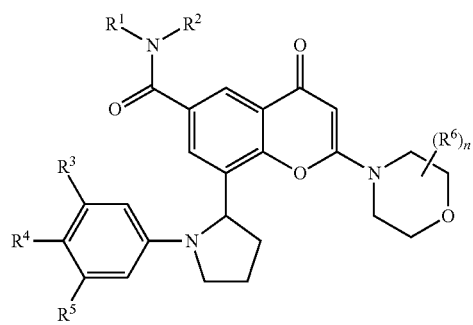

in which:
$R^1$ is (1-4C)alkyl optionally substituted by hydroxy;
$R^2$ is H or (1-4C)alkyl; or
$R^1$ and $R^2$ together form a 3 to 8 membered nitrogen containing heterocyclyl ring system, which optionally contains 1 or 2 further heteroatoms selected from oxygen, nitrogen and sulphur, wherein a ring sulphur atom is optionally oxidised to form the S-oxide(s), said ring being optionally substituted by hydroxy;
$R^3$ and $R^5$ are independently selected from H, halogeno, (1-3C)alkoxy and cyano;
$R^4$ is H or fluoro;
n is 0 or 1, and when n is 1, the $R^6$ group is methyl; or a pharmaceutically-acceptable salt thereof.

In this specification the generic term "(1-4C)alkyl" includes both straight-chain and branched-chain alkyl groups such as propyl, isopropyl and tert-butyl, and also (3-4C)cycloalkyl groups such as cyclopropyl and cyclobutyl, and also groups such as cyclopropylmethyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopropyl" are specific for that 3-membered ring only.

A person skilled in the art will appreciate that the terms "(1-4C)alkyl" and "(1-3C)alkyl" that are used herein refer to any of the alkyl groups defined above that possesses 1 to 4 and 1 to 3 carbon atoms respectively. The same convention applies to other terms used herein, such as, for example "(1-3C)alkoxy", "(1-10C)alkoxycarbonyl" and "(1-10C)alkanoyl".

It is to be understood that, insofar as certain of the compounds of Formula I defined above may exist in optically active or racemic forms by virtue of one or more asymmetric carbon atoms, the invention includes in its definition any such optically active or racemic form which possesses phosphoinositide (PI) 3-kinase inhibitory activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques.

A particular enantiomer of the compounds described herein may be more active that other enantiomers of the compound. For example, the (+) enantiomer of the title compound of Example 1.03 (i.e. the compound of Example 1.03a, where (+) signifies the optical rotation measured using the conditions described in Example 1.03a) is the enantiomer having the weaker activity. For the avoidance of doubt, the chiral centre in question is the carbon atom at the 2-position of the central pyrrolidine ring that is linked to the chromenone bicyclic ring.

Accordingly, in a further aspect of the invention, there is provided a chromenone derivative of the Formula I, or a pharmaceutically-acceptable salt thereof, wherein the chiral centre at the 2-position of the central pyrrolidine ring that is linked to the chromenone bicyclic ring is in the (R)-stereochemical configuration. In a further aspect of the invention, there is provided a chromenone derivative of the Formula I, or a pharmaceutically-acceptable salt thereof, wherein the chiral centre at the 2-position of the central pyrrolidine ring that is linked to the chromenone bicyclic ring is in the (S)-stereochemical configuration.

According to a further aspect of the invention there is provided a chromenone derivative of the Formula I, or a pharmaceutically-acceptable salt thereof, which is a single enantiomer being in an enantiomeric excess (% ee) of ≧95, ≧98% or ≧99%. In one embodiment of this aspect of the invention, the chiral centre at the 2-position of the central pyrrolidine ring that is linked to the chromenone bicyclic ring is in the (R)-stereochemical configuration. In a further embodiment of this aspect of the invention, the chiral centre at the 2-position of the central pyrrolidine ring that is linked to the chromenone bicyclic ring is in the (S)-stereochemical configuration.

According to a further aspect of the invention there is provided a pharmaceutical composition, which comprises a chromenone derivative of the Formula I, which is a single enantiomer being in an enantiomeric excess (% ee) of ≧95, ≧98% or ≧99% or a pharmaceutically-acceptable salt thereof, in association with a pharmaceutically-acceptable diluent or carrier. Conveniently, the single enantiomer is present in an enantiomeric excess (% ee) of ≧99%. In one embodiment of this aspect of the invention, the chiral centre at the 2-position of the central pyrrolidine ring that is linked to the chromenone bicyclic ring is in the (R)-stereochemical configuration. In a further embodiment of this aspect of the invention, the chiral centre at the 2-position of the central pyrrolidine ring that is linked to the chromenone bicyclic ring is in the (S)-stereochemical configuration.

Some compounds of Formula I may exhibit polymorphism. It is to be understood that the present invention encompasses any polymorphic form, or mixtures thereof, which form possesses properties useful in the inhibition of phosphoinositide (PI) 3-kinase activity, it being well known in the art how to determine efficacy of a polymorphic form for the inhibition of phosphoinositide (PI) 3-kinase activity by the standard tests described hereinafter.

It is generally known that crystalline materials may be analysed using conventional techniques such as X-Ray Powder Diffraction (hereinafter XRPD) analysis, Differential Scanning calorimetry (hereinafter DSC), Thermal Gravimetric Analysis (hereinafter TGA), Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

As an example, the compound of Example 1.03b exhibits polymorphism and three crystalline forms A, B and C have been identified. Particular crystalline forms may exhibit advantageous properties such as improved stability which makes them particularly suitable for pharmaceutical development.

Accordingly, a further aspect of the invention is Form A of 8-[(2R)-1-(3,5-difluorophenyl)pyrrolidin-2-yl]-6-(morpholine-4-carbonyl)-2-morpholino-chromen-4-one.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least one specific peak at about 2-theta=4.8°.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least one specific peak at about 2-theta=8.1°.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least two specific peaks at about 2-theta=4.8° and 8.1°.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern with specific peaks at about 2-theta=4.8, 6.4, 8.1, 9.6, 15.8, 19.5, 20.3, 22.7, 23.4, 25.9°.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern substantially the same as the X-ray powder diffraction pattern shown in FIG. 1.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least one specific peak at about 2-theta=4.8° plus or minus 0.5° 2-theta.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least one specific peak at about 2-theta=8.1° plus or minus 0.5° 2-theta.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least two specific peaks at about 2-theta=4.8° and 8.1° wherein said values may be plus or minus 0.5° 2-theta.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern with specific peaks at about 2-theta=4.8, 6.4, 8.1, 9.6, 15.8, 19.5, 20.3, 22.7, 23.4, 25.9° wherein said values may be plus or minus 0.5° 2-theta.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least one specific peak at 2-theta=4.8°.

According to a further aspect of the present invention, there is provided a crystalline form, Form A of 8-[(2R)-1-(3,5-difluorophenyl)pyrrolidin-2-yl]-6-(morpholine-4-carbonyl)-

2-morpholino-chromen-4-one, which has an X-ray powder diffraction pattern with at least one specific peak at 2-theta=8.1°.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least two specific peaks at 2-theta=4.8° and 8.1°.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern with specific peaks at 2-theta=4.8, 6.4, 8.1, 9.6, 15.8, 19.5, 20.3, 22.7, 23.4, 25.9°.

According to a further aspect of the present invention, there is provided a crystalline form, Form A of 8-[(2R)-1-(3,5-difluorophenyl)pyrrolidin-2-yl]-6-(morpholine-4-carbonyl)-2-morpholino-chromen-4-one, which has an X-ray powder diffraction pattern as shown in FIG. 1.

A further aspect of the invention is Form B of 8-[(2R)-1-(3,5-difluorophenyl)pyrrolidin-2-yl]-6-(morpholine-4-carbonyl)-2-morpholino-chromen-4-one.

According to a further aspect of the present invention, there is provided a crystalline form, Form B of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least one specific peak at about 2-theta=11.1°.

According to a further aspect of the present invention, there is provided a crystalline form, Form B of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least two specific peaks at about 2-theta=6.9° and 11.1°.

According to a further aspect of the present invention, there is provided a crystalline form, Form B of 8-[(2R)-1-(3,5-difluorophenyl)pyrrolidin-2-yl]-6-(morpholine-4-carbonyl)-2-morpholino-chromen-4-one, which has an X-ray powder diffraction pattern with specific peaks at about 2-theta=6.9, 9.4, 9.8, 11.1, 12.7, 13.1, 13.7, 17.8, 18.7, 19.7°.

According to a further aspect of the present invention, there is provided a crystalline form, Form B of 8-[(2R)-1-(3,5-difluorophenyl)pyrrolidin-2-yl]-6-(morpholine-4-carbonyl)-2-morpholino-chromen-4-one, which has an X-ray powder diffraction pattern substantially the same as the X-ray powder diffraction pattern shown in FIG. 2.

According to a further aspect of the present invention, there is provided a crystalline form, Form B of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least one specific peak at about 2-theta=11.1° plus or minus 0.5° 2-theta.

According to a further aspect of the present invention, there is provided a crystalline form, Form B of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least two specific peaks at about 2-theta=6.9 and 11.1° wherein said values may be plus or minus 0.5° 2-theta.

According to a further aspect of the present invention, there is provided a crystalline form, Form B of 8-[(2R)-1-(3,5-difluorophenyl)pyrrolidin-2-yl]-6-(morpholine-4-carbonyl)-2-morpholino-chromen-4-one, which has an X-ray powder diffraction pattern with specific peaks at about 2-theta=6.9, 9.4, 9.8, 11.1, 12.7, 13.1, 13.7, 17.8, 18.7, 19.7° wherein said values may be plus or minus 0.5° 2-theta.

According to a further aspect of the present invention, there is provided a crystalline form, Form B of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least one specific peak at 2-theta=11.1°.

According to a further aspect of the present invention, there is provided a crystalline form, Form B of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least two specific peaks at 2-theta=6.9° and 11.1°.

According to a further aspect of the present invention, there is provided a crystalline form, Form B of 8-[(2R)-1-(3,5-difluorophenyl)pyrrolidin-2-yl]-6-(morpholine-4-carbonyl)-2-morpholino-chromen-4-one, which has an X-ray powder diffraction pattern with specific peaks at 2-theta=6.9, 9.4, 9.8, 11.1, 12.7, 13.1, 13.7, 17.8, 18.7, 19.7°.

According to a further aspect of the present invention, there is provided a crystalline form, Form B of 8-[(2R)-1-(3,5-difluorophenyl)pyrrolidin-2-yl]-6-(morpholine-4-carbonyl)-2-morpholino-chromen-4-one, which has an X-ray powder diffraction pattern as shown in FIG. 2.

A further aspect of the invention is Form C of 8-[(2R)-1-(3,5-difluorophenyl)pyrrolidin-2-yl]-6-(morpholine-4-carbonyl)-2-morpholino-chromen-4-one.

According to a further aspect of the present invention, there is provided a crystalline form, Form C of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least two specific peaks at about 2-theta=5.9 and 12.2°.

According to a further aspect of the present invention, there is provided a crystalline form, Form C of 8-[(2R)-1-(3,5-difluorophenyl)pyrrolidin-2-yl]-6-(morpholine-4-carbonyl)-2-morpholino-chromen-4-one, which has an X-ray powder diffraction pattern with specific peaks at about 2-theta=5.9, 12.2, 11.8, 13.5, 15.2, 15.4, 17.1°.

According to a further aspect of the present invention, there is provided a crystalline form, Form C of 8-[(2R)-1-(3,5-difluorophenyl)pyrrolidin-2-yl]-6-(morpholine-4-carbonyl)-2-morpholino-chromen-4-one, which has an X-ray powder diffraction pattern substantially the same as the X-ray powder diffraction pattern shown in FIG. 4.

According to a further aspect of the present invention, there is provided a crystalline form, Form C of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least two specific peaks at about 2-theta=5.9 and 12.2° wherein said values may be plus or minus 0.5° 2-theta.

According to a further aspect of the present invention, there is provided a crystalline form, Form C of 8-[(2R)-1-(3,5-difluorophenyl)pyrrolidin-2-yl]-6-(morpholine-4-carbonyl)-2-morpholino-chromen-4-one, which has an X-ray powder diffraction pattern with specific peaks at about 2-theta=5.9, 12.2, 11.8, 13.5, 15.2, 15.4, 17.1° wherein said values may be plus or minus 0.5° 2-theta.

According to a further aspect of the present invention, there is provided a crystalline form, Form C of 8-[(2R)-1-(3,5-difluorophenyl)pyrrolidin-2-yl]-6-(morpholine-4-carbonyl)-2-morpholino-chromen-4-one, which has an X-ray powder diffraction pattern with at least two specific peaks at 2-theta=5.9° and 12.2°.

According to a further aspect of the present invention, there is provided a crystalline form, Form C of 8-[(2R)-1-(3,5-difluorophenyl)pyrrolidin-2-yl]-6-(morpholine-4-carbonyl)-

2-morpholino-chromen-4-one, which has an X-ray powder diffraction pattern with specific peaks at 2-theta=5.9, 12.2, 11.8, 13.5, 15.2, 15.4, 17.1°.

According to a further aspect of the present invention, there is provided a crystalline form, Form C of 8-[(2R)-1-(3,5-difluorophenyl)pyrrolidin-2-yl]-6-(morpholine-4-carbonyl)-2-morpholino-chromen-4-one, which has an X-ray powder diffraction pattern as shown in FIG. 4.

It will be understood that 2-theta values of the X-ray powder diffraction patterns may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the crystalline Forms of the present invention described above, unless otherwise stated, are not limited to the crystals that provide X-ray powder diffraction patterns identical to the X-ray powder diffraction pattern shown in FIGS. 1, 2 and 4 and any crystals providing X-ray powder diffraction patterns substantially the same as those shown in FIGS. 1, 2 and 4 fall within the scope of the present invention. A person skilled in the art of X-ray powder diffraction is able to judge the substantial identity of X-ray powder diffraction patterns.

Persons skilled in the art of X-ray powder diffraction will also realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values (see Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.5° 2-theta, and such degree of a measurement error should be taken into account when considering the X-ray powder diffraction data. Furthermore, it should be understood that intensities might fluctuate depending on experimental conditions and sample preparation (preferred orientation).

Particular compounds of the invention are each of the Examples and pharmaceutically-acceptable salt(s) thereof, each of which provides a further independent aspect of the invention.

According to a further aspect of the invention there is provided a chromenone derivative of the Formula I, which is obtainable by following any of the Examples as disclosed herein.

A further feature of the invention is any of the scopes defined herein with the proviso that specific Examples, such as Example 1.00, 1.01, 1.03, 1.03b, 1.05, 1.06, 1.07, 1.08, 2.00, 3.00, 3.02, 3.03 etc. are individually disclaimed.

A yet further feature of the invention is any of the scopes defined herein with the proviso that one specific Example, such as Example 1.00, 1.01, 1.03, 1.03b, 1.05, 1.06, 1.07, 1.08, 2.00, 3.00, 3.02, 3.03 etc. is individually disclaimed.

Accordingly, in one further aspect of the invention there is provided a chromenone derivative of the Formula I:

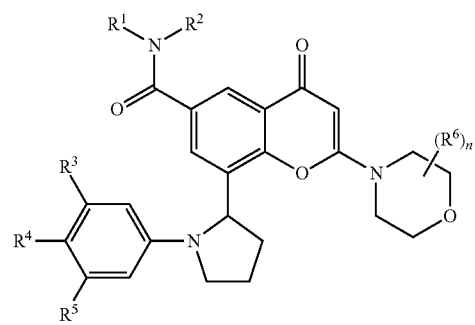

in which:

$R^1$ is (1-4C)alkyl optionally substituted by hydroxy;

$R^2$ is H or (1-4C)alkyl; or $R^1$ and $R^2$ together form a 3 to 8 membered nitrogen containing heterocyclyl ring system, which optionally contains 1 or 2 further heteroatoms selected from oxygen, nitrogen and sulphur, wherein a ring sulphur atom is optionally oxidised to form the S-oxide(s), said ring being optionally substituted by hydroxy;

$R^3$ and $R^5$ are independently selected from H, halogeno, (1-3C)alkoxy and cyano;

$R^4$ is H or fluoro;

n is 0 or 1, and when n is 1, the $R^6$ group is methyl; or a pharmaceutically-acceptable salt thereof; with the proviso that the compound of the Formula I is other than 8-[(2R)-1-(3,5-difluorophenyl)pyrrolidin-2-yl]-6-(morpholine-4-carbonyl)-2-morpholino-chromen-4-one.

It is to be understood that certain compounds of Formula I defined above may exhibit the phenomenon of tautomerism. It is to be understood that the present invention includes in its definition any such tautomeric form, or a mixture thereof, which possesses phosphoinositide (PI) 3-kinase inhibitory activity and is not to be limited merely to any one tautomeric form utilised within the formulae drawings or named in the Examples. In general, just one of any such tautomeric forms is named in the Examples that follow hereinafter or is presented in any relevant formulae drawings that follow hereinafter.

Suitable values for the generic radicals referred to above include those set out below.

A suitable value for the 3 to 8 membered nitrogen containing heterocyclyl ring system formed by the $R^1$ and $R^2$ groups of Formula I is, for example, a nitrogen containing non-aromatic saturated or partially saturated 3 to 8 membered ring, which optionally contains 1 or 2 further heteroatoms selected from oxygen, nitrogen and sulphur, wherein a ring sulphur atom is optionally oxidised to form the S-oxide(s). Suitable examples include azepanyl, oxazepanyl, aziridinyl, azetidinyl, pyrrolinyl, pyrrolidinyl, imidazolinyl, imidazolidinyl, pyrazolinyl, pyrazolidinyl, morpholinyl, thiomorpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl. In a particular group of compounds, particular examples of the heterocyclyl ring include azetidinyl, morpholinyl, 1-oxotetrahydro-1,4-thiazinyl and piperidinyl, and especially, azetidin-1-yl, morpholin-4-yl, 1-oxotetrahydro-1,4-thiazin-4-yl, and piperidin-1-yl.

Suitable values for any of the 'R' groups ($R^1$ to $R^6$), include, for example:— for halogeno fluoro, chloro, bromo and iodo;
for (1-4C)alkyl: methyl, ethyl, propyl, isopropyl, tert-butyl, cyclopropyl, and cyclobutyl;
for (1-3C)alkoxy: methoxy, ethoxy, propoxy and isopropoxy.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic or citric acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine. A further suitable pharmaceutically-acceptable salt of a compound of the Formula I is, for example, a salt formed within the human or animal body after administration of a compound of the Formula I.

It is further to be understood that a suitable pharmaceutically-acceptable solvate of a compound of the Formula I also forms an aspect of the present invention. A suitable pharmaceutically-acceptable solvate is, for example, a hydrate such as a hemi-hydrate, a mono-hydrate, a di-hydrate or a tri-hydrate or an alternative quantity thereof.

It is further to be understood that a suitable pharmaceutically-acceptable pro-drug of a compound of the Formula I also forms an aspect of the present invention. Accordingly, the compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a hydroxy group in a compound of the Formula I and in vivo cleavable amide derivatives that may be formed at an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically-acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula I that possesses a hydroxy group is, for example, an in vivo cleavable ester or ether thereof. An in vivo cleavable ester or ether of a compound of the Formula I containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include (1-10C)alkanoyl groups such as acetyl, benzoyl, phenylacetyl and substituted benzoyl and phenylacetyl groups, (1-10C)alkoxycarbonyl groups such as ethoxycarbonyl, N,N-[di-(1-4C)alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the Formula I that possesses an amino group is, for example, an in vivo cleavable amide derivative thereof. Suitable pharmaceutically-acceptable amides from an amino group include, for example an amide formed with (1-10C) alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl.

The in vivo effects of a compound of the Formula I may be exerted in part by one or more metabolites that are formed within the human or animal body after administration of a compound of the Formula I. As stated hereinbefore, the in vivo effects of a compound of the Formula I may also be exerted by way of metabolism of a precursor compound (a pro-drug).

For the avoidance of doubt it is to be understood that where in this specification a group is qualified by 'hereinbefore defined' or 'defined hereinbefore' the said group encompasses the first occurring and broadest definition as well as each and all of the particular definitions for that group.

Particular novel compounds of the invention include, for example, chromenone compounds of the Formula I, or pharmaceutically-acceptable salts thereof, wherein, unless otherwise stated, each of $R^1$, $R^2$, $R^3$, $R^4$, $R^5$, n and $R^6$ has any of the meanings defined hereinbefore or in paragraphs (a) to (u) hereinafter:

(a) $R^1$ is (1-4C)alkyl;
(b) $R^1$ is methyl, ethyl or 2-hydroxyethyl;

(c) $R^1$ is methyl or ethyl;
(d) $R^1$ is methyl;
(e) $R^2$ is (1-4C)alkyl;
(f) $R^2$ is methyl or ethyl;
(g) $R^2$ is methyl;
(h) $R^1$ and $R^2$ together form a 4 to 6 membered nitrogen containing heterocyclyl ring system, which optionally contains 1 further heteroatom selected from oxygen, nitrogen and sulphur, wherein a ring sulphur atom is optionally oxidised to form the S-oxide(s), said ring being optionally substituted by hydroxy;
(i) $R^1$ and $R^2$ together form a nitrogen containing heterocyclyl ring system, selected from azetidinyl, morpholinyl, 1-oxotetrahydro-1,4-thiazinyl and piperidinyl, said ring being optionally substituted by hydroxy;
(j) $R^1$ and $R^2$ together form a nitrogen containing heterocyclyl ring system, selected from azetidin-1-yl, morpholin-4-yl, 1-oxotetrahydro-1,4-thiazin-4-yl, and piperidin-1-yl, said ring being optionally substituted by hydroxy;
(k) $R^1$ and $R^2$ together form a nitrogen containing heterocyclyl ring system, selected from azetidin-1-yl or morpholin-4-yl;
(l) $R^3$ and $R^5$ are independently selected from H, fluoro, methoxy and cyano;
(m) $R^3$ and $R^5$ are independently selected from H and fluoro;
(n) $R^3$ and $R^5$ are H;
(o) $R^3$ and $R^5$ are fluoro;
(p) $R^4$ is H;
(q) $R^3$ and $R^4$ are H and $R^5$ is fluoro;
(r) $R^3$ and $R^5$ are fluoro and $R^4$ is H;
(s) n is 0;
(t) n is 1; and
(u) n is 1 and $R^6$ is a methyl group located in the 2-position of the morpholine ring.
(v) $R^1$ and $R^2$ together form a nitrogen containing heterocyclyl ring system, which ring is morpholin-4-yl;

A particular group of compounds of the invention are chromenone compounds of Formula I above wherein:—
$R^1$ is (1-4C)alkyl optionally substituted by hydroxy;
$R^2$ is (1-4C)alkyl; or
$R^1$ and $R^2$ together form a 4 to 6 membered nitrogen containing heterocyclyl ring system, which optionally contains 1 further heteroatom selected from oxygen, nitrogen and sulphur, wherein a ring sulphur atom is optionally oxidised to form the S-oxide(s), said ring being optionally substituted by hydroxy;
$R^3$ and $R^5$ are independently selected from H or halogeno and $R^4$ is H;
n is 0 or 1, and when n is 1, the $R^6$ group is methyl; or a pharmaceutically-acceptable salt thereof.

A further particular group of compounds of the invention are chromenone compounds of Formula I above wherein:—
$R^1$ is (1-4C)alkyl optionally substituted by hydroxy;
$R^2$ is (1-4C)alkyl; or
$R^1$ and $R^2$ together form a nitrogen containing heterocyclyl ring system, selected from azetidinyl, morpholinyl, 1-oxotetrahydro-1,4-thiazinyl and piperidinyl, said ring being optionally substituted by hydroxy;
$R^3$ and $R^5$ are independently selected from H or halogeno and $R^4$ is H;
n is 0 or 1, and when n is 1, the $R^6$ group is methyl; or a pharmaceutically-acceptable salt thereof.

A further particular group of compounds of the invention are chromenone compounds of Formula I above wherein:—
$R^1$ is methyl, ethyl or 2-hydroxyethyl;
$R^2$ is methyl or ethyl; or
$R^1$ and $R^2$ together form a nitrogen containing heterocyclyl ring system, selected from azetidinyl, morpholinyl, 1-oxotetrahydro-1,4-thiazinyl and piperidinyl, said ring being optionally substituted by hydroxy;
$R^3$ and $R^5$ are independently selected from H or halogeno and $R^4$ is H;
n is 0 or 1, and when n is 1, the $R^6$ group is methyl; or a pharmaceutically-acceptable salt thereof.

A further particular group of compounds of the invention are chromenone compounds of Formula I above wherein:—
$R^1$ is methyl or ethyl;
$R^2$ is methyl or ethyl; or
$R^1$ and $R^2$ together form a nitrogen containing heterocyclyl ring system, selected from azetidin-1-yl, morpholin-4-yl, 1-oxotetrahydro-1,4-thiazin-4-yl, and piperidin-1-yl, said ring being optionally substituted by hydroxy;
$R^3$ and $R^5$ are independently selected from H or fluoro and $R^4$ is H;
n is 0 or 1, and when n is 1, the $R^6$ group is methyl; or a pharmaceutically-acceptable salt thereof.

A further particular group of compounds of the invention are chromenone compounds of Formula I above or pharmaceutically-acceptable salt(s) thereof, wherein:—$R^1$ and $R^2$ are suitably as defined in any of paragraphs (a) to (k) above, particularly as defined in paragraph (d), (g) or (i) to (k) above; $R^3$, $R^4$ and $R^5$ are suitably as defined in any one of paragraphs (l) to (r) above and is particularly as defined in paragraph (r) or (s) above; and n and $R^6$ are suitably as defined in any one of paragraphs (s) to (u) above.

A further particular group of compounds of the invention are chromenone compounds of Formula I above or pharmaceutically-acceptable salt(s) thereof, wherein:—$R^1$ and $R^2$ are suitably as defined in any of paragraphs (a) to (k) above, or (v) above, particularly as defined in paragraph (d), (g), (v) or (i) to (k) above, and more particularly in paragraph (v) above; $R^3$, $R^4$ and $R^5$ are suitably as defined in any one of paragraphs (l) to (r) above and is particularly as defined in paragraph (r) or (s) above; and n and $R^6$ are suitably as defined in any one of paragraphs (s) to (u) above.

A further particular group of compounds of the invention are chromenone compounds of Formula I above wherein:—
$R^1$ is methyl or 2-hydroxyethyl;
$R^2$ is methyl; or
$R^1$ and $R^2$ together form a nitrogen containing heterocyclyl ring system, selected from azetidin-1-yl, morpholin-4-yl, 1-oxotetrahydro-1,4-thiazin-4-yl, piperidin-1-yl and 4-hydroxypiperidin-1-yl;
$R^3$ and $R^5$ are independently selected from H, fluoro, methoxy and cyano;
$R^4$ is H or fluoro;
n is 0 or 1, and when n is 1, the $R^6$ group is methyl; or a pharmaceutically-acceptable salt thereof.

A further particular group of compounds of the invention are chromenone compounds of Formula I above wherein:—
$R^1$ is methyl or 2-hydroxyethyl;
$R^2$ is methyl; or
$R^1$ and $R^2$ together form a nitrogen containing heterocyclyl ring system, selected from azetidin-1-yl, morpholin-4-yl, 1-oxotetrahydro-1,4-thiazin-4-yl, piperidin-1-yl and 4-hydroxypiperidin-1-yl;
$R^3$ and $R^5$ are independently selected from H, fluoro, methoxy and cyano;

R⁴ is H or fluoro;
n is 0; or a pharmaceutically-acceptable salt thereof.

A further particular group of compounds of the invention are chromenone compounds of Formula I above wherein:—
R¹ and R² together form a nitrogen containing heterocyclyl ring system, selected from azetidin-1-yl, morpholin-4-yl, 1-oxotetrahydro-1,4-thiazin-4-yl, piperidin-1-yl and 4-hydroxypiperidin-1-yl;
R³ and R⁵ are independently selected from H, fluoro, methoxy and cyano;
R⁴ is H or fluoro;
n is 0; or a pharmaceutically-acceptable salt thereof.

A further particular group of compounds of the invention are chromenone compounds of Formula I above wherein:—
R¹ is methyl;
R² is methyl; or
R¹ and R² together form a morpholin-4-yl ring;
R³ and R⁵ are independently selected from H and fluoro;
R⁴ is H;
n is 1, and the R⁶ group is methyl; or a pharmaceutically-acceptable salt thereof.

A further particular group of compounds of the invention are chromenone compounds of Formula I above wherein:—
R¹ and R² together form a morpholin-4-yl ring;
R³ and R⁵ are independently selected from H and fluoro;
R⁴ is H;
n is 1, and the R⁶ group is methyl; or a pharmaceutically-acceptable salt thereof.

A further particular group of compounds of the invention are chromenone compounds of Formula I above wherein:—
R¹ and R² together form a morpholin-4-yl ring;
R³ and R⁵ are fluoro;
R⁴ is H;
n is 0; or a pharmaceutically-acceptable salt thereof.

Particular compounds of the invention are, for example, the chromenone compounds of the Formula I that are disclosed within the Examples that are set out hereinafter. For the avoidance of doubt, while compounds have been named according to IUPAC guidelines there may be multiple correct names for particular Examples. For instance, the compound of Example 1.03b can be named as 8-[(2R)-1-(3,5-difluorophenyl)pyrrolidin-2-yl]-6-(morpholine-4-carbonyl)-2-morpholino-chromen-4-one, or as 8-[(2R)-1-(3,5-difluorophenyl)pyrrolidin-2-yl]-6-(morpholine-4-carbonyl)-2-morpholino-4H-chromen-4-one.

For example, a particular compound of the invention is a chromenone derivative of the Formula I selected from any one of the following:—
8-(1-(3,5-difluorophenyl)pyrrolidin-2-yl)-N,N-dimethyl-2-morpholino-4-oxo-4H-chromene-6-carboxamide;
8-(1-(3,5-difluorophenyl)pyrrolidin-2-yl)-6-(morpholine-4-carbonyl)-2-morpholino-4H-chromen-4-one;
8-[(2S)-1-(3,5-difluorophenyl)pyrrolidin-2-yl]-6-(morpholine-4-carbonyl)-2-morpholino-chromen-4-one;
8-[(2R)-1-(3,5-difluorophenyl)pyrrolidin-2-yl]-6-(morpholine-4-carbonyl)-2-morpholino-chromen-4-one;
6-(azetidine-1-carbonyl)-8-(1-(3,5-difluorophenyl)pyrrolidin-2-yl)-2-morpholino-4H-chromen-4-one;
6-(azetidine-1-carbonyl)-8-[(2S)-1-(3,5-difluorophenyl)pyrrolidin-2-yl]-2-morpholino-chromen-4-one;
6-(azetidine-1-carbonyl)-8-[(2R)-1-(3,5-difluorophenyl)pyrrolidin-2-yl]-2-morpholino-chromen-4-one;
8-(1-(3-fluorophenyl)pyrrolidin-2-yl)-N,N-dimethyl-2-morpholino-4-oxo-4H-chromene-6-carboxamide;
8-[(2S)-1-(3-fluorophenyl)pyrrolidin-2-yl]-N,N-dimethyl-2-morpholino-4-oxo-chromene-6-carboxamide;
8-[(2R)-1-(3-fluorophenyl)pyrrolidin-2-yl]-N,N-dimethyl-2-morpholino-4-oxo-chromene-6-carboxamide;
8-(1-(3-fluorophenyl)pyrrolidin-2-yl)-6-(morpholine-4-carbonyl)-2-morpholino-4H-chromen-4-one;
8-[(2S)-1-(3-fluorophenyl)pyrrolidin-2-yl]-6-(morpholine-4-carbonyl)-2-morpholino-chromen-4-one;
8-[(2R)-1-(3-fluorophenyl)pyrrolidin-2-yl]-6-(morpholine-4-carbonyl)-2-morpholino-chromen-4-one;
6-(azetidine-1-carbonyl)-8-(1-(3-fluorophenyl)pyrrolidin-2-yl)-2-morpholino-4H-chromen-4-one;
6-(azetidine-1-carbonyl)-8-[(2S)-1-(3-fluorophenyl)pyrrolidin-2-yl]-2-morpholino-chromen-4-one;
6-(azetidine-1-carbonyl)-8-[(2R)-1-(3-fluorophenyl)pyrrolidin-2-yl]-2-morpholino-chromen-4-one;
8-(1-(3-fluorophenyl)pyrrolidin-2-yl)-N,N-dimethyl-2-morpholino-4-oxo-4H-chromene-6-carboxamide;
8-(1-(3,5-difluorophenyl)pyrrolidin-2-yl)-2-((R)-2-methylmorpholino)-6-(morpholine-4-carbonyl)-4H-chromen-4-one;
8-(1-(3-fluorophenyl)pyrrolidin-2-yl)-2-((R)-2-methylmorpholino)-6-(morpholine-4-carbonyl)-4H-chromen-4-one; and
8-(1-(3-fluorophenyl)pyrrolidin-2-yl)-N,N-dimethyl-2-((R)-2-methylmorpholino)-4-oxo-4H-chromene-6-carboxamide; or a pharmaceutically-acceptable salt thereof.

According to a yet further aspect of the invention, a particular compound of the invention is a chromenone derivative of the Formula I selected from any one of the following:—
8-(1-(3,5-difluorophenyl)pyrrolidin-2-yl)-N,N-dimethyl-2-morpholino-4-oxo-4H-chromene-6-carboxamide;
8-(1-(3,5-difluorophenyl)pyrrolidin-2-yl)-6-(morpholine-4-carbonyl)-2-morpholino-4H-chromen-4-one;
8-[(2R)-1-(3,5-difluorophenyl)pyrrolidin-2-yl]-6-(morpholine-4-carbonyl)-2-morpholino-chromen-4-one;
6-(azetidine-1-carbonyl)-8-(1-(3,5-difluorophenyl)pyrrolidin-2-yl)-2-morpholino-4H-chromen-4-one;
6-(azetidine-1-carbonyl)-8-[(2R)-1-(3,5-difluorophenyl)pyrrolidin-2-yl]-2-morpholino-chromen-4-one;
8-(1-(3-fluorophenyl)pyrrolidin-2-yl)-N,N-dimethyl-2-morpholino-4-oxo-4H-chromene-6-carboxamide;
8-[(2R)-1-(3-fluorophenyl)pyrrolidin-2-yl]-N,N-dimethyl-2-morpholino-4-oxo-chromene-6-carboxamide;
8-(1-(3-fluorophenyl)pyrrolidin-2-yl)-6-(morpholine-4-carbonyl)-2-morpholino-4H-chromen-4-one;
8-[(2R)-1-(3-fluorophenyl)pyrrolidin-2-yl]-6-(morpholine-4-carbonyl)-2-morpholino-chromen-4-one;
6-(azetidine-1-carbonyl)-8-(1-(3-fluorophenyl)pyrrolidin-2-yl)-2-morpholino-4H-chromen-4-one;
6-(azetidine-1-carbonyl)-8-[(2R)-1-(3-fluorophenyl)pyrrolidin-2-yl]-2-morpholino-chromen-4-one;
8-(1-(3-fluorophenyl)pyrrolidin-2-yl)-N,N-dimethyl-2-morpholino-4-oxo-4H-chromene-6-carboxamide;
8-(1-(3,5-difluorophenyl)pyrrolidin-2-yl)-2-((R)-2-methylmorpholino)-6-(morpholine-4-carbonyl)-4H-chromen-4-one;
8-(1-(3-fluorophenyl)pyrrolidin-2-yl)-2-((R)-2-methylmorpholino)-6-(morpholine-4-carbonyl)-4H-chromen-4-one; and
8-(1-(3-fluorophenyl)pyrrolidin-2-yl)-N,N-dimethyl-2-((R)-2-methylmorpholino)-4-oxo-4H-chromene-6-carboxamide; or a pharmaceutically-acceptable salt thereof According to a yet further aspect of the invention, a particular compound of the invention is a chromenone derivative of the Formula I selected from any one of the following:—
8-(1-(3,5-difluorophenyl)pyrrolidin-2-yl)-N,N-dimethyl-2-morpholino-4-oxo-4H-chromene-6-carboxamide;

8-(1-(3,5-difluorophenyl)pyrrolidin-2-yl)-6-(morpholine-4-carbonyl)-2-morpholino-4H-chromen-4-one;
8-[(2S)-1-(3,5-difluorophenyl)pyrrolidin-2-yl]-6-(morpholine-4-carbonyl)-2-morpholino-chromen-4-one;
6-(azetidine-1-carbonyl)-8-(1-(3,5-difluorophenyl)pyrrolidin-2-yl)-2-morpholino-4H-chromen-4-one;
6-(azetidine-1-carbonyl)-8-[(2S)-1-(3,5-difluorophenyl)pyrrolidin-2-yl]-2-morpholino-chromen-4-one;
8-(1-(3-fluorophenyl)pyrrolidin-2-yl)-N,N-dimethyl-2-morpholino-4-oxo-4H-chromene-6-carboxamide;
8-[(2S)-1-(3-fluorophenyl)pyrrolidin-2-yl]-N,N-dimethyl-2-morpholino-4-oxo-chromene-6-carboxamide;
8-(1-(3-fluorophenyl)pyrrolidin-2-yl)-6-(morpholine-4-carbonyl)-2-morpholino-4H-chromen-4-one;
8-[(2S)-1-(3-fluorophenyl)pyrrolidin-2-yl]-6-(morpholine-4-carbonyl)-2-morpholino-chromen-4-one;
6-(azetidine-1-carbonyl)-8-(1-(3-fluorophenyl)pyrrolidin-2-yl)-2-morpholino-4H-chromen-4-one;
6-(azetidine-1-carbonyl)-8-[(2S)-1-(3-fluorophenyl)pyrrolidin-2-yl]-2-morpholino-chromen-4-one;
8-(1-(3-fluorophenyl)pyrrolidin-2-yl)-N,N-dimethyl-2-morpholino-4-oxo-4H-chromene-6-carboxamide;
8-(1-(3,5-difluorophenyl)pyrrolidin-2-yl)-2-((R)-2-methylmorpholino)-6-(morpholine-4-carbonyl)-4H-chromen-4-one;
8-(1-(3-fluorophenyl)pyrrolidin-2-yl)-2-((R)-2-methylmorpholino)-6-(morpholine-4-carbonyl)-4H-chromen-4-one; and
8-(1-(3-fluorophenyl)pyrrolidin-2-yl)-N,N-dimethyl-2-((R)-2-methylmorpholino)-4-oxo-4H-chromene-6-carboxamide; or a pharmaceutically-acceptable salt thereof.

According to a further aspect of the invention, a particular compound of the invention is the compound of Example 1.03; or a pharmaceutically-acceptable salt thereof.

According to a further aspect of the invention, a particular compound of the invention is the compound of Example 1.05; or a pharmaceutically-acceptable salt thereof.

According to a further aspect of the invention, a particular compound of the invention is the compound of Example 1.06; or a pharmaceutically-acceptable salt thereof.

According to a further aspect of the invention, a particular compound of the invention is the compound of Example 1.07; or a pharmaceutically-acceptable salt thereof.

According to a further aspect of the invention, a particular compound of the invention is the compound of Example 1.03b; or a pharmaceutically-acceptable salt thereof.

According to a further aspect of the invention, a particular compound of the invention is (−)-8-(1-(3,5-difluorophenyl)pyrrolidin-2-yl)-6-(morpholine-4-carbonyl)-2-morpholino-4H-chromen-4-one; or a pharmaceutically-acceptable salt thereof, where the (−)-in the chemical name signifies the optical rotation measured using the conditions described in Example 1.03b.

According to a further aspect of the invention, a particular compound of the invention is (−)-8-(1-(3,5-difluorophenyl)pyrrolidin-2-yl)-6-(morpholine-4-carbonyl)-2-morpholino-4H-chromen-4-one; where the (−)-in the chemical name signifies the optical rotation measured using the conditions described in Example 1.03b.

According to a further aspect of the invention, a particular compound of the invention is a pharmaceutically acceptable salt of (−)-8-(1-(3,5-difluorophenyl)pyrrolidin-2-yl)-6-(morpholine-4-carbonyl)-2-morpholino-4H-chromen-4-one; where the (−)-in the chemical name signifies the optical rotation measured using the conditions described in Example 1.03b.

According to a further aspect of the invention, a particular compound of the invention is 8-[(2R)-1-(3,5-difluorophenyl) pyrrolidin-2-yl]-6-(morpholine-4-carbonyl)-2-morpholino-chromen-4-one; or a pharmaceutically-acceptable salt thereof.

According to a further aspect of the invention, a particular compound of the invention is 8-[(2R)-1-(3,5-difluorophenyl) pyrrolidin-2-yl]-6-(morpholine-4-carbonyl)-2-morpholino-chromen-4-one.

According to a further aspect of the invention, a particular compound of the invention is a pharmaceutically-acceptable salt of 8-[(2R)-1-(3,5-difluorophenyl)pyrrolidin-2-yl]-6-(morpholine-4-carbonyl)-2-morpholino-chromen-4-one.

According to a further aspect of the invention, a particular compound of the invention is 8-[(2S)-1-(3,5-difluorophenyl) pyrrolidin-2-yl]-6-(morpholine-4-carbonyl)-2-morpholino-chromen-4-one; or a pharmaceutically-acceptable salt thereof.

According to a further aspect of the invention, a particular compound of the invention is 8-[(2S)-1-(3,5-difluorophenyl) pyrrolidin-2-yl]-6-(morpholine-4-carbonyl)-2-morpholino-4H-chromen-4-one.

According to a further aspect of the invention, a particular compound of the invention is a pharmaceutically-acceptable salt of 8-[(2S)-1-(3,5-difluorophenyl)pyrrolidin-2-yl]-6-(morpholine-4-carbonyl)-2-morpholino-4H-chromen-4-one.

According to a further aspect of the invention, a particular compound of the invention is 8-(1-(3-fluorophenyl)pyrrolidin-2-yl)-6-(4-methylpiperazine-1-carbonyl)-2-morpholino-4H-chromen-4-one; or a pharmaceutically-acceptable salt thereof.

According to a further aspect of the invention, a particular compound of the invention is 8-(1-(3-fluorophenyl)pyrrolidin-2-yl)-6-(4-methylpiperazine-1-carbonyl)-2-morpholino-4H-chromen-4-one.

According to a further aspect of the invention, a particular compound of the invention is a pharmaceutically-acceptable salt of 8-(1-(3-fluorophenyl)pyrrolidin-2-yl)-6-(4-methylpiperazine-1-carbonyl)-2-morpholino-4H-chromen-4-one.

According to a further aspect of the invention, a particular compound of the invention is 8-[(2R)-1-(3-fluorophenyl)pyrrolidin-2-yl)-6-(4-methylpiperazine-1-carbonyl)-2-morpholino-4H-chromen-4-one; or a pharmaceutically-acceptable salt thereof.

According to a further aspect of the invention, a particular compound of the invention is 8-[(2R)-(1-(3-fluorophenyl)pyrrolidin-2-yl)]-6-(4-methylpiperazine-1-carbonyl)-2-morpholino-4H-chromen-4-one.

According to a further aspect of the invention, a particular compound of the invention is a pharmaceutically-acceptable salt of 8-[(2R)-(1-(3-fluorophenyl)pyrrolidin-2-yl)]-6-(4-methylpiperazine-1-carbonyl)-2-morpholino-4H-chromen-4-one.

According to a further aspect of the invention, a particular compound of the invention is 8-[(2S)-(1-(3-fluorophenyl)pyrrolidin-2-yl)]-6-(4-methylpiperazine-1-carbonyl)-2-morpholino-4H-chromen-4-one; or a pharmaceutically-acceptable salt thereof.

According to a further aspect of the invention, a particular compound of the invention is 8-[(2S)-(1-(3-fluorophenyl)pyrrolidin-2-yl)]-6-(4-methylpiperazine-1-carbonyl)-2-morpholino-4H-chromen-4-one.

According to a further aspect of the invention, a particular compound of the invention is a pharmaceutically-acceptable salt of 8-[(2S)-(1-(3-fluorophenyl)pyrrolidin-2-yl)]-6-(4-methylpiperazine-1-carbonyl)-2-morpholino-4H-chromen-4-one.

According to a further aspect of the invention, a particular compound of the invention is 8-[1-(3-methoxyphenyl)pyrrolidin-2-yl]-6-(morpholine-4-carbonyl)-2-morpholino-4H-chromen-4-one; or a pharmaceutically-acceptable salt thereof.

According to a further aspect of the invention, a particular compound of the invention is 8-[1-(3-methoxyphenyl)pyrrolidin-2-yl]-6-(morpholine-4-carbonyl)-2-morpholino-4H-chromen-4-one.

According to a further aspect of the invention, a particular compound of the invention is a pharmaceutically-acceptable salt of 8-[1-(3-methoxyphenyl)pyrrolidin-2-yl]-6-(morpholine-4-carbonyl)-2-morpholino-4H-chromen-4-one.

According to a further aspect of the invention, a particular compound of the invention is 8-[(2R)-1-(3-methoxyphenyl)pyrrolidin-2-yl]-6-(morpholine-4-carbonyl)-2-morpholino-4H-chromen-4-one; or a pharmaceutically-acceptable salt thereof.

According to a further aspect of the invention, a particular compound of the invention is 8-[(2R)-1-(3-methoxyphenyl)pyrrolidin-2-yl]-6-(morpholine-4-carbonyl)-2-morpholino-4H-chromen-4-one.

According to a further aspect of the invention, a particular compound of the invention is a pharmaceutically-acceptable salt of 8-[(2R)-1-(3-methoxyphenyl)pyrrolidin-2-yl]-6-(morpholine-4-carbonyl)-2-morpholino-4H-chromen-4-one.

According to a further aspect of the invention, a particular compound of the invention is 8-[(2S)-1-(3-methoxyphenyl)pyrrolidin-2-yl]-6-(morpholine-4-carbonyl)-2-morpholino-4H-chromen-4-one; or a pharmaceutically-acceptable salt thereof.

According to a further aspect of the invention, a particular compound of the invention is 8-[(2S)-1-(3-methoxyphenyl)pyrrolidin-2-yl]-6-(morpholine-4-carbonyl)-2-morpholino-4H-chromen-4-one.

According to a further aspect of the invention, a particular compound of the invention is a pharmaceutically-acceptable salt of 8-[(2S)-1-(3-methoxyphenyl)pyrrolidin-2-yl]-6-(morpholine-4-carbonyl)-2-morpholino-4H-chromen-4-one.

Another aspect of the present invention provides a process for preparing a compound of the Formula I, or a pharmaceutically-acceptable salt thereof. A suitable process is illustrated by the following representative process variants in which, unless otherwise stated, $R^1$, $R^2$, $R^3$, $R^4$, $R^5$, n and $R^6$ have any of the meanings defined hereinbefore. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

Suitable process variants include, for example, the following:—

(a) The cross coupling reaction of a compound of the Formula II:

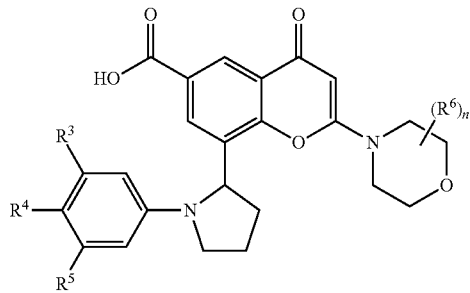

wherein $R^3$, $R^4$, $R^5$, n and $R^6$ have any of the meanings defined hereinbefore except that any functional group present is protected if necessary, with an amine of the Formula III:

wherein $R^1$ and $R^2$ have any of the meanings defined hereinbefore except that any functional group is protected if necessary. The reaction can be carried out in the presence of a suitable coupling agent such as, for example, TSTU (2-(2,5-dioxopyrrolidin-1-yl)-1,1,3,3-tetramethylisouronium tetrafluoroborate) or TBTU (2-(1H-benzo[d][1,2,3]triazol-1-yl)-1,1,3,3-tetramethylisouronium tetrafluoroborate), or 1-propylphosphonic anhydride cyclic trimer, whereafter any protecting group that is present is removed.

The reaction is conveniently carried out in the presence of a suitable base. A suitable base is, for example, an organic amine base such as, for example, pyridine, 2,6-lutidine, collidine, 4-dimethylaminopyridine, triethylamine, N-methylmorpholine, diazabicyclo[5.4.0]undec-7-ene, diisopropylethyl amine, or, for example, an alkali or alkaline earth metal carbonate or hydroxide, for example sodium carbonate, potassium carbonate, calcium carbonate, sodium hydroxide or potassium hydroxide.

The reaction is conveniently carried out in the presence of a suitable inert solvent such as for example, N,N-dimethylformamide, N-methylpyrrolidone, tetrahydrofuran, 1,4-dioxane, 1,2-dimethoxyethane, benzene, toluene, xylene, methanol ethanol, halogenated solvents such as dichloromethane, chloroform or carbon tetrachloride and at a temperature in the range, for example −50° C. to 100° C., preferably in the range 0° C. to 30° C.

Alternatively, the carboxylic acid compound of the Formula II may be transformed into an activated species (such as an acid chloride, by for example treatment with oxalyl chloride), which can then be reacted with a compound of the Formula III under conditions well known in the art.

Compounds of the Formula II may, for example, be prepared by a saponification reaction, of a compound of the Formula IIa:

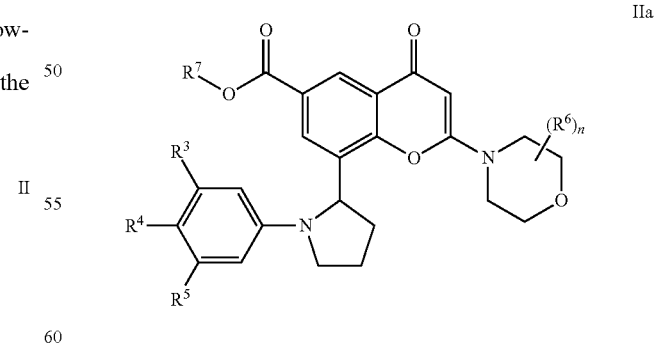

wherein $R^3$, $R^4$, $R^5$, n and $R^6$ have any of the meanings defined hereinbefore and $R^7$ is (1-6C)alkyl, conveniently methyl or ethyl.

The saponification reaction can be conducted for example by treatment of a compound of Formula IIa with an alkali or alkaline earth metal hydroxide such as lithium hydroxide, potassium hydroxide or sodium hydroxide in a suitable solvent such as for example a mixture of ethanol and water, or water and a water miscible solvent, such as for example tetrahydrofuran or dioxane, at a temperature in the range, for example 0° C. to −100° C., preferably in the range 20-40° C.

Compounds of the Formula IIa may, for example, be prepared by the reaction, conveniently in the presence of a suitable catalyst, of a compound of the Formula IV:

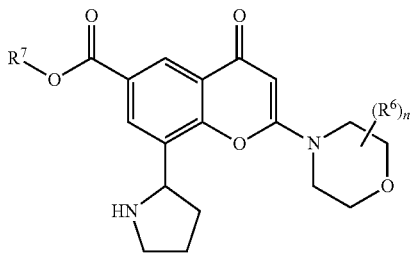

IV wherein n and $R^6$ have any of the meanings defined hereinbefore, and $R^7$ is (1-6C)alkyl, conveniently methyl or ethyl, with a compound of the Formula V

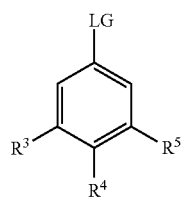

V wherein $R^3$, $R^4$ and $R^5$ have any of the meanings defined hereinbefore except that any functional group is protected if necessary, and LG is a suitable leaving group, such as for example, a halogeno group such as a chloro, bromo, iodo group (conveniently bromo or iodo), whereafter any protecting group that is present is removed.

A suitable catalyst for the reaction includes, for example, a metallic catalyst such as palladium(0), for example tetrakis(triphenylphosphine)palladium(0); or a catalyst formed in-situ from a palladium (II) salt, for example palladium(II) acetate, palladium(II) chloride, palladium(II) bromide, bis(triphenylphosphine)palladium(II) chloride, [1,1'-bis(diphenylphosphino)ferrocene]dichloropalladium(II), or tris(dibenzilideneacetone)dipalladium, and a phosphine ligand, for example, (9,9-dimethyl-9H-xanthene-4,5-diyl)bis(diphenylphosphine).

The reaction is conveniently carried out in a suitable solvent such as, N,N-dimethylformamide, tetrahydrofuran, 1,4-dioxane, 1,2-dimethoxyethane, benzene, toluene or xylene and at a temperature in the range, for example 20° C. to 150° C., preferably in the range 60° C. to 120° C.

The reaction is also conveniently carried out in the presence of a base, such as for example cesium carbonate, potassium carbonate or sodium carbonate, conveniently cesium carbonate.

Suitable reactions of this type are described as Buchwald type palladium coupling reactions in 'Metal-Catalyzed Cross-Coupling Reactions', Second Edition, Edited by Armin Meijere, François Diederich, Wiley-VCH, 2004, Volume 1, p 699).

An example of such a reaction is described at Step 4 of the preparation of the starting material 8-(1-(3,5-difluorophenyl)pyrrolidin-2-yl)-2-morpholino-4-oxo-4H-chromene-6-carboxylic acid in Example 1.00.

Alternatively, compounds of the Formula IIa can be prepared by Chan-Lam coupling type reactions, in which a compound of the Formula IV is reacted with a compound of the Formula Va:

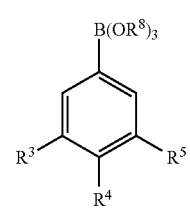

Va wherein $R^3$, $R^4$ and $R^5$ has any of the meanings defined hereinbefore except that any functional group is protected if necessary, and $R^8$ is (1-3C)alkyl or H.

Such a reaction is conveniently carried out in the presence of a copper source, such as for example copper(II) acetate in DCM, and is carried out by way of exposure to atmospheric oxygen at ambient temperature (Tetrahedron Letters, 1998, 2933).

Compounds of the Formula IV may be prepared by hydrogenation of a compound of the Formula VI:

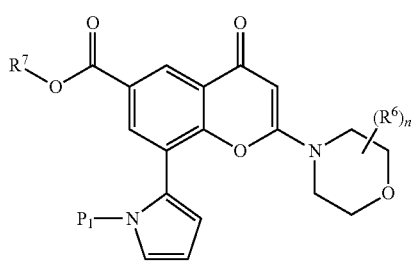

VI wherein n and $R^6$ have any of the meanings defined hereinbefore, $R^7$ is (1-6C)alkyl, conveniently methyl or ethyl, and $P_1$ is a protecting group, such as for example a carbamate, such as tert-butoxycarbonyl, followed by removal of $P_1$.

The reaction is conveniently carried out in the presence of a suitable solvent, for example, an alcohol such as methanol, N,N-dimethylformamide, tetrahydrofuran, 1,4-dioxane, 1,2-dimethoxyethane, benzene, toluene or xylene; conveniently in methanol and at a temperature in the range, for example 20° C. to 100° C., preferably in the range 50° C. to 80° C., under a pressure of hydrogen (1-100 atm), preferably around 5 atm in the presence of a catalyst such as palladium, rhodium, platinum, preferably 5% rhodium on alumina.

If $P_1$ is tert-butoxycarbonyl, removal of $P_1$ can be conveniently carried out with hydrogen chloride (dissolved for example in dioxane), in a solvent such as DCM at room temperature.

Alternatively, compounds of Formula IV may be prepared by reaction of a compound of the Formula VII (wherein n and $R^6$ have any of the meanings defined hereinbefore, and $R^7$ is (1-6C)alkyl, conveniently methyl or ethyl), with a compound of the Formula VIa:

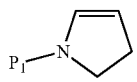

VIa is where P₁ is a protecting group, preferably an alkoxycarbonyl group, such as tert-butoxycarbonyl, under Heck coupling conditions, followed by deprotection of the P₁ group followed reduction of the resulting isomeric dihydropyrroles (or vice versa).

For further details of Heck coupling conditions see for example: 'Metal-Catalyzed Cross-Coupling Reactions', Edited by François Diederich and P. J. Stang, Wiley-VCH, 1998, p 99).

A suitable catalyst for the reaction includes, for example, a metallic catalyst such as palladium(II), for example dichlorobis(triphenylphosphine)palladium(II); or a catalyst formed in-situ from a palladium (II) salt, for example palladium(II) acetate, palladium(II) chloride, palladium(II) bromide, conveniently in the presence of a phosphine ligand, for example, tripheneyl phosphine.

The reaction is conveniently carried out in a suitable solvent such as, N,N-dimethylformamide, tetrahydrofuran, 1,4-dioxane, 1,2-dimethoxyethane, benzene, toluene or xylene and at a temperature in the range, for example 20° C. to 150° C., preferably in the range 60° C. to 120° C.

The reaction is also conveniently carried out in the presence of a base, such as for example cesium carbonate, potassium carbonate or sodium carbonate, conveniently potassium carbonate.

If P₁ is tert-butoxycarbonyl, removal of P₁ can be conveniently carried out with hydrogen chloride (dissolved for example in dioxane), in a solvent such as DCM at room temperature.

The reaction of reduction of the resulting isomeric dihydropyrroles is conveniently carried out in the presence of a suitable solvent such as for example, an alcohol such as methanol, N,N-dimethylformamide, tetrahydrofuran, 1,4-dioxane, 1,2-dimethoxyethane, benzene, toluene or xylene; conveniently in methanol and at a temperature in the range, for example 20° C. to 100° C., preferably in the range 20° C. to 60° C., under a pressure of hydrogen (1-100 atm), preferably around 5 atm in the presence of a catalyst such as palladium, rhodium, or platinum, preferably 5% palladium on charcoal.

Compounds of the Formula VI may, for example, be prepared by reaction of a compound of the Formula VII:

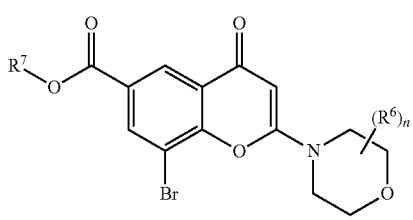

VII wherein n and R⁶ have any of the meanings defined hereinbefore, and R⁷ is (1-6C)alkyl, conveniently methyl or ethyl; with a compound of the Formula VIII:

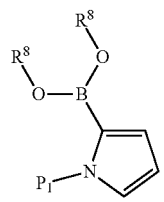

VIII wherein P₁ is a protecting group, such as for example a carbamate, such as for example tert-butoxycarbonyl, and R⁸ is (1-3C)alkyl or H, under Suzuki coupling conditions.

For further details of Suzuki coupling conditions see for example: 'Metal-Catalyzed Cross-Coupling Reactions', Edited by François Diederich and P. J. Stang, Wiley-VCH, 1998, p 49), whereafter P₁ is removed.

A suitable catalyst for the reaction includes, for example, a metallic catalyst such as palladium(0), for example tetrakis (triphenylphosphine)palladium(0); or a catalyst formed in-situ from a palladium (II) salt, for example palladium(II) acetate, palladium(II) chloride, palladium(II) bromide, bis (triphenylphosphine)palladium(II) chloride, [1,1'-bis(diphenylphosphino)ferrocene]dichloropalladium(II), or tris (dibenzilideneacetone)dipalladium, conveniently in the presence of a phosphine ligand, for example, (9,9-dimethyl-9H-xanthene-4,5-diyl)bis(diphenylphosphine).

The reaction is conveniently carried out in a suitable solvent such as, N,N-dimethylformamide, tetrahydrofuran, 1,4-dioxane, 1,2-dimethoxyethane, benzene, toluene or xylene and at a temperature in the range, for example 20° C. to 150° C., preferably in the range 60° C. to 120° C.

The reaction is also conveniently carried out in the presence of an aqueous solution of a base, such as for example cesium carbonate, potassium carbonate or sodium carbonate, conveniently sodium carbonate.

Compounds of the Formula VII can be made from the coupling of a compound of the Formula IX:

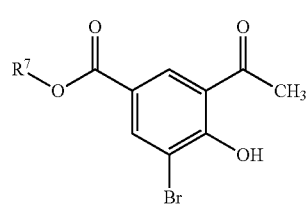

IX wherein R⁷ is (1-6C)alkyl, conveniently methyl or ethyl, with a compound of the Formula X:

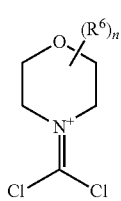

X wherein n and R⁶ have any of the meanings defined hereinbefore, in the presence of a suitable activating agent such as, for example, a Lewis acid, such as boron trifluoride-diethyl etherate complex.

Reaction of the compounds of the Formula IX with those of the Formula X is conveniently carried out in the presence of a suitable solvent such as, for example, N,N-dimethylformamide, tetrahydrofuran, 1,4-dioxane, 1,2-dimethoxyethane, benzene, toluene, xylene or halogenated solvents such as dichloromethane, chloroform or carbon tetrachloride and at a temperature in the range 20° C. to 150° C., preferably in the range 60° C. to 120° C.

Compounds of the Formula IX can be prepared for example as shown in the synthesis of methyl 8-bromo-2-morpholino-4-oxo-4H-chromene-6-carboxylate used as a starting material in Example 1.00. Compounds of the Formulae IX have also been described in the literature (Ger. Offen, DE 4318756, 1994 and Aust. J. Chem. 2003, 56, 1099), or they can be prepared by standard processes known in the art.

In particular, compounds of the Formulae VII may be obtained by procedures in accordance with the following scheme:

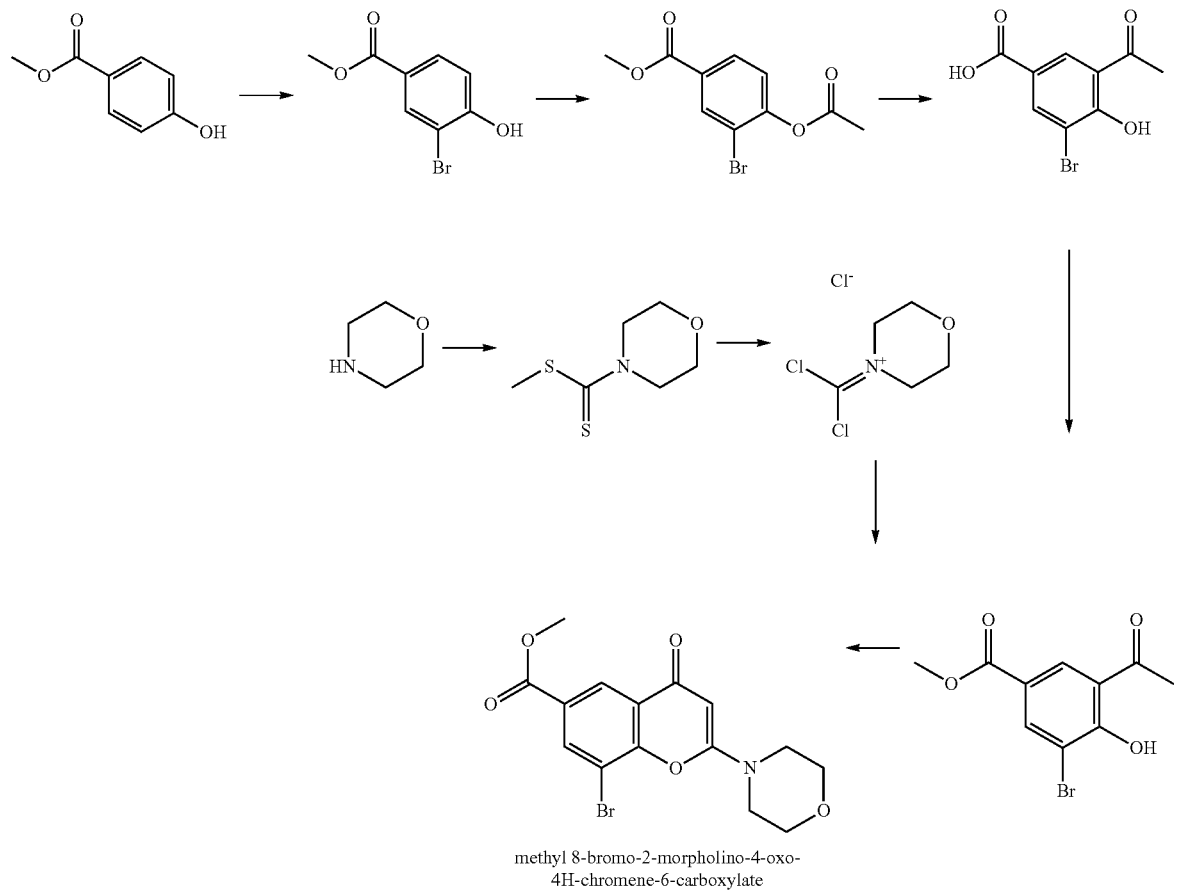

methyl 8-bromo-2-morpholino-4-oxo-4H-chromene-6-carboxylate

Compounds of the Formulae VII may alternatively be obtained by procedures in accordance with the following scheme, which has been described in more detail in Example 1.00 herein, where the method for preparing methyl 8-bromo-2-morpholino-4-oxo-4H-chromene-6-carboxylate using such a route is provided:

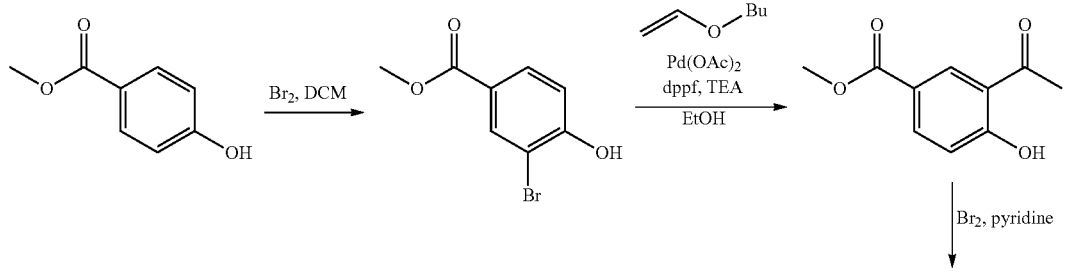

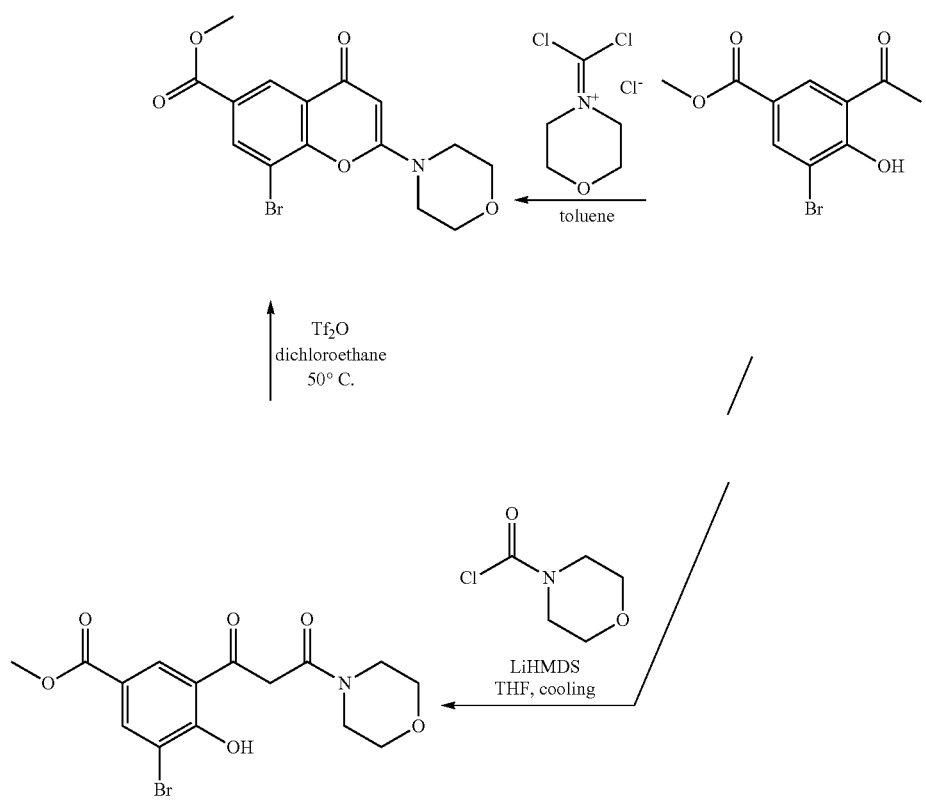

where Br₂ is bromine, Pd(OAc)₂ is palladium(II) acetate, DCM is dichloromethane, LiHMDS is Lithium bis(trimethylsilyl)amide, EtOH is ethanol, Dppf is 1,1'-bis (diphenylphosphino)ferrocene, TEA is triethylamine, THF is tetrahydrofuran and Tf₂O is Trifluoromethanesulfonic anhydride.

Compounds of the Formulae VII may also be obtained by on a large-scale procedure in accordance with the following scheme, which has been described in more detail in Example 1.00

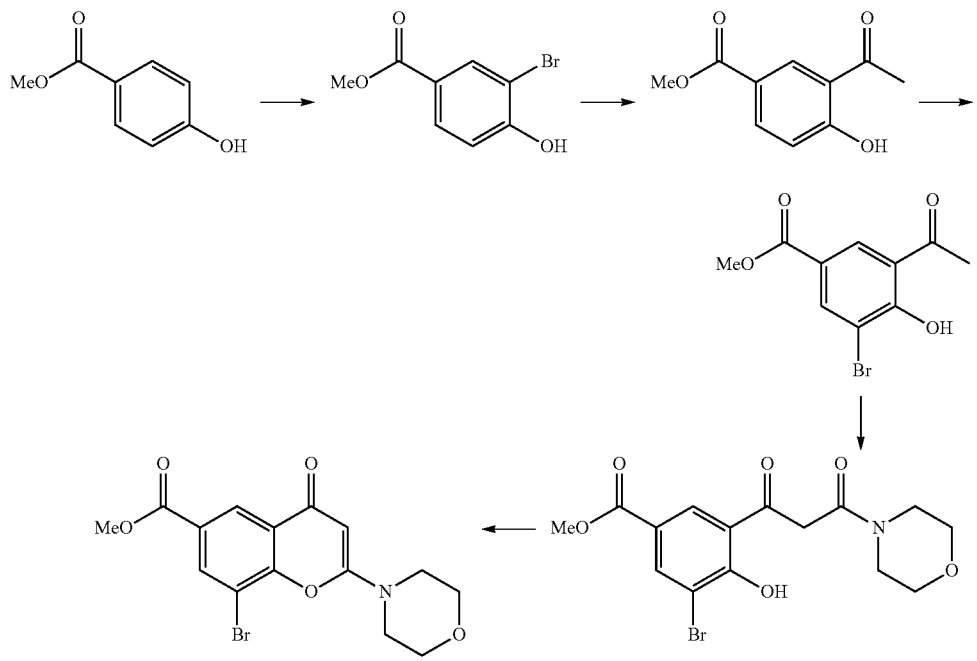

Compounds of the Formula VII may also be prepared by reaction of a compound of the Formula IX:

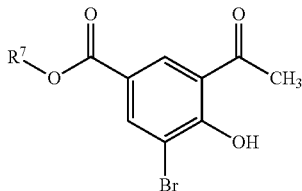

IX wherein $R^7$ is (1-6C)alkyl, conveniently methyl or ethyl, with a compound of the Formula Xa:

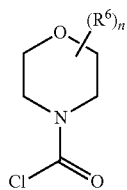

Xa wherein n and $R^6$ have any of the meanings defined hereinbefore, in the presence of a suitable activating agent such as, for example, a strong base, such as for example Lithium bis(trimethyl silyl)amide, to provide a compound of the Formula IXa:

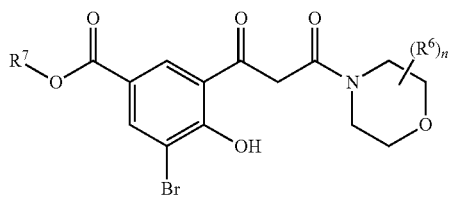

IXa whereafter a ring-closing reaction can be performed to form the compound of the Formula VII.

Reaction of the compounds of the Formula IX with those of the Formula Xa is conveniently carried out in the presence of a suitable solvent or diluent such as for example, tetrahydrofuran, 1,4-dioxane, 1,2-dimethoxyethane, benzene, toluene or xylene and at a temperature in the range, for example −100° C. to ambient temperature, preferably in the range −80° C. to 20° C.

The ring-closing reaction to convert a compound of the Formula IXa into a compound of the Formula VII can be conducted for example by treatment with a dehydrating agent, such as for example trifluoromethanesulfonic anhydride, in a suitable solvent such as for example dichloroethane at a temperature in the range, for example 0° C. to −100° C., conveniently in the range 20-60° C.

(b) The reaction, conveniently in the presence of a suitable catalyst as defined hereinbefore in process variant (a) above, of a compound of the Formula XI:

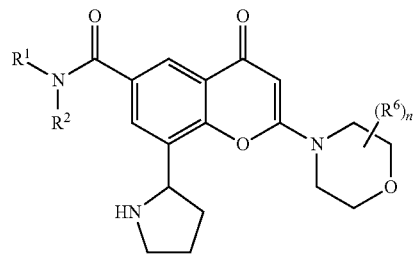

XI wherein $R^1$, $R^2$, n and $R^6$ have any of the meanings defined hereinbefore except that any functional group present is protected if necessary, with an compound of the Formula V

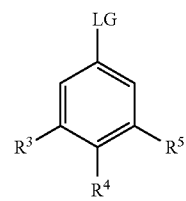

V wherein $R^3$, $R^4$, $R^5$ have any of the meanings defined hereinbefore and LG is a suitable leaving group, such as for example, a halogeno group such as a chloro, bromo, iodo group (conveniently bromo or iodo), whereafter any protecting group that is present is removed.

Suitable reactions of this type are described as palladium type coupling Buchwald reactions in 'Metal-Catalyzed Cross-Coupling Reactions', Second Edition, Edited by Armin Meijere, François Diederich, Wiley-VCH, 2004, Volume 1, p 699).

Suitable conditions for such reactions were described in process variant (a) hereinbefore.

Compounds of the Formula XI may, for example, be prepared by first saponifying a compound of the Formula XII:

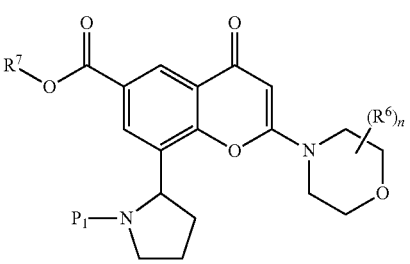

XII wherein n, $R^6$ and $P_1$ have any of the meanings defined hereinbefore and $R^7$ is (1-6C)alkyl, conveniently methyl or ethyl and any functional group present is protected if necessary and then subjecting the resultant acid to amide formation, conveniently in the presence of a suitable base and coupling agent, with an amine of the Formula III:

III wherein $R^1$ and $R^2$ have any of the meanings defined hereinbefore except that any functional group is protected if necessary, in the presence of a suitable coupling agent such as, for example, TSTU (2-(2,5-dioxopyrrolidin-1-yl)-1,1,3,3-tetramethylisouronium tetrafluoroborate) or TBTU (2-(1H- benzo[d][1,2,3]triazol-1-yl)-1,1,3,3-tetramethylisouronium tetrafluoroborate), whereafter $P_1$ and any other any protecting group that is present is removed.

The saponification reaction can be conducted for example by treatment of a compound of Formula XII with an alkali or alkaline earth metal hydroxide such as lithium hydroxide, potassium hydroxide or sodium hydroxide in a suitable solvent such as for example a mixture of ethanol and water, or water and a water miscible solvent, such as for example tetrahydrofuran or dioxane, at a temperature in the range, for example 0° C. to −100° C., preferably in the range 20-40° C.

The amide coupling reaction is conveniently carried out in the presence of a suitable base. A suitable base is, for example, an organic amine base such as, for example, pyridine, 2,6-lutidine, collidine, 4-dimethylaminopyridine, triethylamine, N-methylmorpholine, diazabicyclo[5.4.0]undec-7-ene, diisopropylethyl amine, or, for example, an alkali or alkaline earth metal carbonate or hydroxide, for example sodium carbonate, potassium carbonate, calcium carbonate, sodium hydroxide or potassium hydroxide.

The reaction is conveniently carried out in the presence of a suitable inert solvent or diluent such as for example, N,N-dimethylformamide, N-methylpyrrolidone, tetrahydrofuran, 1,4-dioxane, 1,2-dimethoxyethane, benzene, toluene, xylene, methanol ethanol, halogenated solvents such as dichloromethane, chloroform or carbon tetrachloride and at a temperature in the range, for example −50° C. to 100° C., preferably in the range 0° C. to 30° C.

Alternatively for the amide coupling, the carboxylic acid may be transformed into an activated species (such as an acid chloride, suitably by treatment with oxalyl chloride), which is then reacted with a compound of the Formula III, conveniently in the presence of on organic base such as triethylamine.

If $P_1$ is tert-butoxycarbonyl, removal of $P_1$ can be conveniently carried out with hydrogen chloride (dissolved for example in dioxane), in a solvent such as DCM at room temperature.

Alternatively, a compound of the Formula XI can be obtained by reacting a compound of the Formula XIII:

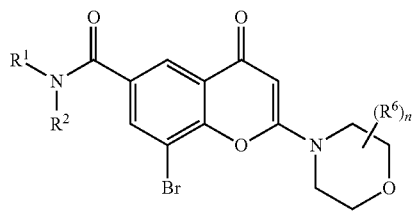

XIII wherein $R^1$, $R^2$, n and $R^6$ have any of the meanings defined hereinbefore except that any functional group present is protected if necessary, by a Suzuki reaction with compound of the Formula VIII:

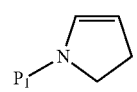

VIII wherein $P_1$ is a protecting group, such as for example a carbamate, such as for example tert-butoxycarbonyl, and $R^8$ is (1-3C)alkyl or H, followed by hydrogenation and deprotection of $P_1$.

A suitable catalyst for the Suzuki reaction is, for example, a metallic catalyst such as palladium(0), for example tetrakis (triphenylphosphine)palladium(0); or a catalyst formed in-situ from a palladium (II) salt, for example palladium(II) acetate, palladium(II) chloride, palladium(II) bromide, bis (triphenylphosphine)palladium(II) chloride, [1,1'-bis(diphenylphosphino)ferrocene]dichloropalladium(II), tris(dibenzilideneacetone)dipalladium, conveniently in the presence of a phosphine ligand, for example, (9,9-dimethyl-9H-xanthene-4,5-diyl)bis(diphenylphosphine).

The reaction is conveniently carried out in a suitable solvent such as, N,N-dimethylformamide, tetrahydrofuran, 1,4-dioxane, 1,2-dimethoxyethane, benzene, toluene or xylene and at a temperature in the range, for example 20° C. to 150° C., preferably in the range 60° C. to 120° C.

The reaction is also conveniently carried out in the presence of an aqueous solution of a base (typically cesium carbonate, potassium carbonate or sodium carbonate; preferably sodium carbonate).

If $P_1$ is tert-butoxycarbonyl, deprotection can be conveniently carried out with hydrogen chloride (dissolved for example in dioxane), in a solvent such as DCM at room temperature.

The hydrogenation reaction is conveniently carried out in the presence of a suitable solvent such as for example, alcohols, such as methanol; or N,N-dimethylformamide, tetrahydrofuran, 1,4-dioxane, 1,2-dimethoxyethane, benzene, toluene or xylene; preferably methanol and at a temperature in the range, for example 20° C. to 100° C., preferably in the range 50° C. to 80° C., under a pressure of hydrogen (1-100 atm), preferably around 5 atm in the presence of a catalyst such as palladium, rhodium or platinum, preferably rhodium 5% on alumina).

Alternatively, compounds of Formula XI may be prepared by reaction of compound XIII wherein $R^1$, $R^2$, n and $R^6$ have any of the meanings defined hereinbefore except that any functional group present is protected if necessary, with a compound of the Formula VIIIa

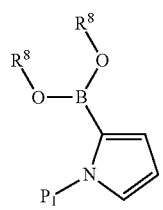

VIIIa where $P_1$ is a protecting group, preferably an alkoxycarbonyl group such as tert-butoxycarbonyl, under Heck coupling conditions, followed by deprotection of the P1 group, followed by reduction of the resulting isomeric dihydropyrroles (or vice versa).

For further details of Heck coupling conditions see for example: 'Metal-Catalyzed Cross-Coupling Reactions', Edited by François Diederich and P. J. Stang, Wiley-VCH, 1998, p 99).

A suitable catalyst for the reaction includes, for example, a metallic catalyst such as palladium(II), for example dichlorobis(triphenylphosphine)palladium(II); or a catalyst formed in-situ from a palladium (II) salt, for example palladium(II) acetate, palladium(II) chloride, palladium(II) bromide, conveniently in the presence of a phosphine ligand, for example, tripheneyl phosphine.

The reaction is conveniently carried out in a suitable solvent such as, N,N-dimethylformamide, tetrahydrofuran, 1,4-dioxane, 1,2-dimethoxyethane, benzene, toluene or xylene and at a temperature in the range, for example 20° C. to 150° C., preferably in the range 60° C. to 120° C.

The reaction is also conveniently carried out in the presence of a base, such as for example cesium carbonate, potassium carbonate or sodium carbonate, conveniently potassium carbonate.

If $P_1$ is tert-butoxycarbonyl, removal of $P_1$ can be conveniently carried out with hydrogen chloride (dissolved for example in dioxane) or trifluoroactic acid, in a solvent such as DCM at room temperature.

The reaction of reduction of the resulting isomeric dihydropyrroles is conveniently carried out in the presence of a suitable solvent such as for example, an alcohol such as methanol, N,N-dimethylformamide, tetrahydrofuran, 1,4-dioxane, 1,2-dimethoxyethane, benzene, toluene or xylene; conveniently in methanol and at a temperature in the range, for example 20° C. to 100° C., preferably in the range 20° C. to 60° C., under a pressure of hydrogen (1-100 atm), preferably around 5 atm in the presence of a catalyst such as palladium, rhodium, platinum such as platinum(IV) oxide, preferably 5% palladium on charcoal.

An example of a process scheme that may be used for the synthesis of a compound of the Formula XIII, such as for example 8-bromo-N,N-dimethyl-2-(morpholin-4-yl)-4-oxo-4H-chromene-6-carboxamide, is the following:

where NaOH is sodium hydroxide, $Me_2NH$ is dimethylamine, DCM is dichloromethane, LiHMDS is Lithium bis(trimethyl silyl)amide, EtOH is ethanol, DIPEA is diisopropylethylamine, THF is tetrahydrofuran, $Tf_2O$ is Trifluoromethanesulfonic anhydride and TBTU is 2-(1H-benzo[d][1,2,3]triazol-1-yl)-1,1,3,3-tetramethylisouronium tetrafluoroborate.

Alternatively, a compound of the Formula XIII can be made by reacting a compound of the Formula III with a compound of the Formula XIV together in an amide coupling reaction:

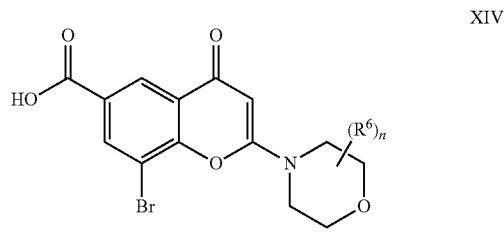

Compounds of the Formula XIV may be obtained by procedures in accordance with the following scheme:

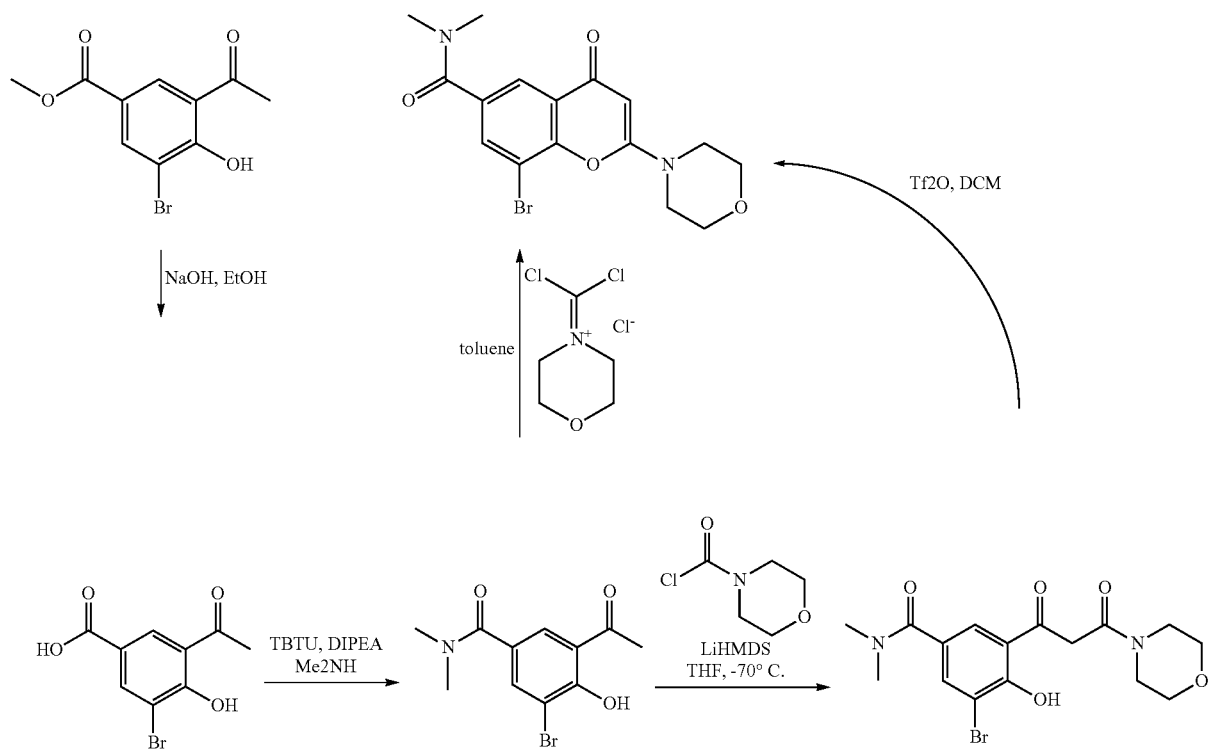

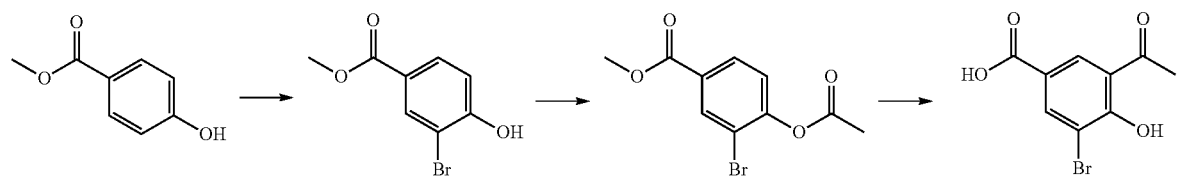

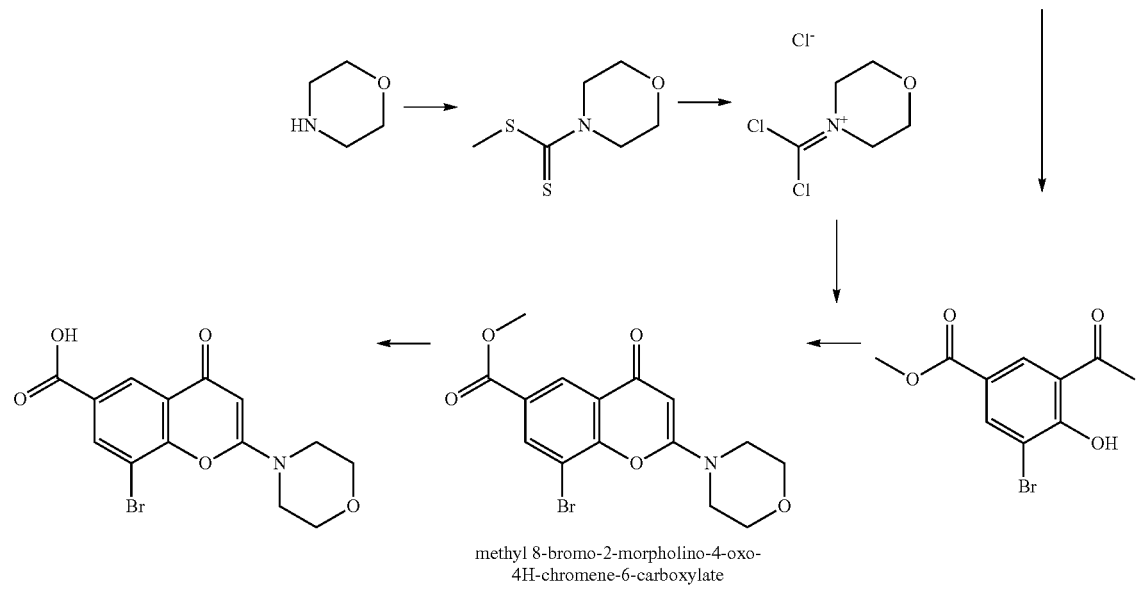

methyl 8-bromo-2-morpholino-4-oxo-
4H-chromene-6-carboxylate

Compounds of the Formula XIV may, for example, be prepared by saponification of a compound of Formula VII:

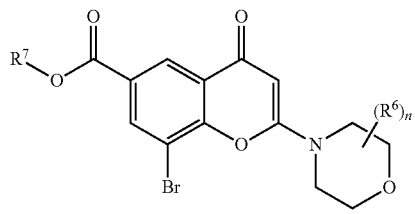

wherein n and $R^6$ have any of the meanings defined hereinbefore, $R^7$ is (1-6C)alkyl, conveniently methyl or ethyl.

The saponification reaction can be conducted for example by treatment of a compound of Formula VII with an alkali or alkaline earth metal hydroxide such as lithium hydroxide, potassium hydroxide or sodium hydroxide in a suitable solvent such as for example a mixture of ethanol and water, or water and a water miscible solvent, such as for example tetrahydrofuran or dioxane, at a temperature in the range, for example 0° C. to –100° C., preferably in the range 20-40° C.

It is to be understood that several steps can be combined without isolation or purification of intermediates. For example, compounds of the Formula XIII can be directly obtained from compounds of the Formula VII, as illustrated in Example 1.03b (large scale procedure), where a compound of Formula XIV is obtained from a compound of Formula VII. Here, the carboxylate salt of a compound of Formula XIV (obtained from saponification of VII without isolation) is directly reacted with an activating agent (such as 2-chloro-4,6-dimethoxy-1,3,5-triazine) to form an activated species (activated ester'), followed by reaction with an amine of Formula III to generate a compound of the Formula XIII.

It is to be understood that other permutations of the process steps in the process variants described above are also possible. For example, a Compound of Formula I could be prepared using analogous procedures to those described in process variants (a) to (b), but wherein the final step in the procedure is the introduction of the morpholine-$(R^6)_n$ group.

It is to be understood that any compound of Formula I obtained by any of the processes described hereinbefore can be converted into another compound of the Formula I if required.

When a pharmaceutically-acceptable salt of a chromenone derivative of the Formula I is required, for example an acid-addition salt, it may be obtained by, for example, reaction of said chromenone derivative with a suitable acid.

When a pharmaceutically-acceptable pro-drug of a chromenone derivative of the Formula I is required, it may be obtained using a conventional procedure. For example, an in vivo cleavable ester of a chromenone derivative of the Formula I may be obtained by, for example, reaction of a compound of the Formula I containing a hydroxy group with a pharmaceutically-acceptable carboxylic acid. For example, an in vivo cleavable amide of a chromenone derivative of the Formula I may be obtained by, for example, reaction of a compound of the Formula I containing an amino group with a pharmaceutically-acceptable carboxylic acid.

It will also be appreciated by the person skilled in the organic synthetic arts that certain of the ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents, acylation of substituents, amidation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that, in some of the reactions mentioned hereinbefore, it may be necessary or desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy, it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

The protecting groups may be removed at any convenient stage in the synthesis using conventional techniques well known in the chemical art.

Certain of the intermediates (for example, compounds of the Formulae II, IIa, IV, VI, VII, IXa, XI, XIII and XIV) defined herein are novel and these are provided as a further feature of the invention. For example, compounds of the Formula VII (wherein n and $R^6$ have any of the meanings defined hereinbefore) may be useful as intermediates in the preparation of particular compounds of the invention:

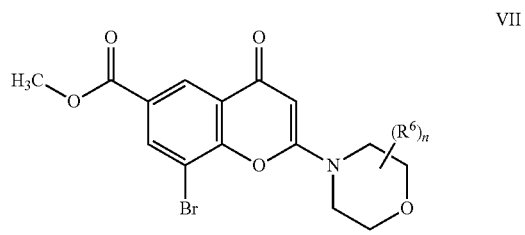

Biological Assays

The following assays can be used to measure the effects of the compounds of the present invention as inhibitors of PI3 kinase enzymes, as inhibitors in vitro of phospho AKT (ser473) in MDA-MB-468 cells, as inhibitors in vivo of phospho AKT (ser473) in Swiss athymic nu/nu mice, and as inhibitors in vivo of tumour growth in Swiss athymic nu/nu mice transplanted with the human prostatic adenocarcinoma cell line, PC3.

(a) In Vitro Enzyme Inhibition Assay

The inhibition of PI3Kβ, PI3Kα, PI3Kγ and PI3Kδ was evaluated in a Kinase Glo based enzyme activity assay using human recombinant enzymes. The assay measures depletion of ATP after incubation with enzyme, PIP2 and ATP plus compound. ATP at the end of the reaction is detected by addition of Kinase Glo reagent, in this the Ultra Glo™ luciferase (Promega) uses the ATP as a substrate to catalyze the mono-oxygenation of luciferin and the generation of light. A direct relationship exists between the luminescence measured with the Kinase-Glo Plus Reagent and the amount of ATP remaining in a completed kinase reaction and luminescence is inversely related to kinase activity. Twelve different compound concentrations were tested and raw data from the inhibition of PI3Kβ, PI3Kα, PI3Kγ and PI3Kδ was plotted versus inhibitor concentration.

Method Details:

Compounds in 100% DMSO were added to assay plates by acoustic dispensing. PI3β was added in a Tris buffer (50 mM Tris pH7.4, 0.05% CHAPS, 2.1 mM DTT, and 10 mM $MgCl_2$) and allowed to preincubate with compound for 20 min prior to addition of substrate solution containing PIP2 and ATP. The enzyme reaction was stopped after 80 min by the addition of Kinase Glo detection solution. Plates were left for 30 min at room temperature then read on a Pherastar Instrument (Luminescence ATP 384 program) setting gain on max well. The final concentration of DMSO, ATP and PIP2 in the assay were, 1%, 8 µM, and 80 µM respectively.

Data Analysis:

$IC_{50}$ values were calculated using a log curve fitting to a non-linear regression package, fitting raw data to inhibitor concentration. The $IC_{50}$ value is the concentration of test compound that inhibited 50% of enzyme activity.

(b) Protocol for Detection of Phospho AKT (ser473) in MDA-MB-468 Cells

MDA-MB-468 cells (human breast adenocarcinoma ATCC HTB 132) are seeded into Greiner 384 well black flat-bottomed plates by automated cell culture robot (Selec T). Cells can also be maintained manually and seeded into plates using multidrop or Wellmate. Cells seeded at 1500 cell/well in 40 µl of DMEN containing 10% FCS and 1% glutamine. Cell plates are incubated for 18 hours in a 37° C. incubator.

Compounds are dosed onto cells using an Echo acoustic dispenser, which dispenses nl quantities of compound or DMSO. Compounds are dosed in a 12 point concentration range from 30 µM top dose, 28 compounds are dosed on one plate. There are 17 DMSO only positive control wells per plate, and 16 negative control well which have been dosed with a concentration of reference compound that will knockout the pAKT signal.

Plates are incubated at 37° C. for 2 hours, cells are the fixed by the addition of 10 µl of a 3.7% Formaldehyde solution in a fume cupboard using a Wellmate.

After 30 min to allow for fixation, the fixative and media are removed and the plates washed with Proclin PBS/A using Tecan PW384 plate washer in a fume cupboard. Wells are blocked and permeabilised with the addition of 40 µl of PBS containing 0.5% Tween20 and 1% marvel using a Wellmate and incubated for 60 min at room temperature.

Permeabilisation and blocking buffer removed using Tecan PW384 plate washer, then 20 µl primary antibody solution added using a Wellmate. The primary antibody solution is a 1:500 dilution of Rabbit anti-phospho AKT Ser 473 (Cell signalling technologies catalogue number #3787) in PBS/T containing 1% marvel (dried milk powder) and incubated overnight at 4° C.

Plates are washed using a Tecan PW384 plate washer three times with Phosphate Buffered Saline+0.05% (v/v) Polysorbate20 and Proclin300 (Supelco). 20 µl of secondary antibody solution is then added to each well using a Wellmate and incubated for 1 hour at Room Temp. The secondary antibody solution is a 1:1000 dilution of Alexa Fluor 488 anti-Rabbit (Molecular Probes cat no A11008) diluted in Phosphate Buffered Saline+0.05% (v/v) Polysorbate20 containing 1% marvel. Plates are washed three times as before then 200 PBS added to each well and plates sealed with black plate sealer.

The plates are read on an Acumen reader as soon as possible. Using this system $IC_{50}$ values can be generated and quality of plates determined by control wells. Reference compounds are run each time to monitor assay performance.

(c) Protocol for Detection of Phospho AKT (ser473) in Swiss Athymic Nu/Nu Mice

Swiss athymic nu/nu mice can be transplanted s.c with human prostatic adenocarcinoma cell line PC3 (ATCC CRL1435) to determine anti-tumour activity of PI3 kinase inhibitors. On day 0, once $10^6$ cells in 50% Matrigel™ (BD Biosciences #354234) are injected s.c. on the left flank of the animals. Animals are randomised into required group sizes (typically 5 per treatment group) when tumours reach a volume of ~400-600 mm³ and treatment commences. Tumours are taken at termination and flash frozen in liquid nitrogen and stored at −80° C. until analysis. 1 ml of lysis buffer plus phosphatase inhibitors Sigma #P2850, Sigma #P5726 (diluted 1:100) and protease inhibitors Sigma #P8340 (diluted 1:200) is added to each tumour in a Fastprep tube. The tumours are homogenised for 1 minute on the Fastprep machine and then left on ice for 10 min.

Samples are spun for 10 min at 13,000 rpm in a chilled centrifuge. Cleared lysates are then taken into fresh tubes and 5 µl used for a protein determination assay. All tumour samples are diluted to same concentration so that 15 µg is run per lane on a 4-15% NuPAGE Bis-Tris gels (Invitrogen) for 90 min at 140 Volts. The samples are randomised so that gel effects are minimised. After blotting onto Nitrocellulose membranes they are blocked for one hour then incubated overnight with a 1:500 dilution of antibody to either total AKT (CST #9272) or phospho AKT-ser 473 (CST #9271). Blots are washed three times in PBST before incubation for one hour at room temperature with a 1:2,000 dilution of anti-rabbit secondary HRP-linked antibody (CST #7074). Block and antibody incubation buffer is 5% dried milk powder in PBS with 0.05% Polysorbate.

Blots are washed three times in PBS/T then visualised using Pierce West Dura ECL kit and the ChemiGenius. Bands are quantified and a ratio of phospho to total signal is obtained for each sample. The controls are averaged and each treatment sample is normalised to the averaged control value.

(d) Protocol for Detection of Tumour Growth Inhibition in Human Prostatic Adenocarcinoma Cell Line PC3 Transplanted Swiss Athymic Nu/Nu Mice Swiss athymic nu/nu mice can be transplanted s.c with the human prostatic adenocarcinoma cell line PC3 (ATCC CRL1435) to determine anti-tumour activity of PI3 kinase inhibitors. On day 0, once $10^6$ cells in 50% Matrigel (BDM) are injected s.c. on the left flank of the animals. Animals are randomised into groups of 10-15 when tumours reach a volume of ~200-300 mm³ and treatment commences. Animals are dosed for 2-4 weeks by peroral, intravenous or intraperitoneal routes with compound (and optionally a cyp inhibitor such as 1-aminobenzotriazole) in a suitable vehicle at defined doses. Tumours are usually measured twice weekly by caliper and volume of tumours calculated using elliptical formula (pi/6×width×width×length).

(e) Protocol for Detection of Phospho AKT (ser473) in Jeko Cells

Compounds at ×10 final concentration in 10 µl of 1% (v/v) DMSO are added to the wells of a Greiner V-bottomed 96 well plate. Compounds are dosed in a 10-point concentration range from 1 µM top dose, 8 compounds are dosed on one plate. There are 8 DMSO positive control wells per plate which have been dosed with vehicle and anti-IgM, and 8 negative control wells which have been dosed with vehicle and assay buffer. Final vehicle concentration is 0.1% DMSO. A reference PI3Kδ selective compound is included in each run. Jeko B cells (human mantle cell lymphoma, ATCC CRL-3006) are seeded into the Greiner 96 well V-bottomed plates containing compounds. Cells are seeded at 100,000 cell/well in 70 µl of RPMI containing 1% glutamine.

Cell plates are incubated for 1 hour in a 37° C. incubator. After this compound pre-incubation time, anti-IgM (F(ab')2 fragment goat anti-human IgM, Stratech 109-006-129) is added to the plates at ×5 final concentration in 20 µl of assay buffer (RPMI containing 1% glutamine). Final anti-IgM concentration is 0.06 µg/ml or an equivalent EC90 dose. Plates are incubated at 37° C. for 10 min, subsequently plates are immediately placed on ice and centrifuged at 12000 rpm for 4 min. On ice, supernatants are carefully removed with a manual pipette and 40 µl lysis buffer added. Plates are incubated on ice for 5 min and stored at −80° C. until assayed in the phosphor (ser473)/Total Akt whole cell lysate kit according to manufacturer's instructions (Mesoscale Diagnostics, K11100D-3).

Although the pharmacological properties of the compounds of the Formula I vary with structural change as expected, in general activity possessed by compounds of the Formula I may be demonstrated at the following concentrations or doses in one or more of the above tests (a) and (b):—
- Test (a):—$IC_{50}$ versus PI3Kβ in the range, for example, 1 nM-25 μM;
- Test (a):—$IC_{50}$ versus PI3Kδ in the range, for example, 1 nM-25 μM;
- Test (b):—$IC_{50}$ versus cellular phospho AKT (ser473) in MDA-MB-468 cells, in the range, for example, 1 nM-25 μM;
- Test (e):—$IC_{50}$ versus cellular phospho AKT (ser473) in Jeko cells, in the range, for example, 1 nM-25 μM;

Conveniently, particular compounds of the invention possess activity at the following concentrations or doses in one or more of the above tests (a) and (b):—
- Test (a):—$IC_{50}$ versus PI3Kβ in the range, for example, 1 nM-10 μM;
- Test (a):—$IC_{50}$ versus PI3Kδ in the range, for example, 1 nM-10 μM;
- Test (b):—$IC_{50}$ versus cellular phospho AKT (ser473) in MDA-MB-468 cells, in the range, for example, 1 nM-20 μM;
- Test (e):—$IC_{50}$ versus cellular phospho AKT (ser473) in Jeko cells, in the range, for example, 1 nM-20 μM;

Conveniently, particular compounds of the invention possess activity at the following concentrations or doses in one or more of the above tests (a), (b), (c) and (d):—
- Test (a):—$IC_{50}$ versus PI3Kβ in the range, for example, 1 nM-10 μM;
- Test (a):—$IC_{50}$ versus PI3Kδ in the range, for example, 1 nM-10 μM;
- Test (b):—$IC_{50}$ versus cellular phospho AKT (ser473) in MDA-MB-468 cells, in the range, for example, 1 nM-20 μM;
- Test (c):—>50% inhibition of in vivo phospho AKT (ser473) in the range, for example, 1-200 mg/kg/day;
- Test (d):—xenograft activity in the range, for example, 1-200 mg/kg/day.
- Test (e):—$IC_{50}$ versus cellular phospho AKT (ser473) in Jeko cells, in the range, for example, 1 nM-20 μM;

For example, the chromenone compound disclosed as Example 1.04 possesses activity in Test (a) with an $IC_{50}$ versus PI3Kβ of approximately 11 nM; in Test (a) with an $IC_{50}$ versus PI3Kδ of approximately 24 nM; and activity in Test (b) with an $IC_{50}$ versus cellular cellular phospho AKT (ser473) in MDA-MB-468 cells of approximately 5 nM.

For example, the chromenone compound disclosed as Example 2.00 possesses activity in Test (a) with an $IC_{50}$ versus PI3Kβ of approximately 9 nM; in Test (a) with an $IC_{50}$ versus PI3Kδ of approximately 12 nM; and activity in Test (b) with an $IC_{50}$ versus cellular cellular phospho AKT (ser473) in MDA-MB-468 cells of approximately 2 nM.

For example, the chromenone compound disclosed as Example 1.03b possesses activity in Test (a) with an $IC_{50}$ versus PI3Kβ of approximately 7 nM; in Test (a) with an $IC_{50}$ versus PI3Kδ of approximately 9 nM; and activity in Test (b) with an $IC_{50}$ versus cellular cellular phospho AKT (ser473) in MDA-MB-468 cells of approximately 1 nM; and activity in Test (e) with an $IC_{50}$ versus cellular cellular phospho AKT (ser473) in Jeko cells of approximately 7 nM.

For example, the chromenone compound disclosed as Example 1.03 possesses activity in Test (a) with an $IC_{50}$ versus PI3Kβ of approximately 12 nM; in Test (a) with an $IC_{50}$ versus PI3Kδ of approximately 22 nM; and activity in Test (b) with an $IC_{50}$ versus cellular cellular phospho AKT (ser473) in MDA-MB-468 cells of approximately 2 nM.

For example, the chromenone compound disclosed as Example 1.03a possesses activity in Test (a) with an $IC_{50}$ versus PI3Kβ of approximately 0.198 μM; in Test (a) with an $IC_{50}$ versus PI3Kδ of approximately 0.282 μM; and activity in Test (b) with an $IC_{50}$ versus cellular cellular phospho AKT (ser473) in MDA-MB-468 cells of approximately 27 nM.

For example, the chromenone compound disclosed as Example 1.05 possesses activity in Test (a) with an $IC_{50}$ versus PI3Kβ of approximately 7 nM; in Test (a) with an $IC_{50}$ versus PI3Kδ of approximately 9 nM; and activity in Test (b) with an $IC_{50}$ versus cellular cellular phospho AKT (ser473) in MDA-MB-468 cells of approximately 1 nM.

For example, the chromenone compound disclosed as Example 1.06 possesses activity in Test (a) with an $IC_{50}$ versus PI3Kβ of approximately 7 nM; in Test (a) with an $IC_{50}$ versus PI3Kδ of approximately 7 nM; and activity in Test (b) with an $IC_{50}$ versus cellular cellular phospho AKT (ser473) in MDA-MB-468 cells of approximately 1 nM.

For example, the chromenone compound disclosed as Example 1.07 possesses activity in Test (a) with an $IC_{50}$ versus PI3Kβ of approximately 6 nM; in Test (a) with an $IC_{50}$ versus PI3Kδ of approximately 5 nM; and activity in Test (b) with an $IC_{50}$ versus cellular cellular phospho AKT (ser473) in MDA-MB-468 cells of approximately 2 nM.

For example, the chromenone compound disclosed as Example 1.08 possesses activity in Test (a) with an $IC_{50}$ versus PI3Kβ of approximately 6 nM; in Test (a) with an $IC_{50}$ versus PI3Kδ of approximately 6 nM; and activity in Test (b) with an $IC_{50}$ versus cellular cellular phospho AKT (ser473) in MDA-MB-468 cells of approximately 2 nM.

For example, the chromenone compound disclosed as Example 1.10 possesses activity in Test (a) with an $IC_{50}$ versus PI3Kβ of approximately 8 nM; in Test (a) with an $IC_{50}$ versus PI3Kδ of approximately 21 nM; and activity in Test (b) with an $IC_{50}$ versus cellular cellular phospho AKT (ser473) in MDA-MB-468 cells of approximately 4 nM.

For example, the chromenone compound disclosed as Example 1.11 possesses activity in Test (a) with an $IC_{50}$ versus PI3Kβ of approximately 9 nM; in Test (a) with an $IC_{50}$ versus PI3Kδ of approximately 15 nM; and activity in Test (b) with an $IC_{50}$ versus cellular cellular phospho AKT (ser473) in MDA-MB-468 cells of approximately 8 nM.

For example, the chromenone compound disclosed as Example 3.00 possesses activity in Test (a) with an $IC_{50}$ versus PI3Kβ of approximately 11 nM; in Test (a) with an $IC_{50}$ versus PI3Kδ of approximately 18 nM; and activity in Test (b) with an $IC_{50}$ versus cellular cellular phospho AKT (ser473) in MDA-MB-468 cells of approximately 3 nM.

For example, the chromenone compound disclosed as Example 3.02 possesses activity in Test (a) with an $IC_{50}$ versus PI3Kβ of approximately 14 nM; in Test (a) with an $IC_{50}$ versus PI3Kδ of approximately 10 nM; and activity in Test (b) with an $IC_{50}$ versus cellular cellular phospho AKT (ser473) in MDA-MB-468 cells of approximately 3 nM.

For example, the chromenone compound disclosed as Example 3.03 possesses activity in Test (a) with an $IC_{50}$ versus PI3Kβ of approximately 10 nM; in Test (a) with an $IC_{50}$ versus PI3Kδ of approximately 7 nM; and activity in Test (b) with an $IC_{50}$ versus cellular cellular phospho AKT (ser473) in MDA-MB-468 cells of approximately 1 nM.

For example, the chromenone compounds disclosed within the Examples possess activity in Test (a) at the levels illustrated in Table A.

TABLE A

| Example number | PI3Kβ inhibition, IC$_{50}$ (μM) | PI3Kδ inhibition, IC$_{50}$ (μM) |
| --- | --- | --- |
| 1.00 | 0.013 | 0.015 |
| 1.01 | 0.016 | 0.016 |
| 1.02 | 0.015 | 0.014 |
| 1.03 | 0.012 | 0.022 |
| 1.03a | 0.198 | 0.282 |
| 1.03b | 0.007 | 0.009 |
| 1.04 | 0.011 | 0.024 |
| 1.05 | 0.007 | 0.009 |
| 1.06 | 0.007 | 0.007 |
| 1.07 | 0.006 | 0.005 |
| 1.08 | 0.006 | 0.006 |
| 1.09 | 0.007 | 0.014 |
| 1.10 | 0.008 | 0.021 |
| 1.11 | 0.009 | 0.015 |
| 1.12 | 0.015 | 0.032 |
| 1.12a | 0.939 | 1.722 |
| 1.12b | 0.005 | 0.013 |
| 2.00 | 0.009 | 0.012 |
| 2.01 | 0.010 | 0.015 |
| 2.02 | 0.013 | 0.016 |
| 2.03 | 0.013 | 0.014 |
| 2.04 | 0.017 | 0.019 |
| 2.04a | 1.761 | 2.478 |
| 2.04b | 0.007 | 0.008 |
| 3.00 | 0.011 | 0.018 |
| 3.01 | 0.014* | 0.015 |
| 3.02 | 0.014 | 0.010 |
| 3.03 | 0.010 | 0.007 |

*the compound disclosed in Example 3.01 had an activity in Test (b) with an IC$_{50}$ versus cellular phospho AKT (ser473) in MDA-MB-468 cells of approximately 6 nM.

According to a further aspect of the invention there is provided a pharmaceutical composition, which comprises a chromenone derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intraperitoneal or intramuscular dosing) or as a suppository for rectal dosing.

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent (more suitably from 1 to 250 mg, for example from 1 to 100 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the disease state, the age and sex of the animal or patient and the route of administration, according to well known principles of medicine.

In using a compound of the Formula I for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form. Typically, unit dosage forms will contain about 10 mg to 0.5 g of a compound of this invention.

As stated above, it is known that PI 3-kinase enzymes contribute to tumourigenesis by one or more of the effects of mediating proliferation of cancer and other cells, mediating angiogenic events and mediating the motility, migration and invasiveness of cancer cells. We have found that the chromenone compounds of the present invention possess potent anti-tumour activity which it is believed is obtained by way of inhibition of one or more of the Class I PI 3-kinase enzymes (such as the Class Ia PI 3-kinase enzymes and/or the Class Ib PI 3-kinase enzyme) that are involved in the signal transduction steps which lead to the proliferation and survival of tumour cells and the invasiveness and migratory ability of metastasising tumour cells.

Accordingly, the compounds of the present invention are of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the chromenone compounds of the present invention are of value as anti-proliferative and anti-invasive agents in the containment and/or treatment of solid tumour disease. Particularly, the compounds of the present invention are expected to be useful in the prevention or treatment of those tumours which are sensitive to inhibition of one or more of the multiple PI 3-kinase enzymes such as the Class Ia PI 3-kinase enzymes and the Class Ib PI 3-kinase enzyme that are involved in the signal transduction steps which lead to the proliferation and survival of tumour cells and the migratory ability and invasiveness of metastasising tumour cells. Further, the compounds of the present invention are expected to be useful in the prevention or treatment of those tumours which are mediated alone or in part by inhibition of PI 3-kinase enzymes such as the Class Ia PI 3-kinase enzymes and the Class Ib PI 3-kinase enzyme, i.e. the compounds may be used to produce a PI 3-kinase enzyme inhibitory effect in a warm blooded animal in need of such treatment.

As stated hereinbefore, inhibitors of PI 3-kinase enzymes should be of therapeutic value for treatment of the various forms of the disease of cancer comprising solid tumours such as carcinomas and sarcomas and the leukaemias and lymphoid malignancies. In particular, inhibitors of Class I PI 3-kinase enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, brain, head and neck, kidney, liver, gastrointestinal tissue, oesophagus, ovary, pancreas, skin, testes, thyroid, uterus, cervix and vulva, and of leukaemias (including ALL, CLL and CML), multiple myeloma and lymphomas (including non-Hodgkin's lymphomas such as diffuse large B-cell lymphoma [DLBCL], follicular lymphoma, and mantle cell lymphoma).

According to a further aspect of the invention there is provided a chromenone derivative of the Formula I, or a pharmaceutically acceptable salt thereof, as defined hereinbefore for use as a medicament in a warm-blooded animal such as man.

According to a further aspect of the invention, there is provided a chromenone derivative of the Formula I, or a pharmaceutically acceptable salt thereof, as defined hereinbefore for use in the production of an anti-proliferative effect in a warm-blooded animal such as man.

According to a further feature of this aspect of the invention there is provided a chromenone derivative of the Formula I, or a pharmaceutically acceptable salt thereof, as defined hereinbefore for use in a warm-blooded animal such as man as an anti-invasive agent in the containment and/or treatment of solid tumour disease.

According to a further aspect of the invention, there is provided the use of a chromenone derivative of the Formula I, or a pharmaceutically acceptable salt thereof, as defined hereinbefore for the production of an anti-proliferative effect in a warm-blooded animal such as man.

According to a further feature of this aspect of the invention there is provided the use of a chromenone derivative of the Formula I, or a pharmaceutically acceptable salt thereof, as defined hereinbefore in the manufacture of a medicament for use in the production of an anti-proliferative effect in a warm-blooded animal such as man.

According to a further feature of this aspect of the invention there is provided the use of a chromenone derivative of the Formula I, or a pharmaceutically acceptable salt thereof, as defined hereinbefore in the manufacture of a medicament for use in a warm-blooded animal such as man as an anti-invasive agent in the containment and/or treatment of solid tumour disease.

According to a further feature of this aspect of the invention there is provided a method for producing an anti-proliferative effect in a warm blooded animal, such as man, in need of such treatment which comprises administering to said animal an effective amount of a chromenone derivative of the Formula I, or a pharmaceutically acceptable salt thereof, as defined hereinbefore.

According to a further feature of this aspect of the invention there is provided a method for producing an anti-invasive effect by the containment and/or treatment of solid tumour disease in a warm blooded animal, such as man, in need of such treatment which comprises administering to said animal an effective amount of a chromenone derivative of the Formula I, or a pharmaceutically acceptable salt thereof, solvate or pro-drug, as defined hereinbefore.

According to a further aspect of the invention, there is provided a chromenone derivative of the Formula I, or a pharmaceutically acceptable salt thereof, as defined hereinbefore for use in the prevention or treatment of cancer in a warm blooded animal such as man.

According to a further aspect of the invention there is provided the use of a chromenone e derivative of the Formula I, or a pharmaceutically acceptable salt thereof, as defined hereinbefore in the manufacture of a medicament for use in the prevention or treatment of cancer in a warm blooded animal such as man.

According to a further feature of this aspect of the invention there is provided a method for the prevention or treatment of cancer in a warm blooded animal, such as man, in need of such treatment which comprises administering to said animal an effective amount of a chromenone derivative of the Formula I, or a pharmaceutically acceptable salt thereof, as defined hereinbefore.

According to a further aspect of the invention there is provided the use of a chromenone e derivative of the Formula I, or a pharmaceutically acceptable salt thereof, as defined hereinbefore in the manufacture of a medicament for use in the prevention or treatment of solid tumour disease in a warm blooded animal such as man.

According to a further feature of this aspect of the invention there is provided a method for the prevention or treatment of solid tumour disease in a warm blooded animal, such as man, in need of such treatment which comprises administering to said animal an effective amount of a chromenone derivative of the Formula I, or a pharmaceutically acceptable salt thereof, as defined hereinbefore.

According to a further aspect of the invention there is provided a chromenone derivative of the Formula I, or a pharmaceutically acceptable salt thereof, as defined hereinbefore for use in the prevention or treatment of those tumours which are sensitive to inhibition of PI 3-kinase enzymes (such as the Class Ia enzymes and/or the Class Ib PI 3-kinase enzyme) that are involved in the signal transduction steps which lead to the proliferation, survival, invasiveness and migratory ability of tumour cells.

According to a further feature of this aspect of the invention there is provided the use of a chromenone derivative of the Formula I, or a pharmaceutically acceptable salt thereof, as defined hereinbefore in the manufacture of a medicament for use in the prevention or treatment of those tumours which are sensitive to inhibition of PI 3-kinase enzymes (such as the Class Ia enzymes and/or the Class Ib PI 3-kinase enzyme) that are involved in the signal transduction steps which lead to the proliferation, survival, invasiveness and migratory ability of tumour cells.

According to a further feature of this aspect of the invention there is provided a method for the prevention or treatment of those tumours which are sensitive to inhibition of PI 3-kinase enzymes (such as the Class Ia enzymes and/or the Class Ib PI 3-kinase enzyme) that are involved in the signal transduction steps which lead to the proliferation, survival, invasiveness and migratory ability of tumour cells which comprises administering to said animal an effective amount of a chromenone derivative of the Formula I, or a pharmaceutically acceptable salt thereof, as defined hereinbefore.

According to a further aspect of the invention there is provided a chromenone derivative of the Formula I, or a pharmaceutically acceptable salt thereof, as defined hereinbefore for use in providing a PI 3-kinase enzyme inhibitory effect (such as a Class Ia PI 3-kinase enzyme or Class Ib PI 3-kinase enzyme inhibitory effect).

According to a further feature of this aspect of the invention there is provided the use of a chromenone derivative of the Formula I, or a pharmaceutically acceptable salt thereof, as defined hereinbefore in the manufacture of a medicament for use in providing a PI 3-kinase enzyme inhibitory effect (such as a Class Ia PI 3-kinase enzyme or Class Ib PI 3-kinase enzyme inhibitory effect).

According to a further aspect of the invention there is also provided a method for providing a PI 3-kinase enzyme inhibitory effect (such as a Class Ia PI 3-kinase enzyme or Class Ib PI 3-kinase enzyme inhibitory effect) which comprises administering an effective amount of a chromenone derivative of the Formula I, or a pharmaceutically acceptable salt thereof, as defined hereinbefore.

As stated hereinbefore, certain compounds of the present invention, possess substantially better potency against Class Ia PI 3-kinase enzymes than against the Class Ib PI 3-kinase enzyme or against EGF receptor tyrosine kinase, VEGF receptor tyrosine kinase or Src non-receptor tyrosine kinase enzymes. Such compounds possess sufficient potency against Class Ia PI 3-kinase enzymes that they may be used in an amount sufficient to inhibit Class Ia PI 3-kinase enzymes whilst demonstrating little activity against the Class Ib PI 3-kinase enzyme or against EGF receptor tyrosine kinase, VEGF receptor tyrosine kinase or Src non-receptor tyrosine kinase enzymes. Such compounds are likely to be useful for the selective inhibition of Class Ia PI 3-kinase enzymes and are likely to be useful for the effective treatment of, for example Class Ia PI 3-kinase enzyme driven tumours.

According to this aspect of the invention there is provided a chromenone derivative of the Formula I, or a pharmaceutically acceptable salt thereof, as defined hereinbefore for use in providing a selective Class Ia PI 3-kinase enzyme inhibitory effect.

According to a further feature of this aspect of the invention there is provided the use of a chromenone derivative of the Formula I, or a pharmaceutically acceptable salt thereof, as defined hereinbefore in the manufacture of a medicament for use in providing a selective Class Ia PI 3-kinase enzyme inhibitory effect.

According to a further aspect of the invention there is also provided a method for providing a selective Class Ia PI 3-kinase enzyme inhibitory effect which comprises administering an effective amount of a chromenone derivative of the Formula I, or a pharmaceutically acceptable salt thereof, as defined hereinbefore.

By "a selective Class Ia PI 3-kinase enzyme inhibitory effect" is meant that the chromenone compounds of the Formula I are more potent against Class Ia PI 3-kinase enzymes than against other kinase enzymes. In particular, some of the compounds according to the invention are more potent against Class Ia PI 3-kinase enzymes than against other kinases such as receptor or non-receptor tyrosine kinases or serine/threonine kinases. For example a selective Class Ia PI 3-kinase enzyme inhibitor according to the invention is at least 5 times more potent, conveniently at least 10 times more potent, more conveniently at least 100 times more potent, against Class Ia PI 3-kinase enzymes than against other kinases.

According to a further feature of the invention there is provided a chromenone derivative of the Formula I, or a pharmaceutically acceptable salt thereof, as defined hereinbefore for use in the treatment of cancer of the breast, colorectum, lung (including small cell lung cancer, non-small cell lung cancer and bronchioalveolar cancer) and prostate.

According to a further feature of this aspect of the invention there is provided a chromenone derivative of the Formula I, or a pharmaceutically acceptable salt thereof, as defined hereinbefore for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of this aspect of the invention there is provided a chromenone derivative of the Formula I, or a pharmaceutically acceptable salt thereof, as defined hereinbefore for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL, CLL and CML), multiple myeloma and lymphomas (including non-Hodgkin's lymphomas such as diffuse large B-cell lymphoma [DLBCL], follicular lymphoma, and mantle cell lymphoma).

According to a further feature of this aspect of the invention there is provided the use of a chromenone derivative of the Formula I, or a pharmaceutically acceptable salt thereof, as defined hereinbefore in the manufacture of a medicament for use in the treatment of cancer of the breast, colorectum, lung (including small cell lung cancer, non-small cell lung cancer and bronchioalveolar cancer) and prostate.

According to a further feature of this aspect of the invention there is provided the use of a chromenone derivative of the Formula I, or a pharmaceutically acceptable salt thereof, as defined hereinbefore in the manufacture of a medicament for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of this aspect of the invention there is provided the use of a chromenone derivative of the Formula I, or a pharmaceutically acceptable salt thereof, as defined hereinbefore in the manufacture of a medicament for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL, CLL and CML), multiple myeloma and lymphomas (including non-Hodgkin's lymphomas such as diffuse large B-cell lymphoma [DLBCL], follicular lymphoma, and mantle cell lymphoma).

According to a further feature of this aspect of the invention there is provided a method for treating cancer of the breast, colorectum, lung (including small cell lung cancer, non-small cell lung cancer and bronchioalveolar cancer) and prostate in a warm blooded animal such as man that is in need of such treatment which comprises administering an effective amount of a chromenone derivative of the Formula I, or a pharmaceutically acceptable salt thereof, as defined hereinbefore.

According to a further feature of this aspect of the invention there is provided a method for treating cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas in a warm blooded animal such as man that is in need of such treatment which comprises administering an effective amount of a chromenone derivative of the Formula I, or a pharmaceutically acceptable salt thereof, as defined hereinbefore.

According to a further feature of this aspect of the invention there is provided a method for treating cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL, CLL and CML), multiple myeloma and lymphomas (including non-Hodgkin's lymphomas such as diffuse large B-cell lymphoma [DLBCL], follicular lymphoma, and mantle cell lymphoma) in a warm blooded animal such as man that is in need of such treatment which comprises administering an effective amount of a chromenone derivative of the Formula I, or a pharmaceutically acceptable salt thereof, as defined hereinbefore.

As stated hereinbefore, the in vivo effects of a compound of the Formula I may be exerted in part by one or more metabolites that are formed within the human or animal body after administration of a compound of the Formula I.

As stated hereinbefore, particular compounds of the invention posses better potency against certain isoforms of the PI 3-kinase enzyme than others. For example, particular compounds of the invention possess better potency against PI 3-kinase β and PI 3-kinase δ than against other class I PI 3-kinase isoforms such as α and γ.

The present invention therefore also contemplates a method for inhibiting phosphoinositide 3-kinase β in a patient, comprising administering to a patient an amount of the compound of Formula I, or a pharmaceutically acceptable salt thereof, effective in inhibiting the phosphoinositide 3-kinase β in the patient.

Similarly, the present invention therefore also contemplates a method for inhibiting phosphoinositide 3-kinase δ in a patient, comprising administering to a patient an amount of the compound of Formula I, or a pharmaceutically acceptable salt thereof, effective in inhibiting the phosphoinositide 3-kinase δ in the patient.

The compound of Formula I, or a pharmaceutically acceptable salt thereof, being an inhibitor of PI 3-kinase, also has potential therapeutic uses in a variety of other disease states. For example, PI 3-kinase plays an important role in promoting smooth muscle proliferation in the vascular tree, i.e. vascular smooth muscle cells, Thyberg, 1998, *European Journal of Cell Biology* 76(1):33-42, and in the lungs (airway smooth muscle cells), Krymskaya, V. P., *BioDrugs*, 2007. 21(2): 85-95. Excessive proliferation of vascular smooth muscle cells plays an important role in the formation of atherosclerotic plaques and in the development of neointimal hyperplasia following invasive vascular procedures, Scwartz et al., 1984, *Progress in Cardiovascular Disease* 26:355-372; Clowes et al., 1978, *Laboratory Investigations* 39:141-150. Moreover, excessive proliferation of airway smooth muscle cells leads to the development of COPD in the setting of asthma and chronic bronchitis. Inhibitors of PI 3-kinase activity therefore may be used to prevent vascular restenosis, atherosclerosis, and COPD.

PI 3-kinases also play an important role in regulating tumor cells and in the propensity of these cells to undergo apoptosis growth (Sellers et al., 1999, *The Journal of Clinical Investigation* 104:1655-1661). Additionally, uncontrolled regulation of the PI 3-kinase lipid products PI(3,4,5)P$_3$ and PI(3,4)P$_2$ by the lipid phosphatase PTEN plays an important role in progression of a number of malignant tumors in humans (Leevers et al., 1999, *Current Opinion in Cell Biology* 11:219-225). A specific role for the phosphoinositide 3-kinase β (PI3Kβ) isoform has been described in these types of cancers (Jia S et al., 2008, *Nature* 454(7205):776-9; Wee et al., 2008, *PNAS* 105(35):13057-62). Therefore, the compound of Formula I, or a pharmaceutically acceptable salt thereof, being an inhibitor of PI 3-kinase, may be used to treat neoplasms in humans.

PI 3-kinase also plays an important role in leukocyte function (Fuller et al., 1999, *The Journal of Immunology* 162(11): 6337-6340; Eder et al., 1998, *The Journal of Biological Chemistry* 273(43):28025-31) and lymphocyte function (Vicente-Manzanares et al., 1999, *The Journal of Immunology* 163(7):4001-4012). For example, leukocyte adhesion to inflamed endothelium involves activation of endogenous leukocyte integrins by a PI 3-kinase-dependent signaling process. Furthermore, oxidative burst (Nishioka et al., 1998, *FEBS Letters* 441(1):63-66 and Condliffe, A. M., et al., *Blood*, 2005. 106(4):1432-40) and cytoskeletal reorganization (Kirsch et al., 1999, *Proceedings National Academy of Sciences USA* 96(11):6211-6216) in neutrophils appears to involve PI 3-kinase signaling. Neutrophil migration and directional movement are also dependent on PI 3-kinase activity (Camps, M., et al., *Nat Med*, 2005. 11(9): p. 936-43 and Sadhu, C., et al., *J Immunol*, 2003. 170(5): 2647-54). Thus, inhibitors of PI 3-kinase may be useful in reducing leukocyte adhesion and activation at sites of inflammation and therefore may be used to treat acute and/or chronic inflammatory disorders. PI 3-kinase also plays an important role in lymphocyte proliferation and activation, Fruman et al., 1999, *Science* 283 (5400): 393-397. Given the important role of lymphocytes in auto-immune diseases, an inhibitor of PI 3-kinase activity may be used in the treatment of such disorders.

The anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, bendamustine, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea and purine analogues such as fludarabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), the androgen receptor antagonists MDV3100 or ARN-509 which prevent nuclear translocation of the androgen receptor and its binding to either DNA or coactivator proteins, inhibitors of CYP17A1 such as abiraterone [ZYTIGA™], and mixed inhibitors of androgen receptor function and CYP17A1 such as TOK-001 (galeterone). LHRH antagonists or LHRH agonists (for example goserelin, leuprorelin and buserelin), progestogens (for example megestrol acetate), aromatase inhibitors (for example as anastrozole, letrozole, vorazole and exemestane), and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin $\alpha v \beta 3$ function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, approaches for T-cell enhancement including CTLA4 antibodies, and antibodies directed toward CD137, PD-1 or B7-H1, toll-receptor agonists; agonistic antibodies to CD40 such as SGN-40 (Dacetuzumab) or to the Tweak receptor such as PDL-192; agonistic antibodies to FAS; approaches using antibodies to tumor associated antigens, and antibodies that deplete target cell types (e.g. unconjugated anti-CD20 antibodies such as Rituximab, ofatumumab, Obinutuzumab, anti-CD 19 antibodies such as MEDI-551, anti-CD52 antibodies such as Alemtuzumab, anti-CD37 antibodies such as TRU-016, anti-CD22 antibodies such as Inotuzumab, radiolabeled anti-CD20 antibodies Bexxar and Zevalin, and anti-CD54 antibody Campath; immunotoxins such as moxetumumab pasudotox), approaches using anti-idiotypic antibodies, approaches that enhance Natural Killer cell function, and approaches that utilize antibody-toxin conjugates (e.g. anti-CD33 antibody Mylotarg). Immune modifiers such as Revlimid (Lenalidomide).

According to this aspect of the invention there is provided a combination suitable for use in the treatment of cancer comprising a compound of formula I as defined hereinbefore or a pharmaceutically acceptable salt thereof and any one of the anti tumour agents listed under (i)-(x) above.

Therefore in a further aspect of the invention there is provided a compound of Formula I or a pharmaceutically acceptable salt thereof in combination with an anti-tumour agent selected from one listed under (i)-(x) herein above.

In a further aspect of the invention there is provided a combination suitable for use in the treatment of cancer comprising a compound of formula I as defined hereinbefore or a pharmaceutically acceptable salt thereof and any one of the anti tumour agents listed under (i) above.

In a further aspect of the invention there is provided a combination suitable for use in the treatment of cancer comprising a compound of formula I as defined hereinbefore or a pharmaceutically acceptable salt thereof and a taxoid, such as for example taxol or taxotere, conveniently taxotere.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of Formula I or a pharmaceutically acceptable salt thereof in combination with an anti-tumour agent selected from one listed under (i)-(x) herein above, in association with a pharmaceutically acceptable diluent or carrier.

According to a further aspect of the invention there is provided a pharmaceutical composition which comprises a compound of Formula I or a pharmaceutically acceptable salt thereof in combination with an anti-tumour agent selected from one listed under (i)-(x) herein above, in association with a pharmaceutically acceptable diluent or carrier for use in treating cancer.

According to another feature of the invention there is provided the use of a compound of the Formula I or a pharmaceutically acceptable salt thereof in combination with an anti-tumour agent selected from one listed under (i)-(x) herein above, in the manufacture of a medicament for use in cancer in a warm-blooded animal, such as man.

Therefore in an additional feature of the invention, there is provided a method of treating cancer in a warm-blooded animal, such as man, in need of such treatment which comprises administering to said animal an effective amount of a compound of Formula I or a pharmaceutically acceptable salt thereof in combination with an anti-tumour agent selected from one listed under (i)-(x) herein above.

According to a further aspect of the present invention there is provided a kit comprising a compound of Formula I or a pharmaceutically acceptable salt thereof in combination with an anti-tumour agent selected from one listed under (i)-(x) herein above.

According to a further aspect of the present invention there is provided a kit comprising:
a) a compound of Formula I or a pharmaceutically acceptable salt thereof in a first unit dosage form;
b) an anti-tumour agent selected from one listed under (i)-(x) herein above; in a second unit dosage form; and c) container means for containing said first and second dosage forms.

Although the compounds of the Formula I are primarily of value as therapeutic agents for use in warm-blooded animals (including man), they are also useful whenever it required to inhibit the effects of Class I PI 3-kinase enzyme, particularly a Class Ia PI 3-kinase enzymes and/or Class Ib PI 3-kinase enzyme, more particularly a Class Ia PI 3-kinase enzymes, which includes PI 3-kinase β. Thus, they are useful as pharmacological standards for use in the development of new biological tests and in the search for new pharmacological agents.

Reference is made in this specification to the following Figures:

Figure 1:
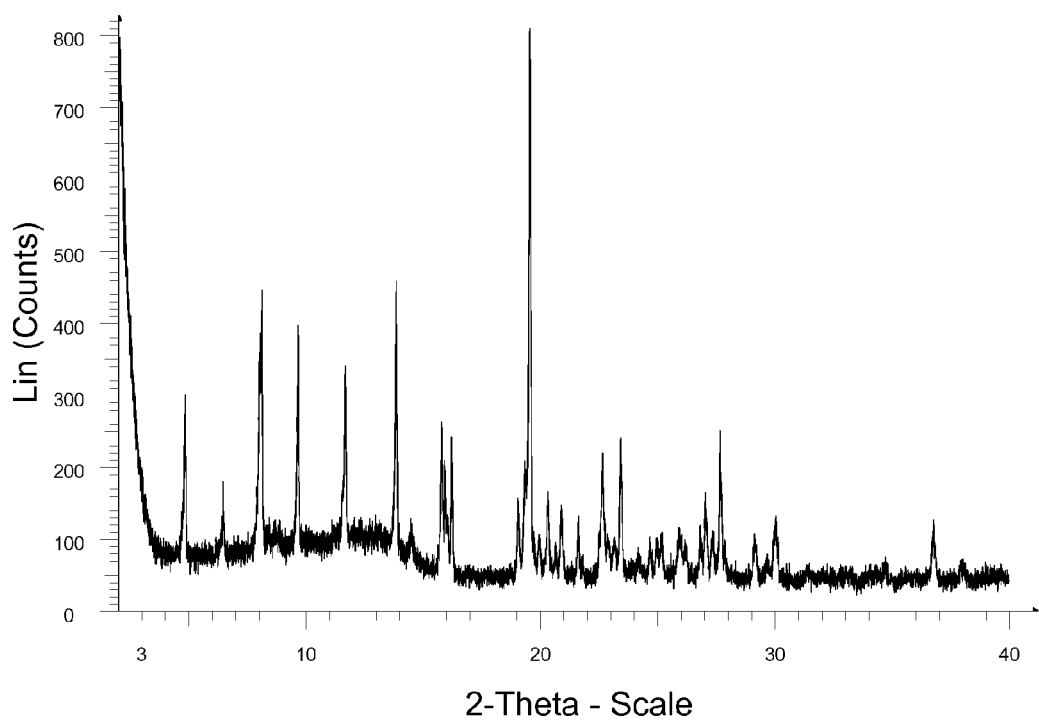
FIG. 1: X-Ray Powder Diffraction Pattern of Example 1.03b Form A

The invention will now be illustrated in the following Examples in which, generally:

(i) operations were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment in vacuo and work-up procedures were carried out after removal of residual solids by filtration;

(iii) Flash chromatography purifications were performed on an automated Armen Glider Flash: Spot II Ultimate (Armen Instrument, Saint-Ave, France) using prepacked Merck normal phase Si60 silica cartridges (granulometry: 15-40 or 40-63 μm) obtained from Merck, Darmstad, Germany.

(iv) preparative chromatography was performed on a Waters instrument (600/2700 or 2525) fitted with a ZMD or ZQ ESCi mass spectrometers and a Waters X-Terra or a Waters X-Bridge or a Waters SunFire reverse-phase column (C-18, 5 microns silica, 19 mm diameter, 100 mm length, flow rate of 40 mL/minute) using decreasingly polar mixtures of water (containing 0.2% ammonium carbonate) and acetonitrile as eluent;

(v) yields, where present, are not necessarily the maximum attainable;

(vi) in general, the structures of end-products of the Formula I were confirmed by nuclear magnetic resonance (NMR) spectroscopy; NMR chemical shift values were measured on the delta scale [proton magnetic resonance spectra were determined using a Bruker Avance 500 (500 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;

(vii) in general, end-products of the Formula I were also characterised by mass spectroscopy following liquid chromatography (LCMS); LCMS was carried out using an Waters Alliance HT (2790 & 2795) fitted with a Waters ZQ ESCi or ZMD ESCi mass spectrometer and an X Bridge 5 μm C-18 column (2.1×50 mm) at a flow rate of 2.4 mL/min, using a solvent system of 95% A+5% C to 95% B+5% C over 4 min, where A=water, B=methanol, C=1:1 methanol:water (containing 0.2% ammonium carbonate);

(viii) intermediates were not generally fully characterised and purity was assessed by thin layer chromatographic, mass spectral, HPLC and/or NMR analysis;

(ix) X-ray powder diffraction spectra were determined using a Bruker D4 instrument, by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms. The collimated X-ray source was passed through an automatic variable divergence slit set at V20 and the reflected radiation directed through a 5.89 mm antiscatter slit and a 9.55 mm detector slit. The sample was exposed for 0.03 seconds per 0.00570° 2-theta increment (continuous scan mode) over the range 2 degrees to 40 degrees 2-theta in theta-theta mode. The running time was 3 minutes and 36 seconds. The instrument was equipped with a Position sensitive detector (Lynxeye). Control and data capture was by means of a Dell Optiplex 686 NT 4.0 Workstation operating with Diffrac+ software. Persons skilled in the art of X-ray powder diffraction will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

(x) Differential Scanning calorimetry was performed using a TA Instruments Q1000 DSC instrument. Typically less than 5 mg of material contained in a standard aluminium pan fitted with a lid was heated over the temperature range 25° C. to 300° C. at a constant heating rate of 10° C. per minute. A purge gas using nitrogen was used at a flow rate of 50 mL per minute; and (xi) Single Crystal X-Ray Diffraction analysis was collected at 200 K using a Bruker APEX-II CCD diffractometer with graphite-monochromated MoKα radiation ($\lambda=0.71073$ Å). The structure was solved by direct methods and refined with $F^2$ against all reflections. Geometry: Bond distances, angles etc. have been calculated using the rounded fractional coordinates. All su's are estimated from the variances of the (full) variance-covariance matrix. The cell esds are taken into account in the estimation of distances, angles and torsion angles. Refinement: Refinement of $F^2$ against ALL reflections. The weighted R-factor wR and goodness of fit S are based on $F^2$, conventional Rfactors R are based on F, with F set to zero for negative $F^2$. The threshold expression of $F^2>2\sigma$ ($F^2$) is used only for calculating Rfactors(gt) etc. and is not relevant to the choice of reflections for refinement. R-factors based on $F^2$ are statistically about twice as large as those based on F, and R-factors based on ALL data will be even larger. Computer Programs: Data collection: Bruker APEX2; cell refinement: Bruker SAINT; data reduction: Bruker SAINT; program(s) used to solve structure: SHELXS97 (Sheldrick, 2008); program(s) used to refine structure: SHELXL97 (Sheldrick, 2008); molecular graphics: ORTEPII (Johnson, 1976), PLATON (Spek, 2007); software used to prepare material for publication: PLATON (Spek, 2007).

(xii) The following abbreviations have been used:—
aq. Aqueous
h hours
$CDCl_3$ deutero-chloroform
DCM dichloromethane
DIPEA N-ethyl-N-isopropylpropan-2-amine
DMF N,N-dimethylformamide DSC Differential Scanning calorimetry
DMA Dimethylacetamide
DMSO dimethyl sulphoxide
Ether diethyl ether
EtAc ethyl acetate
HCl hydrochloric acid
HPLC High performance liquid chromatography
MeCN acetonitrile
MeOH methanol
$MgSO_4$ magnesium sulphate
Min Minutes
MTBE methyl tert-butyl ether
TBME methyl tert-butyl ether
$NaHCO_3$ Sodium hydrogencarbonate
NaOH Sodium hydroxide
$NH_3$ Ammonia
NMP 1-methyl-2-pyrrolidone
$P_2O_5$ Phosphorus(V) oxide
r.t. room temperature
THF tetrahydrofuran
TEA triethyl amine
TFA Trifluoroacetic acid
TBTU 2-(1H-benzo[d][1,2,3]triazol-1-yl)-1,1,3,3-tetramethylisouronium tetrafluoroborate
TSTU 2-(2,5-dioxopyrrolidin-1-yl)-1,1,3,3-tetramethylisouronium tetrafluoroborate
HATU 2-(3H-[1,2,3]triazolo[4,5-b]pyridin-3-yl)-1,1,3,3-tetramethylisouronium hexafluorophosphate(V)

EXAMPLE 1.00

8-[1-(3,5-difluorophenyl)pyrrolidin-2-yl]-N,N-dimethyl-2-morpholino-4-oxo-4H-chromene-6-carboxamide

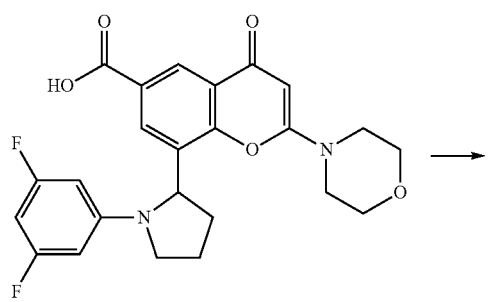

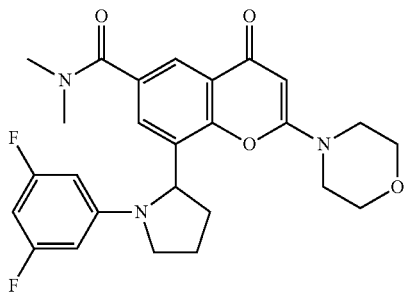

DIPEA (0.046 mL, 0.26 mmol) was added to a suspension of 8-(1-(3,5-difluorophenyl)pyrrolidin-2-yl)-2-morpholino-4-oxo-4H-chromene-6-carboxylic acid (60 mg, 0.13 mmol) in DMF (1 mL) followed by TSTU (43.5 mg, 0.14 mmol) at room temperature under nitrogen and stirred overnight. Dimethylamine (2N in THF) (0.131 mL, 0.26 mmol) was then added and the mixture was stirred for another hour. The reaction mixture was purified by preparative HPLC. The fractions were evaporated to dryness, the residue was taken up in a minimum of DCM, diluted with petroleum ether, stirred for 3 h, collected by filtration and dried to afford 8-(1-(3,5-difluorophenyl)pyrrolidin-2-yl)-N,N-dimethyl-2-morpholino-4-oxo-4H-chromene-6-carboxamide (43 mg, 68%) as a white solid.

Mass Spectrum: m/z [M+H]+=484.

Proton NMR Spectrum: (DMSO-d6) 1.75-1.88 (m, 1H), 1.97-2.09 (m, 2H), 2.45-2.57 (m partially hidden by DMSO-d5, 1H), 2.70 (s, 3H), 2.92 (s, 3H), 3.33-3.41 (m, 1H), 3.50-3.57 (m, 2H), 3.37-3.64 (m, 2H), 3.71-3.80 (m, 5H), 5.25 (d, 1H), 5.61 (s, 1H), 6.13 (d, 2H), 6.32 (t, 1H), 7.11 (d, 1H), 7.80 (d, 1H)

The 8-(1-(3,5-difluorophenyl)pyrrolidin-2-yl)-2-morpholino-4-oxo-4H-chromene-6-carboxylic acid used as starting material was made as follows:—

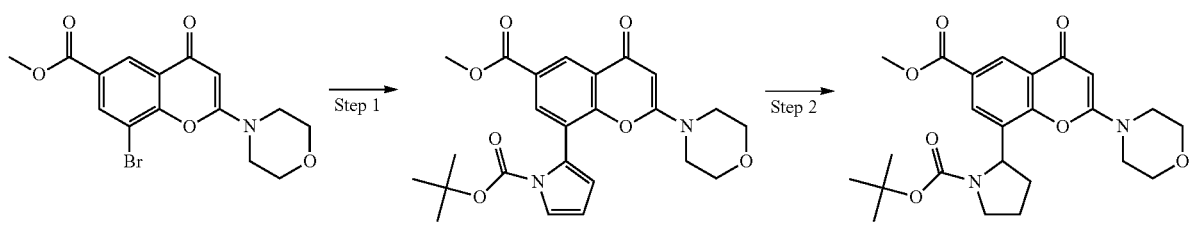

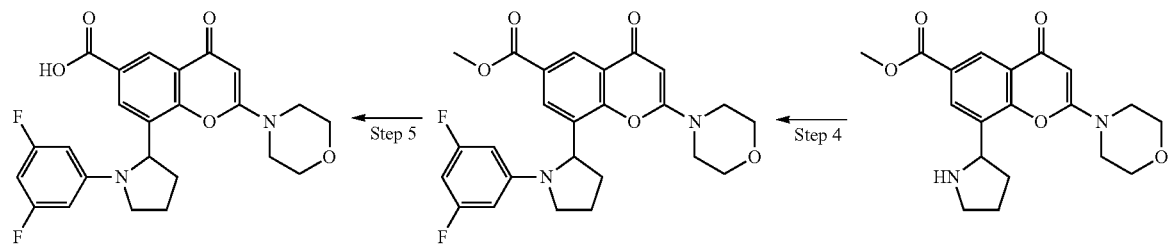

Step 1

To a stirred suspension of methyl 8-bromo-2-morpholino-4-oxo-4H-chromene-6-carboxylate (23 g, 62.47 mmol) in DME (300 mL) and water (30 mL) were added 1-(tert-butoxycarbonyl)-1H-pyrrol-2-ylboronic acid (14.50 g, 68.72 mmol), $Na_2CO_3$ (19.87 g, 187.41 mmol) and bis(triphenylphosphine)palladium(II) chloride (0.877 g, 1.25 mmol). The mixture was degassed with argon and heated to 80° C. for 7 h. Reaction was cooled down and concentrated, the residue was dissolved in 300 mL of DCM and 300 mL of water. The organic phase was decanted, washed with brine then dried over $MgSO_4$, filtered and concentrated to afford a crude compound which was purified on silica, eluting with 80% AcOEt in DCM. The solvents were evaporated to afford tert-butyl 2-(6-(methoxycarbonyl)-2-morpholino-4-oxo-4H-chromen-8-yl)-1H-pyrrole-1-carboxylate (20 g, 70%) as a white powder.

Mass Spectrum: m/z [M+H]+=455.

Step 2 tert-butyl 2-(6-(methoxycarbonyl)-2-morpholino-4-oxo-4H-chromen-8-yl)-1H-pyrrole-1-carboxylate (17.1 g, 37.63 mmol) and 5% Rhodium on Alumina (50% wet) (3.4 g, 0.80 mmol) in MeOH (175 mL) were stirred under an atmosphere of hydrogen at 5 bars and 65° C. for 7 h. The catalyst was removed from the reaction by filtration on a pad of Celite and washed with MeOH. The celite and catalyst were slurried in 500 mL of 10% MeOH in DCM and filtered again. The organic solutions were combined and evaporated to give tert-butyl 2-(6-(methoxycarbonyl)-2-morpholino-4-oxo-4H-chromen-8-yl)pyrrolidine-1-carboxylate (14.4 g, 83%) as a fawn solid.

Mass Spectrum: m/z [M+H]+=459.

Step 3

Hydrogen chloride (4M in dioxane) (2.4 mL, 9.6 mmol) was added to a stirred solution of tert-butyl 2-(6-(methoxycarbonyl)-2-morpholino-4-oxo-4H-chromen-8-yl)pyrrolidine-1-carboxylate (440 mg, 0.96 mmol) dissolved in dioxane (3 mL) and DCM (3 mL) at room temperature and the reaction mixture stirred for 4 h. The solvents were evaporated and the residue azeotroped twice with MeCN and dried under vacuum at 50° C. The remaining solid was then extracted with DCM. The DCM was dried over $MgSO_4$ and concentrated to afford methyl 2-morpholino-4-oxo-8-(pyrrolidin-2-yl)-4H-chromene-6-carboxylate (286 mg, 83%) as a pale beige solid.

Mass Spectrum: m/z [M+H]+=359.

Step 4

Palladium complex (33 mg, 0.04 mmol, see below) was added to a stirred mixture of methyl 2-morpholino-4-oxo-8-(pyrrolidin-2-yl)-4H-chromene-6-carboxylate (270 mg, 0.75 mmol), 1-bromo-3,5-difluorobenzene (0.095 ml, 0.83 mmol) and cesium carbonate (368 mg, 1.13 mmol) dissolved in 1,4-dioxane (5 mL). The resulting suspension was degassed with argon and then stirred at 80° C. for 23 h. The reaction mixture was allowed to cool to room temperature, filtered and concentrated. The crude product was purified by flash chromatography on silica gel eluting with 0 to 6% MeOH in EtAc. The solvent was evaporated to dryness to afford methyl 8-(1-(3,5-difluorophenyl)pyrrolidin-2-yl)-2-morpholino-4-oxo-4H-chromene-6-carboxylate (206 mg, 58%) as a clear yellow foam.

Mass Spectrum: m/z [M+H]+=471.

The palladium complex used as a reactant was made as follows:—

A solution of (9,9-dimethyl-9H-xanthene-4,5-diyl)bis(diphenylphosphine) (256 mg, 0.44 mmol), tris(dibenzylideneacetone)dipalladium (184 mg, 0.20 mmol), and 1-bromo-3,5-difluorobenzene (0.213 mL, 1.85 mmol) in benzene (10 mL) was stirred at room temperature for 96 h. The mixture was then filtered through a pad of Celite and concentrated in vacuo. Ether (10 mL) was added to the residue and yellow crystalline solid was allowed to form upon standing for 4 h. The solid was collected by filtration, washed with ether and dried under vacuum to give the desired palladium complex (139 mg, 39%).

Step 5

An aqueous NaOH 2N (0.622 mL, 1.24 mmol) solution was added to methyl 8-(1-(3,5-difluorophenyl)pyrrolidin-2-yl)-2-morpholino-4-oxo-4H-chromene-6-carboxylate (195 mg, 0.41 mmol) in MeOH (2 mL) and the reaction mixture stirred at 40° C. for 6 h. The mixture was cooled to 0° C. and an aqueous HCl 2N (0.684 mL, 1.37 mmol) solution was added dropwise to the reaction mixture until pH ~5. The solution was partially concentrated and a precipitate appeared. Water was added to the slurry and extracted with DCM. The organic phase was washed with water, dried over $MgSO_4$, filtered and concentrated. The formed precipitate was triturated with ether, filtered, washed with ether, dried under vacuum at 50° C. to afford 8-(1-(3,5-difluorophenyl)pyrrolidin-2-yl)-2-morpholino-4-oxo-4H-chromene-6-carboxylic acid (67 mg, 35%) as a pale beige solid. Mass Spectrum: m/z [M+H]+=457.

The methyl 8-bromo-2-morpholino-4-oxo-4H-chromene-6-carboxylate used as a starting material in Step 1 of the process described for the preparation of 8-(1-(3,5-difluorophenyl)pyrrolidin-2-yl)-2-morpholino-4-oxo-4H-chromene-6-carboxylic acid above was made as follows:—

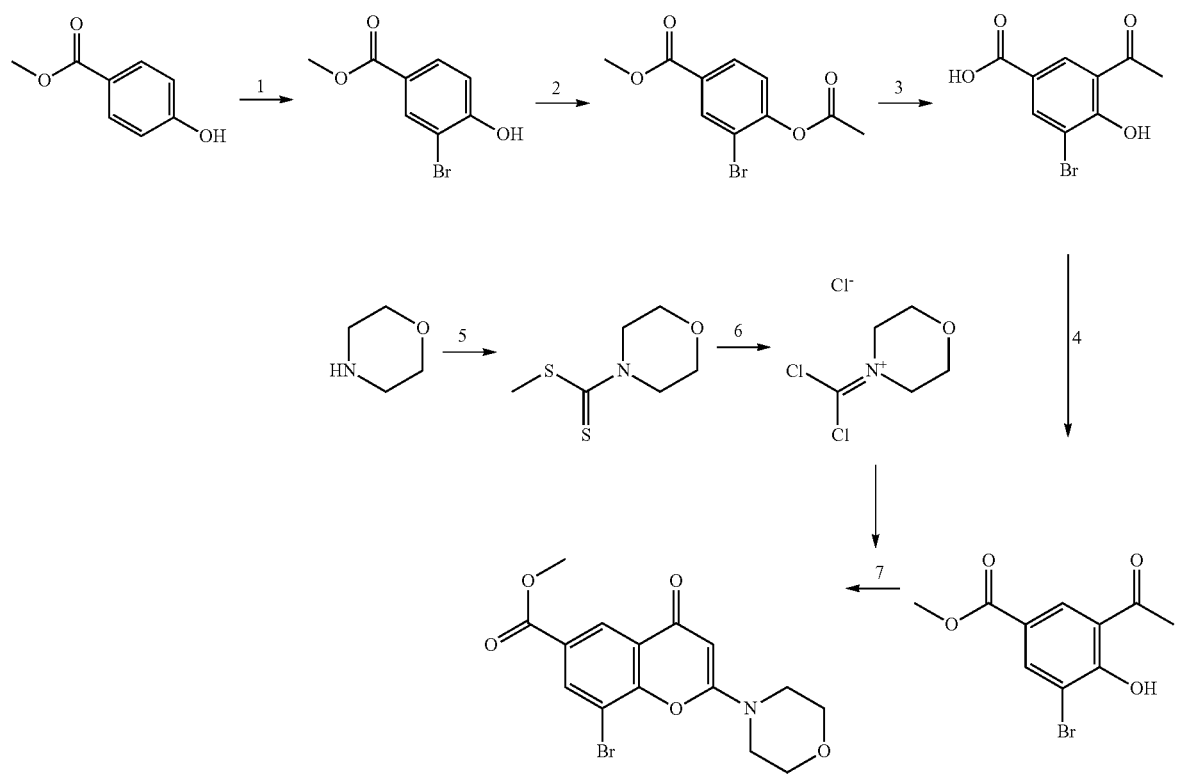

Step 1

To a stirred suspension of methyl 4-hydroxybenzoate (180 g, 1183 mmol) in DCM (3 L) was added dropwise bromine (64 mL, 1242 mmol) under nitrogen and at 0° C. and the reaction mixture was left to stir at room temperature for 36 h. A solution of sodium thiosulfate (500 mL of a 10% solution) was then added while keeping the temperature around 15° C. followed by addition of MeOH (250 mL). The organic layer was washed with water, then brine, dried over MgSO$_4$, filtered and concentrated to dryness to afford methyl 3-bromo-4-hydroxybenzoate (290 g) as a white solid. Mass Spectrum: m/z [M−H]−=229.

Step 2

To a stirred suspension of methyl 3-bromo-4-hydroxybenzoate (270 g, 1168 mmol) in DCM (1.5 L) was added pyridine (150 mL). Acetyl chloride (87 mL, 1227 mmol) was then added dropwise at room temperature and under nitrogen. The mixture was left to stir for 2 h at room temperature. Water (1 L) was then added followed by HCl 2N until pH 1. The organic layer was then washed with water, brine, dried over MgSO$_4$, filtered and evaporated to dryness to afford methyl 4-acetoxy-3-bromobenzoate (300 g, 94%) as a white powder.

Proton NMR Spectrum: (DMSO-d6) 2.34 (s, 3H), 3.87 (s, 3H), 7.47 (d, 1H), 8.01 (dd, 1H), 8.20 (d, 1H).

Step 3

To methyl 4-acetoxy-3-bromobenzoate (150 g, 549.3 mmol) was added aluminum trichloride (220 g, 1647.9 mmol) and the mixture was heated at 140° C. in the absence of solvent for 3 h. Upon cooling to room temperature the solid was crushed and cautiously added to water (1.5 L) with stirring. HCl (250 mL of 12N) was then added and stirring was maintained for 30 mins. The solid obtained was collected by filtration, washed with water (2×2 L) and dried overnight to afford 3-acetyl-5-bromo-4-hydroxybenzoic acid (120 g, 84%) as a yellow powder. Mass Spectrum: m/z [M−H]−=258.

Step 4

To a stirred suspension of 3-acetyl-5-bromo-4-hydroxybenzoic acid (240 g, 926 mmol) in MeOH (2 L) was added dropwise sulfurous dichloride (68 mL, 926.5 mmol) under nitrogen and the mixture was heated at 80° C. for 3 h. The reaction mixture was cooled to room temperature concentrated, diluted with DCM. The organic layer was washed with brine, dried over MgSO$_4$, filtered and concentrated to afford a crude compound, which was purified on silica, eluting with 70% of DCM in petroleum ether. The solvents were evaporated to dryness to afford methyl 3-acetyl-5-bromo-4-hydroxybenzoate (108 g, 42.7%) as a white powder. Mass Spectrum: m/z [M−H]−=229.

Step 5

To a stirred solution of morpholine (201 mL, 2295 mmol) in water (2 L) was added carbon disulfide (0.138 L, 2295.67 mmol) under nitrogen. Sodium hydroxide (96 g, 2410 mmol in solution in 1 L of water) was then added dropwise. The resulting mixture was stirred at room temperature for 1 h, then cooled to 5° C. with an ice bath and dimethyl sulphate (217 mL, 2295 mmol) was added dropwise. The mixture was stirred 1 h at room temperature, the obtained solid was collected by filtration, washed with water (2×1 L) and dried under vacuum over phosphorus pentoxide at 50° C. to give methyl morpholine-4-carbodithioate (360 g, 88%). Proton NMR Spectrum: (CDCl$_3$): 2.68 (s, 3H), 3.71-3.84 (m, 4H), 4.02 (bs, 2H), 4.30 (bs, 2H).

Step 6

Chlorine gas (455 g, 6417 mmol) was bubbled through a solution of methyl morpholine-4-carbodithioate (170 g, 959 mmol) in DCM (1.5 L) over a 2 h period, while keeping the temperature around 10-15° C. Once the chlorine addition was completed, stirring was maintained for an additional 1.5 h while a precipitation occurred. Nitrogen was then passed through the mixture for 30 min. The solid was collected by filtration under nitrogen, washed with DCM and stored under nitrogen in the fridge. There was thus obtained 4-(dichloromethylene)morpholin-4-ium chloride (180 g, 92%) as a white hygroscopic solid.

Step 7

To a stirred solution methyl 3-acetyl-5-bromo-4-hydroxybenzoate (106 g, 388 mmol) in toluene (1 L) was added dropwise (diethyloxonio)trifluoroborate (0.201 L, 1630 mmol), under nitrogen. The resulting solution was left to stir overnight at room temperature, then 4-(dichloromethylene)morpholin-4-ium chloride (143 g, 698 mmol) was added and mixture heated at 90° C. for 12 h. Upon cooling to room temperature, ether (1.5 L) was added and the solid was collected by filtration. This solid was then suspended in MeOH (1 L) and the mixture was heated at 50° C. for 2 h. Upon cooling to room temperature, the solid was collected by filtration then solubilized in DCM (1 L) and washed with water and a saturated solution of sodium bicarbonate. The organic layer was dried over MgSO$_4$, filtered and evaporated to dryness to afford methyl 8-bromo-2-morpholino-4-oxo-4H-chromene-6-carboxylate (68.0 g, 47.6%) as an off-white solid. Mass Spectrum: m/z [M+H]+=368.

An alternate route to prepare methyl 8-bromo-2-morpholino-4-oxo-4H-chromene-6-carboxylate is as follows:

phase was separated, dried over MgSO$_4$, filtered and concentrated to afford a solid which was stirred in ether (5 L) for 2 h. The solid was filtered off and the filtrate concentrated to dryness to afford methyl 3-acetyl-4-hydroxybenzoate (240 g, 82%) as a beige powder. Mass spectrum: m/z [M−H]−=193.

Step 3

To a stirred solution of methyl 3-acetyl-4-hydroxybenzoate (240 g, 1236 mmol) in DCM (2 L) was added pyridine (0.400 L, 4944 mmol) followed by a dropwise addition of dibromine (0.070 L, 1360 mmol) at 0° C. The reaction mixture was stirred at room temperature for 2 h then cooled to 5° C. and HCl 4N (0.927 L, 3708 mmol) was added dropwise. The organic phase was separated, dried over MgSO$_4$, filtered and concentrated to afford a brown solid which was stirred in ether/petroleum ether (1:1, 1 L) for 1 hr. The solid was collected by filtration and dried to afford methyl 3-acetyl-5-bromo-4-hydroxybenzoate (270 g, 80%) as a beige powder. Mass Spectrum: m/z [M+H]+=273.

Step 4

To a solution of lithium bis(trimethylsilyl)amide (1.41 L, 1406 mmol) at −65° C. under nitrogen was added dropwise methyl 3-acetyl-5-bromo-4-hydroxybenzoate (120 g, 439 mmol) in THF (1.2 L). The solution was allowed to warm to 0° C., and maintained at this temperature for 1 h. The solution was cooled back to −65° C. and morpholine-4-carbonyl chlo-

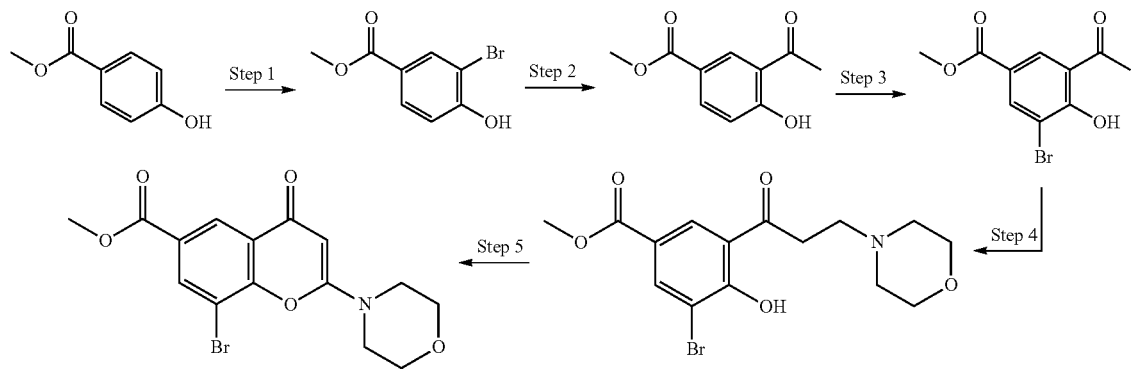

Step 1

Dibromine (0.185 L, 3614.92 mmol) was added dropwise a stirred suspension of methyl 4-s hydroxybenzoate (500 g, 3286 mmol) in DCM (4 L) at 0° C. under N$_2$. The mixture was left to stir for 24 h at r.t. under N$_2$. A solution of sodium metabisulfite (62.5 g, 329 mmol) in 2 L of water was then added, while keeping the temperature around 15° C., followed by 500 mL of MeOH. The organic layer was washed with water, brine, dried over MgSO$_4$, filtered and concentrated to dryness to afford methyl 3-bromo-4-hydroxybenzoate (710 g, 94%) as a white solid. Proton NMR Spectrum (CDCl$_3$): 3.89 (s, 3H), 5.95 (s, 1H), 7.05 (d, 1H), 7.92 (dd, 1H), 8.19 (d, 1H).

Step 2

To a degassed solution of methyl 3-bromo-4-hydroxybenzoate (350 g, 1514.87 mmol) in ethanol (3 L) were added triethylamine (0.528 L, 3787.17 mmol), 1-(vinyloxy)butane (0.588 L, 4544.60 mmol), 1,1'-bis(diphenylphosphino)ferrocene (33.1 g, 60.6 mmol) and diacetoxypalladium (8.50 g, 37.9 mmol) under nitrogen. The mixture was heated at 70° C. overnight. The reaction was cooled down, filtered and the filtrate concentrated. The resulting solid was solubilized with DCM (2 L) and HCl 4N (1.14 L, 4544 mmol) was added under stirring. Stirring was maintained for 2 h, the organic ride (0.055 L, 483 mmol) was added. The mixture was stirred at room temperature for 2 h then cooled to −30° C., DCM (1.5 L) and water (1 L) were added followed by dropwise addition of HCl 6N (500 mL) then HCl 2N (300 mL) until pH 7, the aqueous solution was extracted with DCM (3×). The combined extracts were dried over MgSO$_4$ and evaporated. The crude product was triturated in MTBE to obtain methyl 3-bromo-4-hydroxy-5-(3-morpholino-3-oxopropanoyl)benzoate (153 g, 90%) as a beige solid. Mass Spectrum: m/z [M+H]+=388.

Step 5

Trifluoromethanesulfonic anhydride (0.755 L, 4487 mmol) was added to a stirred solution of methyl 3-bromo-4-hydroxy-5-(3-morpholino-3-oxopropanoyl)benzoate (433 g, 1122 mmol, pooled material from several batches) dissolved in 1,2-dichloroethane (1 L) at room temperature under nitrogen (exotherm). The resulting solution was stirred at 50° C. overnight. The mixture was partially evaporated, and the residue was diluted with MeOH (1.6 L) at 0° C. (exotherm) and stirred for 1 h at RT. The solvent was evaporated again and the residue was diluted in DCM, quenched with a saturated aqueous solution of sodium carbonate and extracted with DCM. The combined organic phases were washed with brine, dried over MgSO$_4$ and concentrated to afford the crude product.

The crude was triturated under MTBE (2×), EtAc (1×) and MTBE (1×). The solid was dried to afford methyl 8-bromo-2-morpholino-4-oxo-4H-chromene-6-carboxylate (208 g, 50%) as a beige solid. Mass Spectrum: m/z [M+H]+=370.

The same route to prepare methyl 8-bromo-2-morpholino-4-oxo-4H-chromene-6-carboxylate was carried out on a larger scale as follows:

Step 2

To vessel A under a nitrogen purge (10 L/min) was charged methyl 3-bromo-4-hydroxybenzoate (200 Kg) and ethanol (1250 Kg). The vessel was evacuated to vacuum and released to nitrogen twice. Triethylamine (220 Kg) was charged followed by an ethanol rinse (15 Kg). Vinyl butyl ether (266 Kg) was charged followed by an ethanol rinse (15 Kg). 1,1'-Bis

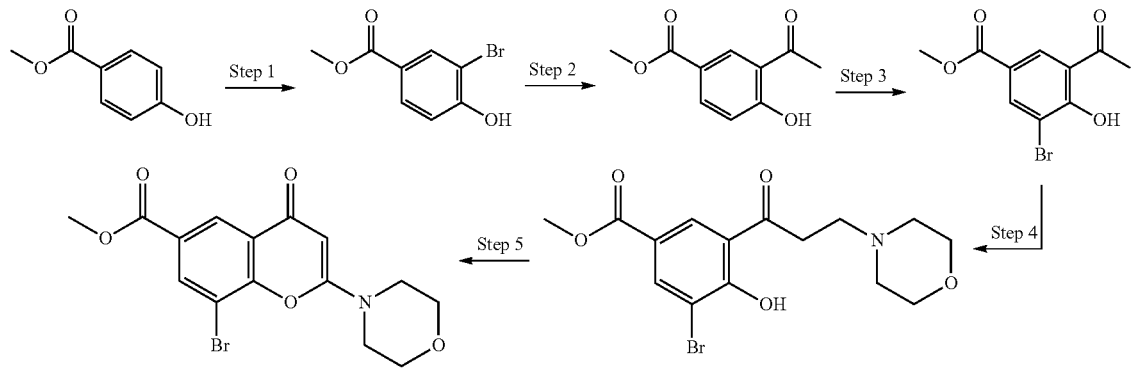

Step 1

To a vessel A under a nitrogen purge (10 L/min) was charged dichloromethane (1060 Kg) and methyl 4-hydroxybenzoate (100 Kg). The reaction was cooled to −2° C. (start temp 3.3° C., final temp −1.7° C., time 1 hour 45 min). Bromine (115 Kg) was charged using nitrogen pressure and maintaining temperature in range −2 to +2° C. (start temp −1.7° C., final temp −0.1° C., high temp 1.2° C., time 4 h). The reaction was stirred for 24 h while allowing to warm up to 20° C. (start temp −0.1° C., final temp 18.2° C.). A solution of sodium metabisulphite (12.5 Kg) in demineralised water (400 Kg) was charged (start temp 17.5° C., end temp 11.0° C., high temp 28.2° C., addition time 3 h 30 min). The resultant suspension was filtered in two approximately equal portions. Load 1 was filtered and washed with demineralised water (200 Kg) followed by heptane (272 Kg) giving a Load 1 damp cake of 204 Kg. Load 2 was filtered and washed with demineralised water (213 Kg). The filter cake (162 Kg) was recharged to vessel A and reslurried with heptane (274 Kg). It was then refiltered, giving a Load 2 damp cake of 132 Kg. Load 1 was dried at 50° C. in a Double Cone Vacuum Drier to give a dry weight of 67.2 Kg.

To vessel B under a nitrogen purge (10 L/min) was charged methyl-3-bromo-4-hydroxybenzoate load 2 (132 Kg) and water (1200 Kg). The reaction was warmed to 15-20° C. (start temp 11.3° C., final temp 15.0° C., time 20 min) and stirred for 75 min. The resulting suspension was filtered on a Stainless Steel Filter. The resulting damp cake (194 Kg) was recharged to vessel B under a nitrogen purge (10 L/min) followed by water (600 Kg). The reaction was warmed to 15-20° C. (start temp 11.7° C., final temp 15.0° C., time 20 min) and stirred for 30 min. The resulting suspension was filtered on a Stainless Steel filter. The resulting damp cake (200 Kg) was dried in a Slurry Pan Drier at 50° C. to give a dry weight of 50.2 Kg. Overall methyl 3-bromo-4-hydroxybenzoate (117.4 kg, 77.3%).

This procedure was carried out four times with minor differences in the reaction conditions and isolation procedures to give in total 429.2 kg of methyl 3-bromo-4-hydroxybenzoate (yield ranging from 62.3% to 77.3%)

(diphenylphosphino)ferrocene (18.9 Kg) was charged followed by diacetoxypalladium (4.96 Kg). The reaction was heated to 70° C. (start temp 17.9° C., final temp 70.1° C., time 2 h 30 min). The reaction was stirred for 13 h. The reaction was cooled to 50° C. (start temp 68.7° C., final temp 53.5° C., time 40 min). The reaction was hot filtered via a glass lined mild steel filter with a 3 cartridge filter on the inlet followed by an ethanol rinse (120 Kg). The ethanol solvent was then distilled off at maximum jacket temperature 50° C. (max base temp=50.7° C., time 7 h 25 min, distillate 1010 Kg). Whilst cooling to 20-25° C., dilute hydrochloric acid (680 Kg made up of 90 Kg of 36% HCl and 590 Kg water) was charged (initial temp 35° C., final temp 24.9° C., time 1 hour) to vessel A. The reaction was stirred for 2 h 30 min. The resulting suspension was filtered on the filter in 2 loads and the filter cakes washed with demineralised water (2500 Kg). Vessel A was charged with methanol (2150 Kg) and the damp filter cake (326 Kg). The reaction was heated to 60° C. (start temp 10.7° C., final temp 59.3° C., time 3 h 45 min). The reaction was hot filtered from vessel A to vessel B via the hot pressure filter and 3 cartridge filters on the inlet to vessel B, followed by dilution with methanol (120 Kg). Demineralised water (815 Kg) was charged to vessel B. The reaction was cooled to 20° C. and the reaction was stirred for 8 h. The resulting suspension was filtered on the filter and the filter cake washed with a mixture of methanol (105 Kg) and demineralised water (60 Kg). The damp product (162 Kg) was dried at 45° C. to give 116.5 Kg of methyl 3-acetyl-4-hydroxybenzoate (99.6% HPLC purity, yield 69.3%).

This procedure was carried out three times with minor differences in the reaction conditions and isolation procedures to give 251.4 kg of methyl 3-acetyl-4-hydroxybenzoate in total (yield ranging from 69.3% to 71.7%)

Step 3

To vessel A under a nitrogen purge (10 L/min) was charged methyl 3-acetyl-4-hydroxybenzoate (80 Kg) and dichloromethane (660 Kg). Pyridine (98 Kg) was charged followed by a dichloromethane rinse (13 Kg). The reaction was cooled to −2° C. (start temp 7.6° C., final temp −4.0° C., time 2 h). Bromine (73.5 Kg) was charged maintaining the temperature between −5 and 0° C. (start temp −4.0° C., final temp −2.5° C., high temp −2.0° C., time 5 h 35 min). The reaction was stirred for 1 hour. A solution of sodium metabisulphite (12.8 Kg) in demineralised water (168 Kg) was charged maintaining temp at 0-5° C. (start temp −7.2° C., end temp −4.0° C., high temp −4.0° C., addition time 30 min). After a 30 minute stir the layers were separated and the lower organic layer discharged (808 Kg). Dichloromethane (111 Kg) was charged to Vessel A and after a 30 minute stir the layers were separated and the lower organic layer discharged (126 Kg). The upper aqueous phase was discharged to waste (301 Kg). The combined organic phases (867 Kg) were charged to Vessel A. 4M hydrochloric acid (336 Kg) was charged and after a 30 minute stir the layers were separated and the lower organic layer discharged (856 Kg). Dichloromethane (111 Kg) was charged and after a 30 minute stir the layers were separated and the lower organic layer discharged (106 Kg). Dichloromethane (111 Kg) was charged to Vessel A and after a 30 minute stir the layers were separated and the lower organic layer discharged (113 Kg). The upper aqueous phase was discharged to waste (404 Kg). The three combined organic layers (1075 Kg) were charged to Vessel A. Demineralised water (168 Kg) was charged and after a 30 minute stir the layers were separated and the lower organic layer discharged (1050 Kg). The upper aqueous phase was discharged to waste (195 Kg). The organic layer was charged to Vessel B, the vessel was rigged for distillation and solvent was distilled off at atmospheric pressure (high base temp 47.8° C., distillate 500 Kg). Methanol (531 Kg) was charged, the vessel was rigged for distillation and solvent was distilled off at atmospheric pressure with maximum base temp of 65° C. (high base temp 65.8° C., high vapour temp 62.9° C., distillate 685 Kg). The reaction was cooled to 20-25° C. (start temp 65.8° C., final temp 23° C., time 2 h). Demineralised water (504 Kg) was charged and the resulting suspension was filtered on the filter press and the filter cake washed with a mixture of water:methanol 2:1 (84 Kg). The damp product (129 Kg) was dried at 45° C. to give methyl 3-acetyl-5-bromo-4-hydroxybenzoate (dry weight: 99.7 Kg, HPLC purity 98%, yield 88.6%).

This procedure was carried out three times with minor differences in the reaction conditions and isolation procedures to give 313 kg of methyl 3-acetyl-5-bromo-4-hydroxybenzoate in total (yield ranging from 87.6% to 89.5%)

Step 4

To vessel A under a nitrogen purge (10 L/min) was charged methyl 3-acetyl-5-bromo-4-hydroxybenzoate (75.3 Kg) and tetrahydrofuran (640 Kg). The mixture was stirred for 15 min to ensure complete solution. The solution (714.5 Kg) was discharged into nitrogen purged drums along with a tetrahydrofuran rinse (10 Kg). To vessel A under a nitrogen purge (10 L/min) was charged lithium bis(trimethylsilyl)amide 20% solution in THF (726 Kg) followed by THF rinse (10 Kg). The vessel contents were cooled to between −10 and −15° C. (Start temp 12.8° C., Final temp −15.6° C., time 45 min). The solution of methyl 3-acetyl-5-bromo-4-hydroxybenzoate in THF (743 Kg) was added maintaining temperature between −10 and −15° C. (Start temp −15.6° C., Final temp −12.9° C., High Temp −11.4° C., time 1 hour 10 min) followed by a tetrahydrofuran rinse (10 Kg). The reaction was stirred for 1 hour 30 min at −10 to −15° C. (start temp −12.9° C., final temp −12.1° C.). Morpholine-4-carbonyl chloride (45.2 Kg) was charged maintaining at −5 to −10° C. (start temp −11.7° C., Final temp −5.6° C., high temp −2.1° C., time 30 min) followed by a tetrahydrofuran rinse (5 Kg). The reaction was stirred for 9 h at 5 to 10° C. The reaction was stirred for 2 additional h at 5 to 10° C. Demineralised water (375 Kg) was charged maintaining temperature below 10° C. (Start temp 7.5° C., Final temp 6.4° C., High Temp 6.1° C., time 34 min). Dichloromethane (700 Kg) was charged maintaining temperature below 10° C. (Start temp 6.5° C., Final temp 10.1° C., High Temp 10.1° C., time 40 min). The reaction mixture was transferred from vessel A to vessel B and rinsed through with dichloromethane (48 Kg). The pH was adjusted to 0.5-2 by addition of 4 M hydrochloric acid solution (459 Kg) and changing to 1 M hydrochloric acid (32.6 Kg) close to the target pH (start pH 12.07, end pH 1.8, start temp 6.1° C., final temp 6.6° C., high temp 10.0° C., addition time 4 h). The layers were separated and the lower aqueous (983 Kg) discharged and then charged to vessel R103 for re-extraction. Dichloromethane (124 Kg) was charged to vessel C and after 15 min stir the layers were separated. The lower organic (435 Kg) was discharged and then charged into vessel D. The upper aqueous (618 Kg) was discharged to waste. Hexane (1105 Kg) was charged over 2 h maintaining the temperature at 5-10° C. (start temp 6.4° C., final temp 5.8° C.). The mixture was cooled to −8° C. (Start temp 5.8° C., final temp −7.1° C.), seeds were charged at −3° C. The resulting suspension was filtered on a Stainless Steel filter in two loads with the damp cake washed with cold hexane (240 Kg) in total (Load 1 damp cake=120 Kg and load 2 damp cake=312 Kg). The combined damp cake (432 Kg) was dried in Slurry Pan Drier at 50° C. for 9 days. (Day 1 and 2: drying under vacuum. Day 3 and 4: heat and vacuum turned off and held under nitrogen. Days 5-7: drying under vacuum. Day 7: product broken up by milling and recharged to dryer) to give methyl 3-bromo-4-hydroxy-5-[3-(morpholin-4-yl)-3-oxopropanoyl]benzoate (Dry weight=79.84 Kg, HPLC purity 93.4%, yield 75%).

This procedure was carried out five times with minor differences in the reaction conditions and isolation procedures to give 308.2 kg of methyl 3-bromo-4-hydroxy-5-[3-(morpholin-4-yl)-3-oxopropanoyl]benzoate in total (yield ranging from 66% to 75%)

Step 5

To vessel A under a nitrogen purge (10 L/min) was charged methyl 3-bromo-4-hydroxy-5-[3-(morpholin-4-yl)-3-oxopropanoyl]benzoate (70 Kg) and chlorobenzene (770 Kg). Trifluoromethanesulphonic anhydride (205 Kg) was charged maintaining below 25° C. (start temp 11.7° C., Final temp 19.8° C., high temp 19.8° C., time 30 min) followed by a chlorobenzene rinse (6 Kg). The reaction was heated up to 70° C. (start temp 19.8° C., final temp 71.0° C., time 2 h). The reaction was stirred for 6 h at 70° C. The reaction was cooled to 5° C. (start temp 71.0° C., final temp 5° C., time 3 h). Methanol (250 Kg) was charged maintaining temperature below 15° C. (Start temp 5° C., Final temp 13.9° C., High Temp 14.1° C., time 2 h 10 min). The reaction was stirred for 20 h at 20-25° C. 20% sodium carbonate solution (403 Kg) was charged until pH 7.5, maintaining temperature below 25° C. (start pH <1, end pH 7.55, start temp 12.0° C., final temp 19.3° C., high temp 20.6° C., addition time 2 hour 5 min). Dichloromethane (371 Kg) was charged. The reaction was stirred for 5 h. Demineralised water (280 Kg) was charged and after stirring for 1 hour, the layers were separated. The lower organic layer (1259 Kg) was discharged. Dichloromethane (371 Kg) was charged to vessel A. After stirring for 30 min the layers were separated. The lower organic layer (394 Kg) was discharged and combined with previous organic. The upper aqueous layer (1031 Kg) was discharged to waste. The combined organics (1689 Kg) were charged to vessel A followed by demineralised water (280 Kg). After stirring for 30 min the layers were separated. The lower organic layer (1538 Kg) was discharged. The upper aqueous layer (390 Kg) was discharged to waste. The organic (1538 Kg) was charged back to vessel A, the vessel was rigged for distillation and solvent was distilled out at down to 100 mbar and at 50° C. until DCM content of reaction mixture below 3.5%. The resulting slurry was cooled to 0-5° C. (start temp 54.4° C., final temp 5.0° C.), stirred for 1 hour and then filtered on the Stainless Steel Filter. The filter cake was washed with ethyl acetate (2×63 Kg) and the damp cake (38.2 Kg) dried in the vacuum oven at 50° C. to give methyl 8-bromo-2-morpholino-4-oxo-4H-chromene-6-carboxylate (Dry weight=34.5 Kg, HPLC purity 98.1%, yield 51.7%)

This procedure was carried several with minor differences in the reaction conditions and isolation procedures to give 112.6 kg of methyl 8-bromo-2-morpholino-4-oxo-4H-chromene-6-carboxylate in total.

EXAMPLE 1.01

8-(1-(3,5-difluorophenyl)pyrrolidin-2-yl)-N-(2-hydroxyethyl)-N-methyl-2-morpholino-4-oxo-4H-chromene-6-carboxamide

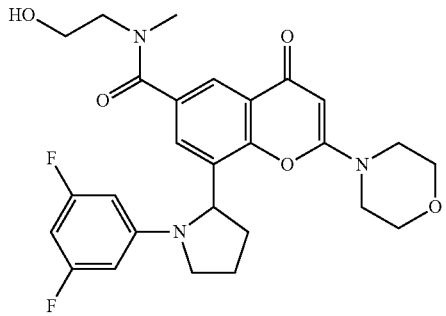 [SMILES: CN(CCO)C(=O)c1cc(C2CCCN2c2cc(F)cc(F)c2)c2oc(N3CCOCC3)cc(=O)c2c1]

TBTU (102 mg, 0.32 mmol) was added to a stirred solution of 8-(1-(3,5-difluorophenyl)pyrrolidin-2-yl)-2-morpholino-4-oxo-4H-chromene-6-carboxylic acid (105 mg, 0.21 mmol), 4-methylmorpholine (0.070 mL, 0.63 mmol) and 2-(methylamino)ethanol (0.022 mL, 0.28 mmol) dissolved in NMP (1.5 mL). The resulting solution was stirred at room temperature for 16 h then purified by preparative HPLC. The fractions were evaporated to dryness and triturated in diethyl ether to afford a solid. This material was collected by filtration, washed with diethyl ether and dried under vacuum at 50° C. to afford 8-(1-(3,5-difluorophenyl)pyrrolidin-2-yl)-N-(2-hydroxyethyl)-N-methyl-2-morpholino-4-oxo-4H-chromene-6-carboxamide (77 mg, 71%) as a white solid.

Mass Spectrum: m/z [M+H]+=514.

Proton NMR Spectrum: (DMSO-d6) 1.77-1.92 (m, 1H), 1.97-2.09 (m, 2H), 2.51-2.60 (m partially hidden by DMSO-d5, 1H), 2.78 (s, 1.2H), 2.93 (s, 1.8H), 3.00-3.09 (m, 0.8H), 3.13-3.23 (m, 0.8H), 3.33-3.49 (m partially hidden by H2O, 2.4H), 3.50-3.66 (m, 5H), 3.70-3.81 (m, 5H), 4.77 (t, 0.6H), 4.78 (t, 0.4H), 5.25 (d, 1H), 5.62 (s, 1H), 6.06-6.18 (m, 2H), 6.32 (t, 1H), 7.13 (s, 0.4H), 7.23 (s, 0.6H), 7.80 (s, 0.6H), 7.84 (s, 0.4H)

EXAMPLE 1.02

8-(1-(3,5-difluorophenyl)pyrrolidin-2-yl)-6-(4-hydroxypiperidine-1-carbonyl)-2-morpholino-4H-chromen-4-one

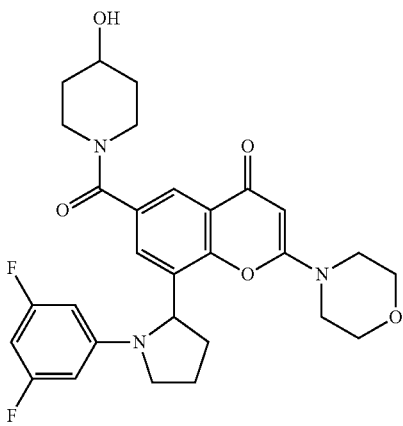 [SMILES: O=C(c1cc(C2CCCN2c2cc(F)cc(F)c2)c2oc(N3CCOCC3)cc(=O)c2c1)N1CCC(O)CC1]

Title compound was prepared using an analogous procedure to that described in Example 1.01. 8-(1-(3,5-difluorophenyl)pyrrolidin-2-yl)-2-morpholino-4-oxo-4H-chromene-6-carboxylic acid (105 mg, 0.21 mmol) was reacted with piperidin-4-ol (22.48 mg, 0.22 mmol) to afford 8-(1-(3,5-difluorophenyl)pyrrolidin-2-yl)-6-(4-hydroxypiperidine-1-carbonyl)-2-morpholino-4H-chromen-4-one (75 mg, 66%) as a white solid.

Mass Spectrum: m/z [M+H]+=540.

Proton NMR Spectrum: (DMSO-d6) 1.02 (bs, 0.5H), 1.19-1.50 (m, 2.5H), 1.74 (bs, 1H), 1.79-1.89 (m, 1H), 1.99-2.13 (m, 2H), 2.52-2.61 (m partially hidden by DMSO-d5, 1H), 2.89 (bs, 1H), 2.94 (bs, 0.5H), 3.26 (bs, 1H), 3.31-3.43 (m partially hidden by H2O, 1.5H), 3.50-3.66 (m, 4H), 3.67 (bs, 1H), 3.71-3.86 (m, 5.5H), 4.00 (bs, 0.5H), 4.75 (d, 1H), 5.22-5.30 (m, 1H), 5.63 (s, 1H), 6.14 (d, 2H), 6.34 (t, 1H), 4.07 (d, 1H), 7.80 (d, 1H)

EXAMPLE 1.03

8-(1-(3,5-difluorophenyl)pyrrolidin-2-yl)-6-(morpholine-4-carbonyl)-2-morpholino-4H-chromen-4-one

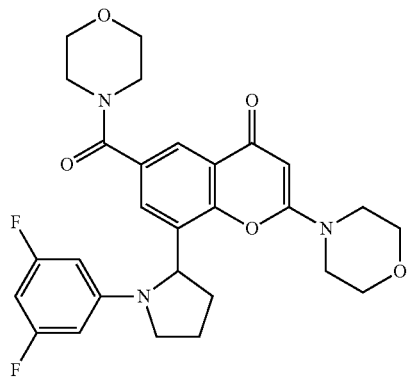 [SMILES: O=C(c1cc(C2CCCN2c2cc(F)cc(F)c2)c2oc(N3CCOCC3)cc(=O)c2c1)N1CCOCC1]

N1-((ethylimino)methylene)-N3,N3-dimethylpropane-1,3-diamine hydrochloride (71.4 mg, 0.37 mmol) was added portionwise to a stirred solution of 8-(1-(3,5-difluorophenyl)pyrrolidin-2-yl)-2-morpholino-4-oxo-4H-chromene-6-carboxylic acid (85 mg, 0.19 mmol), 2-hydroxypyridine 1-oxide (41.4 mg, 0.37 mmol) and morpholine (0.033 mL, 0.37 mmol) at room temperature under nitrogen and stirred for 4 h. The reaction mixture was diluted with DCM, washed with water, brine, dried over MgSO$_4$ and concentrated. The reaction mixture was purified by preparative HPLC. The fractions were evaporated to dryness, and the residue was dissolved in DCM, dried over MgSO$_4$ and concentrated. The remaining solid was triturated with diethyl ether, filtered, washed with diethyl ether and dried under vacuum at 50° C. to afford 8-(1-(3,5-difluorophenyl)pyrrolidin-2-yl)-6-(morpholine-4-carbonyl)-2-morpholino-4H-chromen-4-one (58.0 mg, 59.3%) as a pale beige solid.

Mass Spectrum: m/z [M+H]+=526.

Proton NMR Spectrum: (DMSO-d6) 1.74-1.89 (m, 1H), 1.98-2.09 (m, 2H), 2.50-2.57 (m partially hidden by DMSO-d5, 1H), 3.07 (bs, 3H), 3.24 (bs, 1H), 3.74-3.41 (m, 2H), 3.45

(bs, 2H), 3.49-3.67 (m, 5H), 3.70-3.81 (m, 5H), 5.22-5.29 (m, 1H), 5.62 (s, 1H), 6.13 (d, 2H), 6.34 (t, 1H), 7.07 (d, 1H), 7.82 (d, 1H)

EXAMPLE 1.03a

8-[(2S)-1-(3,5-difluorophenyl)pyrrolidin-2-yl]-6-(morpholine-4-carbonyl)-2-morpholino-4H-chromen-4-one

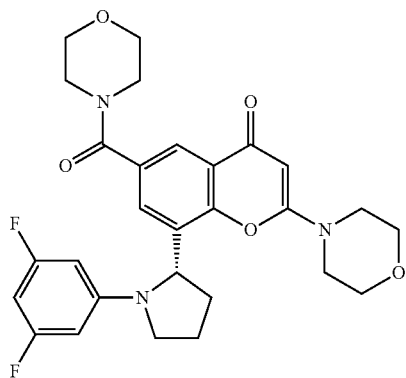

TSTU (75.0 mg, 0.23 mmol) was added in one portion to a stirred solution of 8-[(2S)-(1-(3,5-difluorophenyl)pyrrolidin-2-yl)]-2-morpholino-4-oxo-4H-chromene-6-carboxylic acid (102 mg, 0.21 mmol, >98% enantiomeric purity, made from the first eluting ester enantiomer from chiral separation of tert-butyl 2-(6-(methoxycarbonyl)-2-morpholino-4-oxo-4H-chromen-8-yl)pyrrolidine-1-carboxylate—see below) and DIPEA (0.041 mL, 0.23 mmol) at room temperature The resulting mixture was stirred at room temperature for 1.5 h. Morpholine (0.037 mL, 0.42 mmol) was then added to the reaction mixture and stirring was continued over the week-end. The reaction mixture was purified by preparative HPLC. The fractions were evaporated to dryness, the residue was dissolved in DCM, dried over MgSO$_4$ and concentrated. The remaining solid was triturated with diethyl ether, filtered, washed with diethyl ether and dried under vacuum at 50° C. to afford 8-[(2S)-1-(3,5-difluorophenyl)pyrrolidin-2-yl]-6-(morpholine-4-carbonyl)-2-morpholino-4H-chromen-4-one (64 mg, 57%) as a pale yellow solid.

Mass Spectrum: m/z [M+H]+=526.

Optical Rotation: [α]$^D_{20°}$: 3.4° (16.7 mg in 2 mL of acetonitrile), enantiomeric purity: 95%

Proton NMR Spectrum (CDCl$_3$) 1.96-2.17 (m, 3H), 2.45-2.57 (m, 1H), 3.07-3.83 (m, 14H), 3.83-3.95 (m, 4H), 5.07 (d, 1H), 5.58 (s, 1H), 5.92 (dd, 2H), 6.11 (ddt, 1H), 7.24 (d, 1H), 8.15 (s, 1H)

EXAMPLE 1.03b

8-[(2R)-1-(3,5-difluorophenyl)pyrrolidin-2-yl]-6-(morpholine-4-carbonyl)-2-morpholino-chromen-4-one

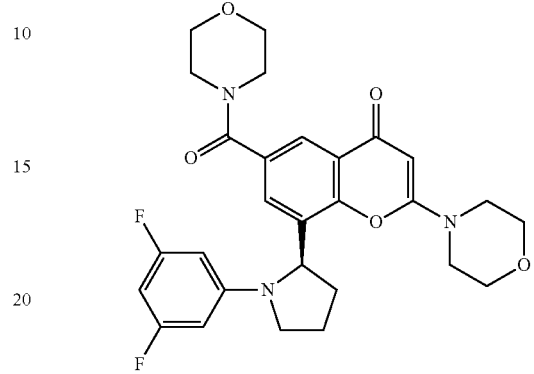

TSTU (106 mg, 0.33 mmol) was added in one portion to a stirred solution of 8-[(2R)-(1-(3,5-difluorophenyl)pyrrolidin-2-yl)]-2-morpholino-4-oxo-4H-chromene-6-carboxylic acid (144 mg, 0.30 mmol, >98% enantiomeric purity, made from the second eluting ester enantiomer from chiral separation of tert-butyl 2-(6-(methoxycarbonyl)-2-morpholino-4-oxo-4H-chromen-8-yl)pyrrolidine-1-carboxylate—see below) and DIPEA (0.057 mL, 0.33 mmol) at room temperature and the resulting mixture was stirred for 1.5 h. Morpholine (0.052 mL, 0.60 mmol) was then added to the reaction mixture and stirring was continued over the week-end. The reaction mixture was purified by preparative HPLC. The fractions were evaporated to dryness, the residue was dissolved in DCM, dried over MgSO$_4$ and concentrated. The remaining solid was triturated with diethyl ether, filtered, washed with diethyl ether and dried under vacuum at 50° C. to afford 8-[(2R)-1-(3,5-difluorophenyl)pyrrolidin-2-yl]-6-(morpholine-4-carbonyl)-2-morpholino-chromen-4-one (69 mg, 44%) as a pale yellow solid.

Mass Spectrum: m/z [M+H]+=526.

Optical Rotation: [α]$^D_{20°}$: −4.5° (14.8 mg in 2 mL of acetonitrile), enantiomeric purity: 97%

Proton NMR Spectrum (CDCl$_3$) 1.96-2.17 (m, 3H), 2.45-2.57 (m, 1H), 3.07-3.83 (m, 14H), 3.83-3.95 (m, 4H), 5.07 (d, 1H), 5.58 (s, 1H), 5.92 (dd, 2H), 6.11 (ddt, 1H), 7.24 (d, 1H), 8.15 (s, 1H)

The 8-(1-(3,5-difluorophenyl)pyrrolidin-2-yl)-2-morpholino-4-oxo-4H-chromene-6-carboxylic acid (R) and (S)-enantiomers used as starting material were made as follows:—

Step 1

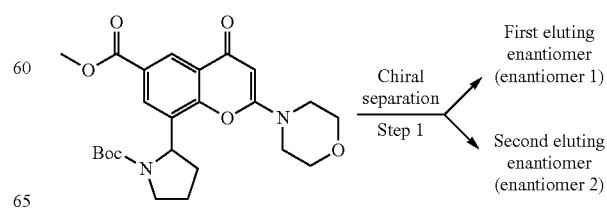

Chiral Preparative HPLC Conditions:

| | |
|---|---|
| Instrument | Prochrom |
| Column | Prochrom 200 mm 20 μm Chiralpak IA |
| Eluent | TBME/MeOH 80/20 |
| Flow | 1000 ml/min |
| Wavelength | 254 nm |
| Sample Conc | 3.75 g/400 ml TBME/MeOH 80/20 |
| Injection volume | 400 ml |
| Run Time | 20 mins |

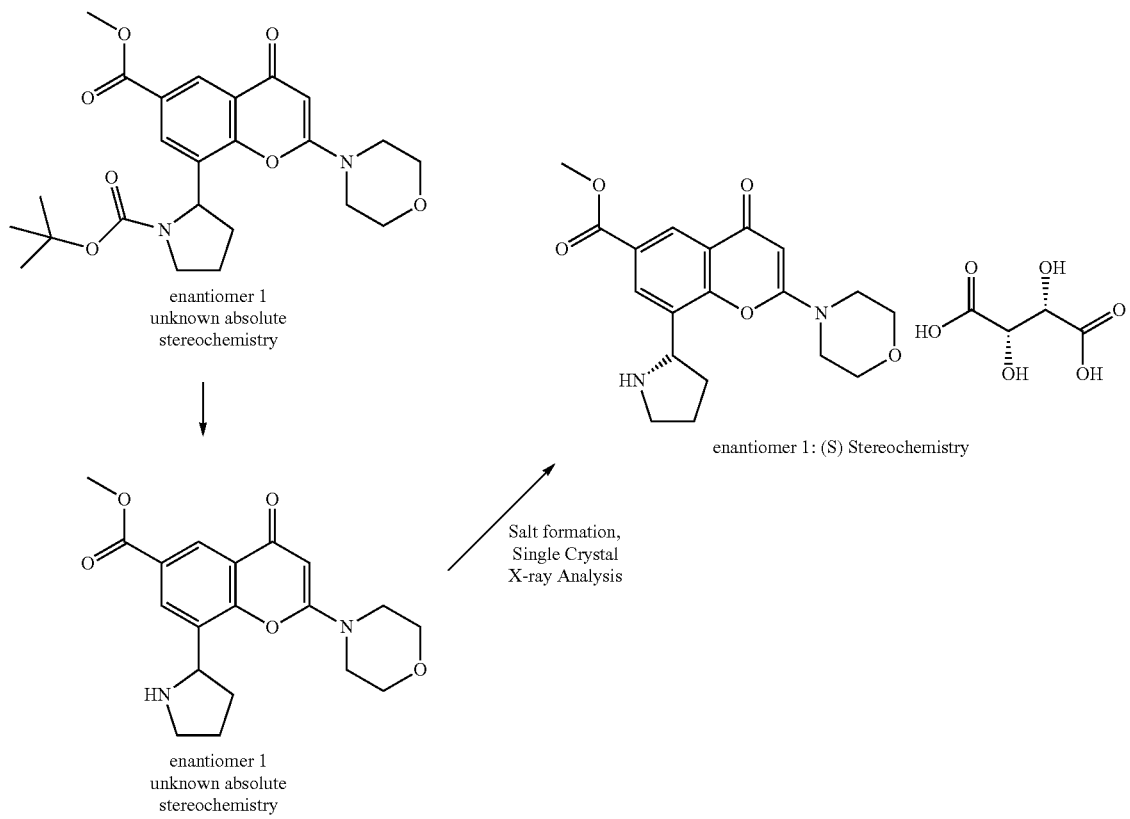

15 g of tert-butyl 2-(6-(methoxycarbonyl)-2-morpholino-4-oxo-4H-chromen-8-yl)pyrrolidine-1-carboxylate (prepared as described in Example 1.00 above) was separated in 5 injections by chiral HPLC. First eluting enantiomer: 6.32 g, strength=91%, αD=−72.7°; Second eluting enantiomer: 6.94 g, strength=89%, αD=+69.4°. Enantiomeric purity >98% for each enantiomer.

Alternative Chiral Preparative HPLC Conditions:

| | |
|---|---|
| Instrument | Kronlab |
| Column | Merck 100 mm 20 μm Chiralpak IC |
| Eluent | MeOH/TEA 99.9/0.1 |
| Flow | 1 ml/min |
| Wavelength | 225 nm, 254 nm |
| Sample Conc | 20 mg/ml in EtOH |
| Injection volume | 50 ml |
| Run Time | 40 mins |

6.1 g of tert-butyl 2-(6-(methoxycarbonyl)-2-morpholino-4-oxo-4H-chromen-8-yl)pyrrolidine-1-carboxylate separated in 5 injections. 1st first eluting enantiomer: 1.88 g; 2nd eluting enantiomer: 1.98 g. Enantiomeric purity >98% for each enantiomer.

The absolute stereochemistry of the two enantiomers of tert-butyl 2-(6-(methoxycarbonyl)-2-morpholino-4-oxo-4H-chromen-8-yl)pyrrolidine-1-carboxylate obtained after chiral HPLC was established according to the following procedure.

Methyl 2-morpholino-4-oxo-8-(pyrrolidin-2-yl)-4H-chromene-6-carboxylate enantiomer 1 was obtained from tert-butyl 2-(6-(methoxycarbonyl)-2-morpholino-4-oxo-4H-chromen-8-yl)pyrrolidine-1-carboxylate enantiomer 1 by acidic deprotection with hydrogen chloride (see step 1 of the preparation of 8-[(2R)-1-(3,5-difluorophenyl)pyrrolidin-2-yl]-6-(morpholine-4-carbonyl)-2-morpholino-chromen-4-one (i.e. Example 1.03b) below for an analogous procedure). The resulting methyl 2-morpholino-4-oxo-8-(pyrrolidin-2-yl)-4H-chromene-6-carboxylate enantiomer 1 was then mixed with D-(S,S)-tartaric acid (0.5 eq) to give the methyl 2-morpholino-4-oxo-8-(pyrrolidin-2-yl)-4H-chromene-6-carboxylate (2S,3S)-2,3-dihydroxysuccinate salt, which was crystallized from methanol/isopropanol using the vapour diffusion method. A small amount of the sample was dissolved in methanol in a vial, and this vial placed inside a larger vial containing a small volume of isopropanol antisolvent. Diffusion of the isopropanol antisolvent into the methanol salt solution over time caused crystallisation, and the absolute configuration of the resultant crystal was determined by single-crystal X-ray diffraction. In accordance with the Cahn-Ingold-Prelog sequence rules, the chiral carbon atom of methyl 2-morpholino-4-oxo-8-(pyrrolidin-2-yl)-4H-chromene-6-carboxylate (2S,3S)-2,3-dihydroxysuccinate salt was determined to have an (S)-configuration. As a result, enantiomer 2 of tert-butyl 2-(6-(methoxycarbonyl)-2-morpholino-4-oxo-4H-chromen-8-yl)pyrrolidine-1-carboxylate was assigned the (R)-configuration.

The following procedure describes the preparation of 8-[(2R)-1-(3,5-difluorophenyl)pyrrolidin-2-yl]-6-(morpholine-4-carbonyl)-2-morpholino-chromen-4-one (i.e. Example 1.03b) from the second eluting ester enantiomer above (i.e tert-butyl (2R)-2-(6-(methoxycarbonyl)-2-morpholino-4-oxo-4H-chromen-8-yl)pyrrolidine-1-carboxylate). An analogous procedure was used for the synthesis of 8-[(2S)-1-(3,5-difluorophenyl)pyrrolidin-2-yl]-6-(morpholine-4-carbonyl)-2-morpholino-chromen-4-one (i.e. Example 1.03a) from the first eluting ester enantiomer above in step 1 (i.e. tert-butyl (2S)-2-(6-(methoxycarbonyl)-2-morpholino-4-oxo-4H-chromen-8-yl)pyrrolidine-1-carboxylate).

Step 2

Diacetoxypalladium (0.028 g, 0.13 mmol) was added to a stirred mixture of methyl 2-morpholino-4-oxo-8-[(2R)-pyrrolidin-2-yl]chromene-6-carboxylate (0.9 g, 2.51 mmol), 1-bromo-3,5-difluorobenzene (0.361 ml, 3.14 mmol), (9,9-dimethyl-9H-xanthene-4,5-diyl)bis(diphenylphosphine) (145 mg, 0.25 mmol) and cesium carbonate (1.227 g, 3.77 mmol) dissolved in 1,4-dioxane (16 mL). The resulting suspension was degassed with argon and then stirred at 100° C. for 15 h. The reaction mixture was allowed to cool to room temperature, concentrated in presence of silica gel and purified by flash chromatography on silica gel eluting with 0 to 10% MeOH in EtAc. The solvent was evaporated to dryness to afford methyl 8-[(2R)-1-(3,5-difluorophenyl)pyrrolidin-2-yl]-2-morpholino-4-oxo-chromene-6-carboxylate (0.792 g, 67%) as an yellow foam. Mass Spectrum: m/z [M+H]+=471.

Step 3

An aqueous NaOH 2N (2.55 ml, 5.10 mmol) solution was added to methyl 8-[(2R)-1-(3,5-difluorophenyl)pyrrolidin-2-yl]-2-morpholino-4-oxo-chromene-6-carboxylate (0.79 g,

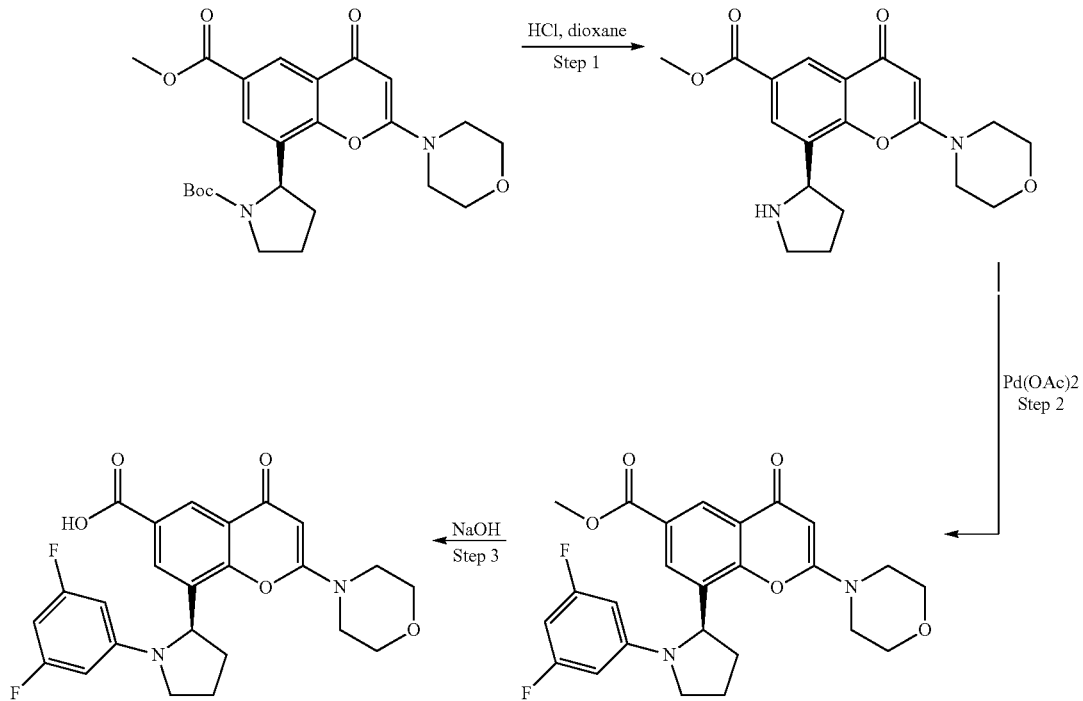 [SMILES: COC(=O)c1cc([C@H]2CCCN2C(=O)OC(C)(C)C)c2oc(N3CCOCC3)cc(=O)c2c1 ; COC(=O)c1cc([C@H]2CCCN2)c2oc(N3CCOCC3)cc(=O)c2c1 ; O=C(O)c1cc([C@H]2CCCN2c2cc(F)cc(F)c2)c2oc(N3CCOCC3)cc(=O)c2c1 ; "NaOH" ; COC(=O)c1cc([C@H]2CCCN2c2cc(F)cc(F)c2)c2oc(N3CCOCC3)cc(=O)c2c1]

Step 1

Hydrogen chloride (4M in dioxane) (8.81 mL, 35.22 mmol) was added to a stirred solution of tert-butyl (2R)-2-(6-(methoxycarbonyl)-2-morpholino-4-oxo-4H-chromen-8-yl)pyrrolidine-1-carboxylate (1.90 g, 3.52 mmol) dissolved in DCM (15 mL) and the reaction mixture was stirred for 8 h at room temperature After concentration, 10% methanolic ammonia (7 N) in DCM was added, the reaction mixture was adsorbed on silica gel and then purified by flash chromatography on silica gel eluting with 0 to 8% methanolic ammonia (7 N) in DCM. The solvents were evaporated to dryness to afford after trituration with diethyl ether, methyl 2-morpholino-4-oxo-8-[(2R)-pyrrolidin-2-yl]chromene-6-carboxylate (1.11 g, 88%) as a light orange crystalline solid.

Mass Spectrum: m/z [M+H]+=359.

1.68 mmol) in a mixture of MeOH (9 mL) and DCM (6 mL) and the reaction mixture was stirred at room temperature overnight. The mixture was cooled to 0° C. and an aqueous HCl 2N (2.5 mL, 5.0 mmol) solution was added dropwise to the reaction mixture until pH ~3. After dilution with water (9 mL), the reaction mixture was concentrated to half volume. The aqueous phase was extracted with DCM, the organic phase was concentrated to dryness, leading to a foam, which was triturated in EtAc, collected by filtration, washed with EtAc, diethyl ether, dried under vacuum at 50° C. to afford 8-[(2R)-1-(3,5-difluorophenyl)pyrrolidin-2-yl]-2-morpholino-4-oxo-chromene-6-carboxylic acid (0.638 g, 83%) as an off-white solid. Mass Spectrum: m/z [M+H]+=457.

Examples 1.03a and 1.03b were also synthesised on a large scale according to the following procedure:

Step 1

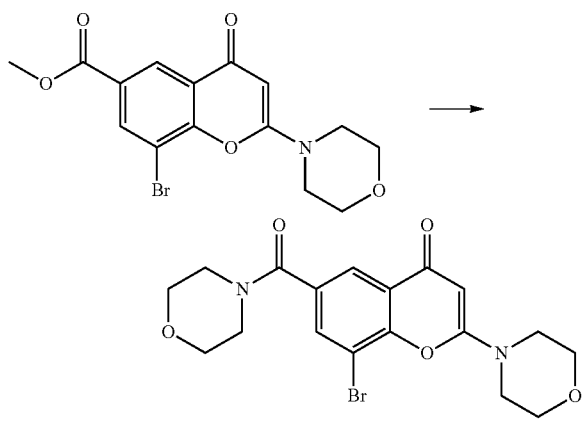

KOH (0.419 L, 4889 mmol) was added portionwise to methyl 8-bromo-2-morpholino-4-oxo-4H-chromene-6-carboxylate (900 g, 2444 mmol) in water (5 L) at 20° C. over a period of 1 hour. The resulting suspension was stirred at 20° C. for 4 hours until saponification was complete. The reaction was filtered to remove insoluble particles and transferred into a vessel containing water (2 L) (vessel 1). Morpholine (0.639 L, 7333 mmol) was added and agitation continued. 2-chloro-4,6-dimethoxy-1,3,5-triazine (1931 g, 11000 mmol) and water (8 L) was charged to vessel 2 and the temperature adjusted to approximately 7° C., 4-methylmorpholine (134 mL, 1222 mmol) was charged at a rate to maintain the contents at 10° C. and the contents agitated for 4 hours. The contents of vessel 2 was transferred to vessel 1 and agitated at room temperature overnight. DCM (5 L) was then added and the mixture transferred to a 30 litre separator, extracted with a further portion of DCM and the organic extracts combined, dried (Na$_2$SO$_4$) and evaporated to dryness. The solid was stirred in ethyl acetate and filtered to give 8-bromo-6-(morpholine-4-carbonyl)-2-morpholino-4H-chromen-4-one (520 g, 50.3%) as a slightly grey solid. Mass Spectrum: m/z [M+H]+=425.

Step 2

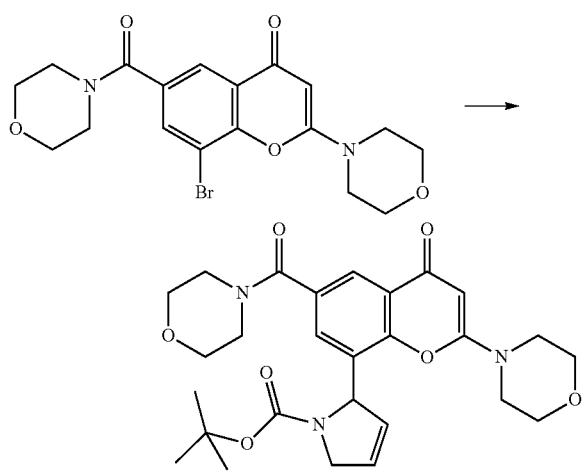

DMF (4 L) was degassed by bubbling through a stream of nitrogen for 15 minutes. A 10 litre jacketed vessel was charged with a portion of the DMF (600 mL), followed by 8-bromo-6-(morpholine-4-carbonyl)-2-morpholino-4H-chromen-4-one (440 g, 1040 mmol), tert-butyl 2,3-dihydro-1H-pyrrole-1-carboxylate (246 g, 1455 mmol), triphenylphosphine (27.3 g, 104 mmol) and potassium carbonate (431 g, 3119 mmol). The remainder of the DMF (3 L) was added followed by diacetoxypalladium (11.67 g, 52 mmol). The resulting suspension was stirred under nitrogen and was heated at 100° C. for 16 hours. The mixture was cooled to room temperature and diluted with DCM (4 L). The mixture was filtered through celite, the filtrate and washings were poured into water (38 L) and further DCM was added (2.5 L). The organic layer was separated and the aqueous phase was extracted with further DCM (2.5 L). The organic phases were dried with magnesium sulfate, filtered and concentrated to give a brown gum. The gum was purified by flash column chromatography on silica eluting with DCM, then 0-10% MeOH/DCM. The forerunners containing Ph$_3$P contained a significant quantity of product. These were concentrated to afford impure material. The pure fractions gave 442 g of pure product. The forerunners were repurified as before (750 g Silica cartridge) to afford a further 24 g of pure product. Both crops were combined to give tert-butyl 2-(6-(morpholine-4-carbonyl)-2-morpholino-4-oxo-4H-chromen-8-yl)-2,5-dihydro-1H-pyrrole-1-carboxylate (466 g, 88%) as a yellow solid. Mass Spectrum: m/z [M+H]+=512.

Step 3

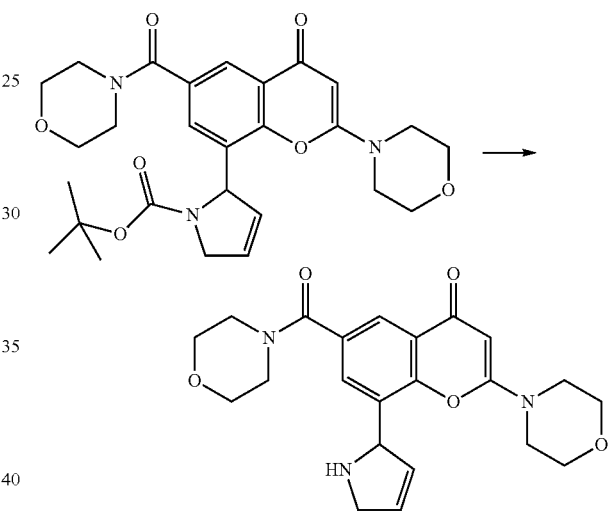

Trifluoroacetic acid (1.6 L) was added to a solution of tert-butyl 2-(6-(morpholine-4-carbonyl)-2-morpholino-4-oxo-4H-chromen-8-yl)-2,5-dihydro-1H-pyrrole-1-carboxylate (444 g, 867.92 mmol) in DCM (3 L). The mixture was stirred for 16 hours at room temperature The solution was concentrated under reduced pressure. The residue was diluted with DCM (2.5 L) and added to a vigorously stirred mixture of DCM (1 L) and conc. aqueous ammonia (4 L). The aqueous was washed with further DCM (2 L). The combined organic solution was dried with magnesium sulfate, filtered, and concentrated under reduced pressure to afford an orange dry film which was used in the next step without further purification.

Step 4

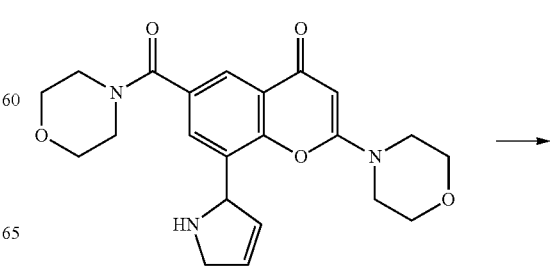

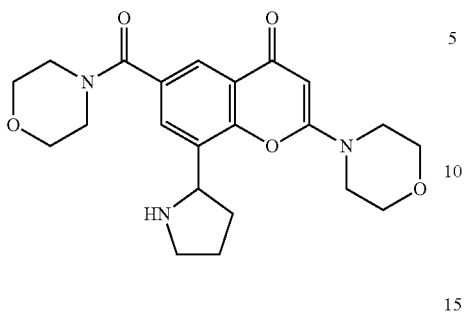

8-(2,5-dihydro-1H-pyrrol-2-yl)-6-(morpholine-4-carbonyl)-2-morpholino-4H-chromen-4-one (353 g, 858 mmol) and Palladium on carbon 5% JM Type87L (70 g, 16 mmol) in MeOH (3500 mL) were stirred under an atmosphere of hydrogen at 5 bar and 45° C. for 3 hours. The reaction mixture was filtered through Celite and concentrated under reduced pressure. The residue purified by flash column chromatography on silica using gradient elution (1% methanol/DCM to 20% methanol/DCM containing 1% conc aqueous ammonia). The desired product, 6-(morpholine-4-carbonyl)-2-morpholino-8-(pyrrolidin-2-yl)-4H-chromen-4-one (187 g, 53%), was thus isolated as a colourless dry film. More material was made by repeating this reaction.

Step 5

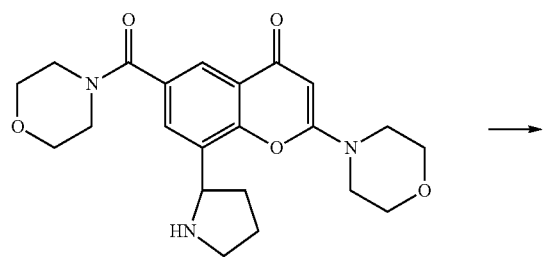

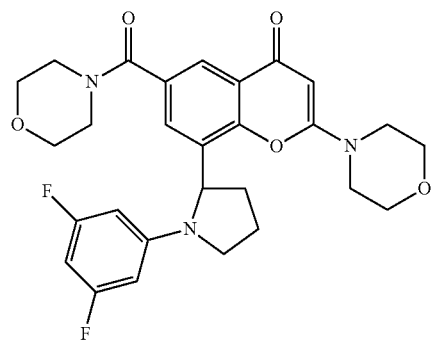

6-(morpholine-4-carbonyl)-2-morpholino-8-(pyrrolidin-2-yl)-4H-chromen-4-one (296 g, 716 mmol), 1-bromo-3,5-difluorobenzene (173 g, 895 mmol) and cesium carbonate (700 g, 2148 mmol) suspended in dioxane (3 L) was bubbled with nitrogen for 10 minutes. diacetoxypalladium (8.04 g, 36 mmol) and (9,9-dimethyl-9H-xanthene-4,5-diyl)bis(diphenylphosphine) (41.4 g, 72 mmol) were added and the mixture bubbled with nitrogen for 2 minutes then heated at 100° C. for 2 hours. Upon cooling to room temperature the mixture was partitioned between DCM (500 mL) and water (250 mL). The organic phase was washed with brine and dried with magnesium sulfate, filtered and concentrated under reduced pressure to give a brown gum. The gum was purified by flash column chromatography on silica using gradient elution (0% methanol/DCM to 5% methanol/DCM). The desired product, 8-(1-(3,5-difluorophenyl)pyrrolidin-2-yl)-6-(morpholine-4-carbonyl)-2-morpholino-4H-chromen-4-one (282 g, 75%), was thus isolated as a pale yellow dry film. Mass Spectrum: m/z [M+H]+=526. More material was made by repeating this reaction.

Step 6

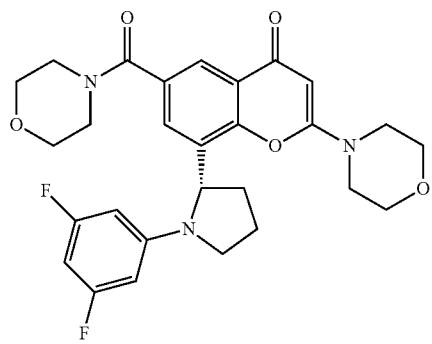

1.03a

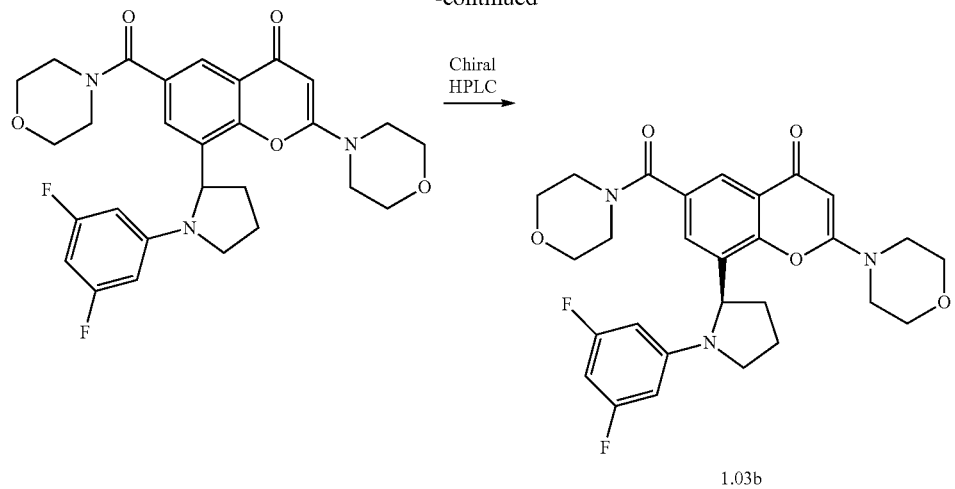

1.03b

Each enantiomer was isolated by preparative HPLC as follows:

A solution of racemic 8-(1-(3,5-difluorophenyl)pyrrolidin-2-yl)-6-(morpholine-4-carbonyl)-2-morpholino-4H-chromen-4-one (325 g) was dissolved in a 50% v/v mixture of methanol in ethanol. 800 mL aliquots of this mixture, each containing 12 g of racemate, were injected sequentially onto a Prochrom 200 mm 20 μm Chiralpak AD column (5 kg CSP) using a Prochrom HPLC instrument. Enantiomers were eluted at room temperature using an eluent containing 25% heptane: 37.5% methanol: 37.5% ethanol, at a flowrate of 1.2 Lmin-1 and a run time of 25 minutes. The first enantiomer to elute had a retention time of 6.5 min and the second enantiomer began to elute after 10 minutes. The first eluting enantiomer, 143 g, 272 mmol, 50.7%) was obtained as a cream solid and the second eluting enantiomer, 59 g) was recovered as a brown film.

Analytical Conditions Post Chiral Purification:

Chiralpak ID 4.6×250 mm 5 μm column. Eluted with EtOH:MeOH (50:50) at 1 ml/min. The run time was 30 minutes at a temperature of 25° C.

The retention times for the enantiomer which had eluted first from the separation in step 6 above was 17.73 mins. This was compared with an authentic sample of Example 1.03b prepared according to the method described above, and identified it as the enantiomer of Example 1.03b, i.e. 8-[(2R)-1-(3,5-difluorophenyl)pyrrolidin-2-yl]-6-(morpholine-4-s carbonyl)-2-morpholino-chromen-4-one. The retention time of the second eluting enantiomer was 13.52 mins, identifying it as the enantiomer of Example 1.03a, i.e. 8-[(2S)-1-(3,5-difluorophenyl)pyrrolidin-2-yl]-6-(morpholine-4-carbonyl)-2-morpholino-chromen-4-one.

Chiral chromatography estimated the level of the opposite enantiomer in the first eluting enantiomer from step 6 above (i.e. the enantiomer of Example 1.03b, 8-[(2R)-1-(3,5-difluorophenyl)pyrrolidin-2-yl]-6-(morpholine-4-carbonyl)-2-morpholino-chromen-4-one) as approximately 0.7%, giving an enantiomeric purity of 99.3% and an enantiomeric excess of 98.6%.

A crystalline form (Form A) of the compound of Example 1.03b was also produced according to the following method:

8-[(2R)-1-(3,5-difluorophenyl)pyrrolidin-2-yl]-6-(morpholine-4-carbonyl)-2-morpholino-chromen-4-one (9 g) was slurried in ether (180 mL) for 72 hours. The resulting off white powder was isolated by filtration and dried. It was then analysed by XRPD and shown to be crystalline (FIG. 1), having the following 2θ values measured using CuKa radiation:

| Angle 2-Theta (2θ) | Intensity % |
|---|---|
| 4.8 | 37.0 |
| 6.4 | 18.9 |
| 8.1 | 53.6 |
| 9.6 | 49.0 |
| 15.8 | 32.3 |
| 19.5 | 100.0 |
| 20.3 | 20.3 |
| 22.7 | 27.0 |
| 23.4 | 29.6 |
| 25.9 | 13.9 |

Figure 2:
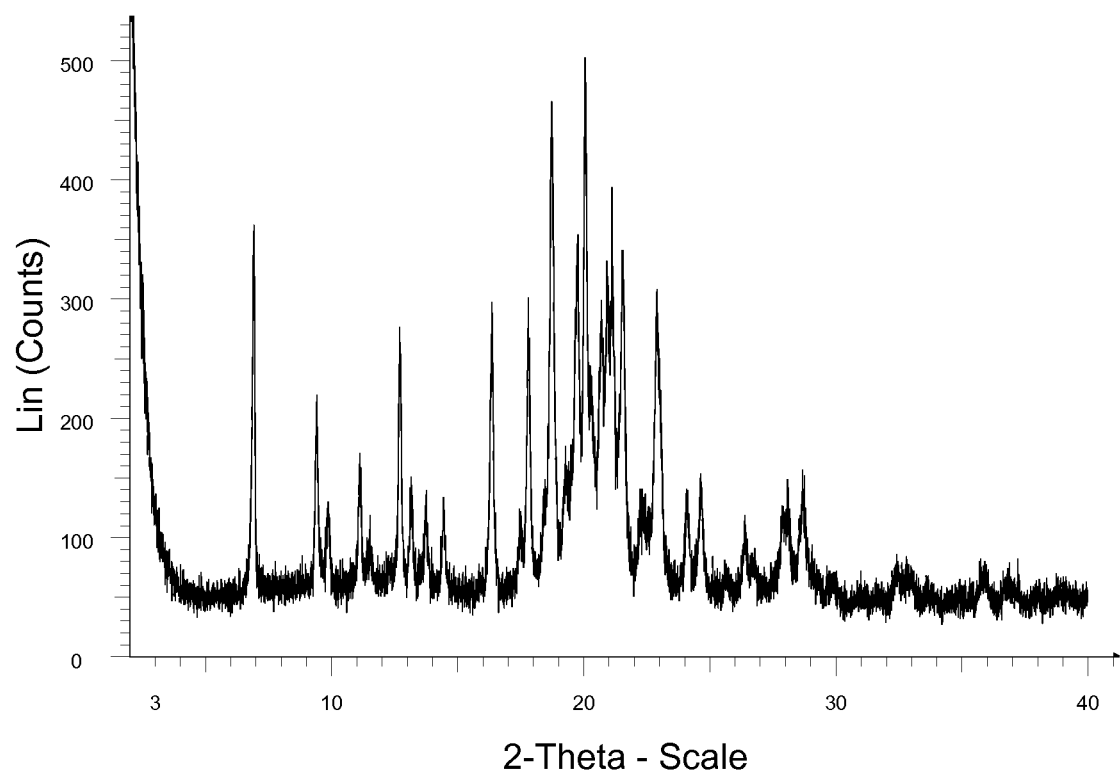
FIG. 2: X-Ray Powder Diffraction Pattern of Example 1.03b Form B

A further crystalline form (Form B) of the compound of Example 1.03b was also produced according to the following method:

8-[(2R)-1-(3,5-difluorophenyl)pyrrolidin-2-yl]-6-(morpholine-4-carbonyl)-2-morpholino-chromen-4-one (1.77 g) was slurried in ether (40 mL) for 12 hours. The resulting off white powder (720 mg) was isolated by filtration and dried. It was analysed by XRPD (FIG. 2) and shown to be a different crystalline form to Form A, with the following 2θ values measured using CuKa radiation:

| Angle 2-Theta (2θ) | Intensity % |
|---|---|
| 6.9 | 74.2 |
| 9.4 | 47.0 |
| 9.8 | 27.7 |
| 11.1 | 35.2 |
| 12.7 | 56.4 |
| 13.1 | 30.7 |
| 13.7 | 28.1 |
| 17.8 | 64.6 |
| 18.7 | 100.0 |
| 19.7 | 62.4 |

Figure 3:
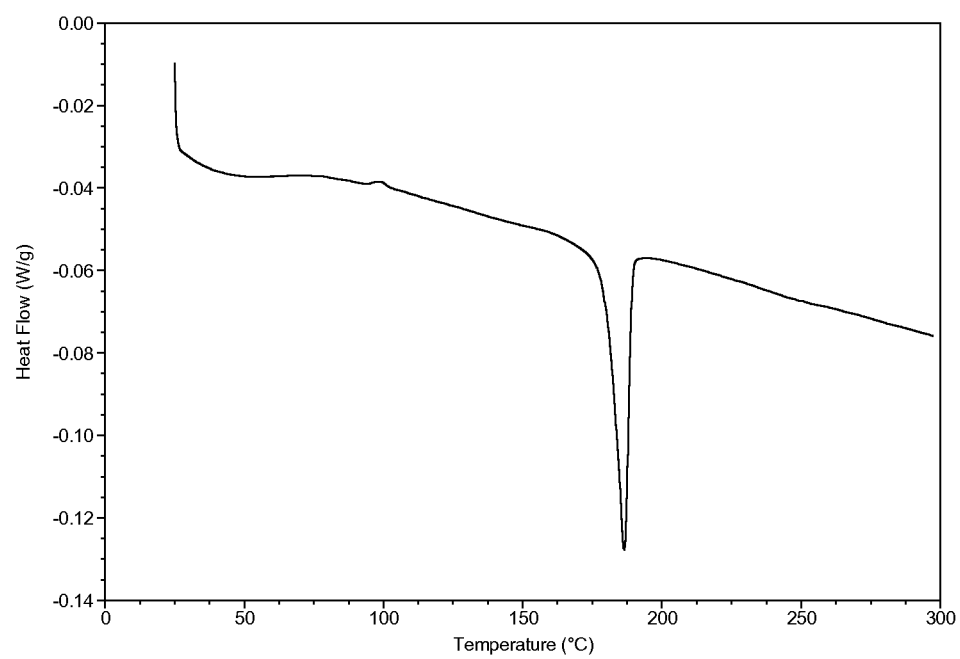
FIG. 3: DSC Thermogram of Example 1.03b Form B

DSC analysis of Form B was also carried out (FIG. 3), which showed a melting point of 180.2° C. (onset).

Figure 4:
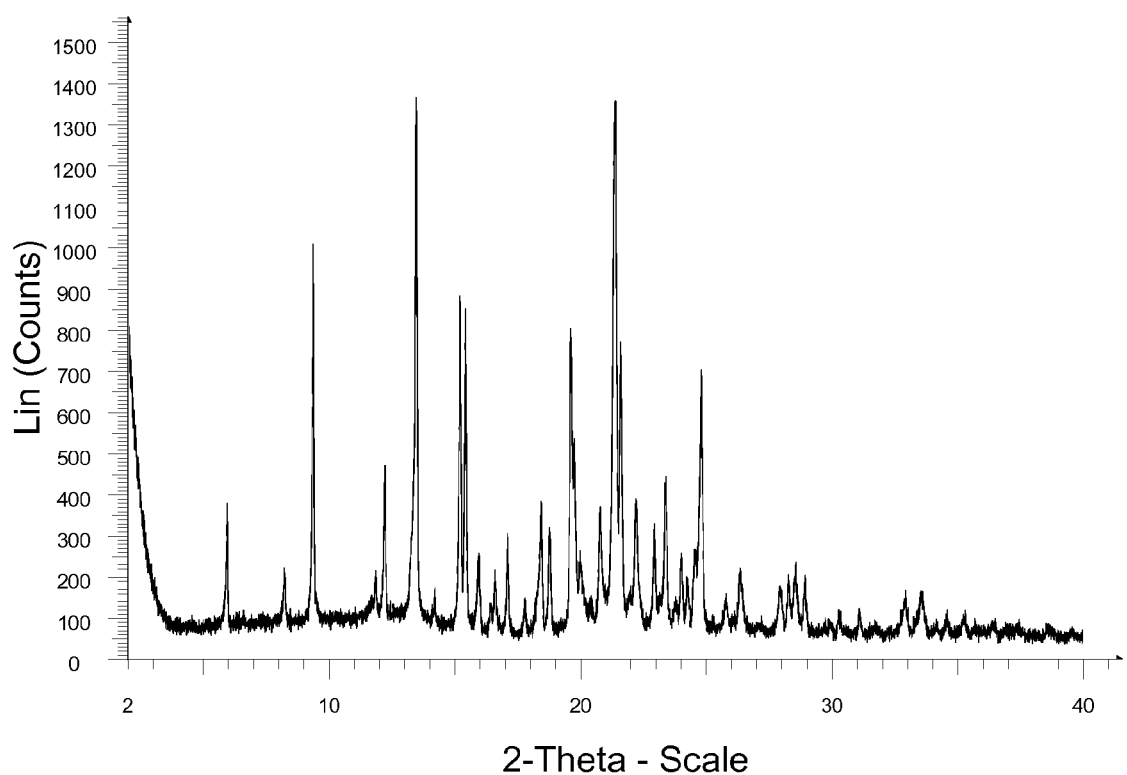
FIG. 4: X-Ray Powder Diffraction Pattern of Example 1.03b Form C

A further crystalline form (Form C) of the compound of Example 1.03b was also produced by slurrying Form B material in methanol. Approximately 20 mg of Form B material was placed in a vial with a magnetic flea, and approximately 2 ml of methanol added. The vial was then sealed tightly with a cap and left to stir on a magnetic stirrer plate. After 3 days, the sample was removed from the plate, the cap taken off and the slurry left to dry under ambient conditions before it was analysed by XRPD (FIG. 4). This form (Form C) was determined to be crystalline by XRPD and seen to be different to previously seen forms; with the following 2θ values measured using CuKa radiation:

| Angle 2-Theta (2θ) | Intensity % |
|---|---|
| 5.9 | 27.6 |
| 11.8 | 15.6 |
| 12.2 | 34.3 |
| 13.5 | 100.0 |
| 15.2 | 64.5 |
| 15.4 | 62.2 |
| 17.1 | 22.3 |

EXAMPLE 1.04

8-[1-(3,5-difluorophenyl)pyrrolidin-2-yl]-2-morpholino-6-[(1-oxidothiomorpholin-4-yl)carbonyl]-4H-chromen-4-one

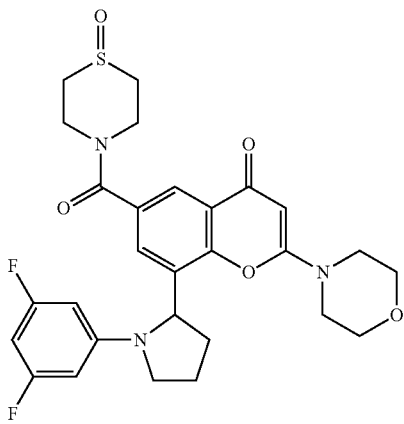 [SMILES: O=C(c1cc(C2CCCN2c2cc(F)cc(F)c2)c2oc(N3CCOCC3)cc(=O)c2c1)N1CCS(=O)CC1]

TBTU (176 mg, 0.55 mmol) was added in one portion to a stirred solution of 8-(1-(3,5-difluorophenyl)pyrrolidin-2-yl)-2-morpholino-4-oxo-4H-chromene-6-carboxylic acid (125 mg, 0.27 mmol) and DIPEA (0.286 mL, 1.64 mmol) at room temperature and stirred for 2.5 h. Thiomorpholine 1-oxide hydrochloride (85 mg, 0.55 mmol) was added to the reaction mixture and stirring was continued for 3 h. The reaction mixture was diluted with DCM, washed with water, brine, dried over MgSO$_4$ and concentrated. The residue was purified by preparative HPLC. The fractions were evaporated to dryness, the residue was dissolved in DCM, dried over MgSO$_4$ and concentrated. The remaining solid was triturated with diethyl ether, filtered, washed with diethyl ether and dried under vacuum at 50° C. to afford 8-[1-(3,5-difluorophenyl) pyrrolidin-2-yl]-2-morpholino-6-(1-oxo-1,4-thiazinane-4-carbonyl)chromen-4-one (87 mg, 57%) as a pale beige solid.

Mass Spectrum: m/z [M+H]+=558.

Proton NMR Spectrum: (DMSO-d6) 1.75-1.86 (m, 1H), 1.98-2.08 (m, 2H), 2.14 (bs, 0.5H), 2.51-2.58 (m partially hidden by DMSO-d5, 1H), 2.64 (bs, 1H), 2.81 (bs, 1.5H), 2.98 (bs, 1H), 3.27 (bs, 1H), 3.40 (bs, 1H), 3.49-3.65 (m, 5H), 3.64-3.83 (m, 6H), 4.21 (bs, 0.5H), 4.34 (bs, 0.5H), 5.25 (d, 1H), 5.62 (s, 1H), 6.13 (d, 2H), 6.34 (t, 1H), 7.18 (s, 1H), 7.87 (d, 1H)

EXAMPLE 1.05

6-(azetidine-1-carbonyl)-8-[(2R)-(1-(3,5-difluorophenyl)pyrrolidin-2-yl)]-2-morpholino-4H-chromen-4-one

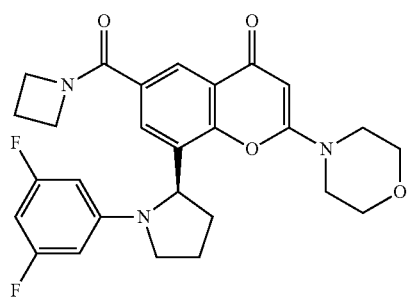 [SMILES: O=C(c1cc([C@H]2CCCN2c2cc(F)cc(F)c2)c2oc(N3CCOCC3)cc(=O)c2c1)N1CCC1]

TBTU (211 mg, 0.66 mmol) was added to a stirred solution of 8-[(2R)-1-(3,5-difluorophenyl)pyrrolidin-2-yl]-2-morpholino-4-oxo-chromene-6-carboxylic acid (150 mg, 0.33 mmol, >98% enantiomeric purity, see Example 1.03b for details of preparation) DIPEA (0.229 mL, 1.31 mmol) dissolved in CHCl$_3$ (2 mL) under nitrogen. The resulting solution was stirred at room temperature for 30 min. Azetidine hydrochloride (61.5 mg, 0.66 mmol) was added and the reaction mixture was stirred at 50° C. for 2-3 h. The solution was cooled to room temperature, quenched with a 10% aqueous citric acid solution and extracted with dichloromethane. The combined organic phases were washed with a saturated aqueous solution of sodium hydrogencarbonate, brine, dried over MgSO$_4$ and concentrated. The crude product was purified by flash chromatography on silica gel eluting with 0 to 10% methanol in EtAc/DCM (1/1). The solvent was evaporated to dryness, the dry film was triturated in diethyl ether and the precipitate was collected by filtration, washed with diethyl ether and dried to a constant weight, to give 6-(azetidine-1-carbonyl)-8-[(2R)-(1-(3,5-difluorophenyl)pyrrolidin-2-yl)]-2-morpholino-4H-chromen-4-one (126 mg, 0.254 mmol, 77%) as a solid.

Mass Spectrum: m/z [M+H]+=496.

Proton NMR Spectrum: (DMSO-d6) 1.74-1.88 (m, 1H), 1.97-2.08 (m, 2H), 2.13-2.24 (m, 2H), 2.43-2.51 (m partially hidden by DMSO-d5, 1H), 3.33-3.39 (m partially hidden by H2O, 1H), 3.49-3.66 (m, 4H), 3.70-3.81 (m, 5H), 3.93-4.09 (m, 4H), 5.25 (d, 1H), 5.62 (s, 1H), 6.15 (d, 2H), 6.33 (t, 1H), 7.30 (d, 1H), 8.04 (d, 1H)

EXAMPLE 1.06

8-[(2R)-(1-(3-fluorophenyl)pyrrolidin-2-yl)]-N,N-dimethyl-2-morpholino-4-oxo-4H-chromene-6-carboxamide

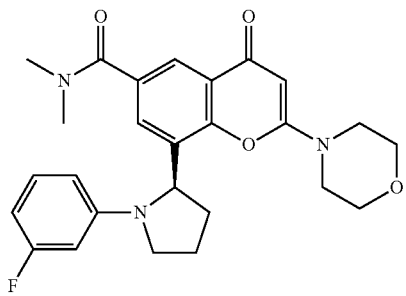 [SMILES: CN(C)C(=O)c1cc([C@H]2CCCN2c2cccc(F)c2)c2oc(N3CCOCC3)cc(=O)c2c1]

TSTU (429 mg, 1.34 mmol) was added in one portion to a stirred suspension of 8-[(2R)-1-(3-fluorophenyl)pyrrolidin-2-yl]-2-morpholino-4-oxo-chromene-6-carboxylic acid (488 mg, 1.11 mmol, >98% enantiomeric purity), dimethylamine hydrochloride (127 mg, 1.56 mmol) and DIPEA (0.582 mL, 3.34 mmol) dissolved in DCM (5 mL) at room temperature under nitrogen. The resulting suspension was stirred at room temperature for 20 min. The reaction mixture was quenched with water and extracted with DCM (1×40 mL). The organic phase was dried over MgSO₄ and concentrated to afford the crude product as a yellow foam. The crude product was purified by flash chromatography on silica gel eluting with 0 to 10% MeOH in EtAc. The solvent was evaporated to dryness, the foam was triturated in diethyl ether (10 mL), the resulting solid was filtered and dried under reduced pressure to afford 8-[(2R)-(1-(3-fluorophenyl)pyrrolidin-2-yl]-N,N-dimethyl-2-morpholino-4-oxo-4H-chromene-6-carboxamide (276 mg, 53%) as a yellow solid.

Mass Spectrum: m/z [M+H]+=466.

Proton NMR Spectrum: (DMSO-d6) 1.78-1.92 (m, 1H), 1.96-2.09 (m, 2H), 2.46-2.56 (m partially hidden by DMSO-d5, 1H), 2.68 (s, 3H), 2.90 (s, 3H), 3.33-3.42 (m partially hidden by H2O, 1H), 3.50-3.66 (m, 4H), 3.70-3.81 (m, 5H), 5.23 (d, 1H), 5.61 (s, 1H), 6.21-6.29 (m, 2H), 6.36 (ddd, 1H), 7.09 (ddd, 1H), 7.14 (d, 1H), 7.80 (d, 1H)

The 8-[(2R)-(1-(3-fluorophenyl)pyrrolidin-2-yl)]-2-morpholino-4-oxo-4H-chromene-6-carboxylic acid used as starting material was made as follows:

Step 1

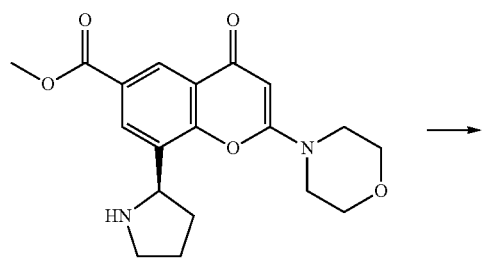

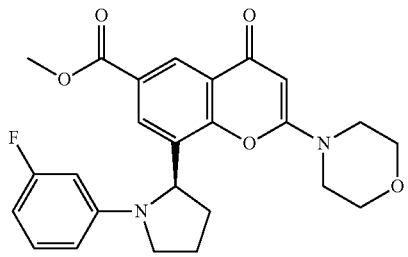

Diacetoxypalladium (3.3 mg, 0.01 mmol) was added to a stirred mixture of methyl 2-morpholino-4-oxo-8-[(2R)-pyrrolidin-2-yl]chromene-6-carboxylate (121 mg, 0.34 mmol), (9,9-dimethyl-9H-xanthene-4,5-diyl)bis(diphenylphosphine) (16.61 mg, 0.03 mmol), 1-bromo-3-fluorobenzene (0.047 mL, 0.42 mmol) and cesium carbonate (165 mg, 0.51 mmol) suspended in 1,4-dioxane (3.3 mL). The resulting suspension was degassed with argon and then stirred at 100° C. for 20 h. The reaction mixture was allowed to cool to room temperature, and the crude product was purified by flash chromatography on silica gel eluting with 0 to 7% propanol in DCM. The solvent was evaporated to dryness to afford methyl 8-[(2R)-(1-(3-fluorophenyl)pyrrolidin-2-yl)]-2-morpholino-4-oxo-4H-chromene-6-carboxylate (120 mg, 79%) as a yellow oil which solidified on standing. Mass Spectrum: m/z [M+H]+=453.

Step 4

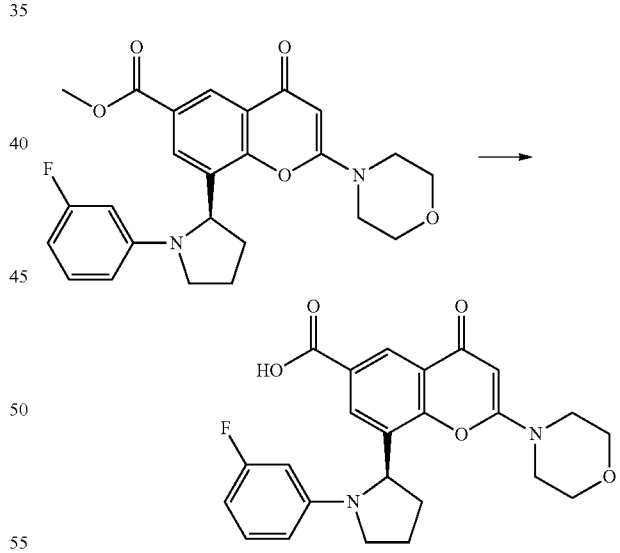

NaOH 2N (0.398 mL, 0.80 mmol) was added to methyl 8-[(2R)-(1-(3-fluorophenyl)pyrrolidin-2-yl)]-2-morpholino-4-oxo-4H-chromene-6-carboxylate (120 mg, 0.27 mmol) in a mixture of THF (2.4 mL) and MeOH (2.4 mL). The resulting solution was stirred at 25° C. over the weekend. HCl aq was added until pH ~2. The solvents were removed under vacuum and the yellow solid was collected by filtration, washed with Diethyl ether to give 8-[(2R)-(1-(3-fluorophenyl)pyrrolidin-2-yl)]-2-morpholino-4-oxo-4H-chromene-6-carboxylic acid (100 mg, 86%). Mass Spectrum: m/z [M+H]+=439.

EXAMPLE 1.07

8-[(2R)-(1-(3-fluorophenyl)pyrrolidin-2-yl)]-6-(morpholine-4-carbonyl)-2-morpholino-4H-chromen-4-one

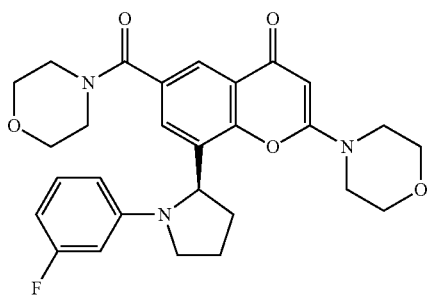 [SMILES: O=C(c1cc([C@H]2CCCN2c2cccc(F)c2)c2oc(N3CCOCC3)cc(=O)c2c1)N1CCOCC1]

TSTU (220 mg, 0.68 mmol) was added in one portion to a stirred suspension of 8-[(2R)-(1-(3-fluorophenyl)pyrrolidin-2-yl)]-2-morpholino-4-oxo-4H-chromene-6-carboxylic acid (250 mg, 0.57 mmol, >98% enantiomeric purity, see Example 1.06 for details of preparation), morpholine (0.075 mL, 0.86 mmol) and DIPEA (0.149 mL, 0.86 mmol) dissolved in DCM (5 mL) at room temperature under nitrogen. The resulting suspension was stirred at room temperature for 16 h. The reaction mixture was purified by preparative HPLC. The fractions were evaporated to dryness, the obtained foam was dissolved in DCM (0.5 mL) and diethyl ether (1 mL) was added. The resulting crystalline solid was collected by filtration and dried under vacuum to give 8-[(2R)-(1-(3-fluorophenyl)pyrrolidin-2-yl)]-6-(morpholine-4-carbonyl)-2-morpholino-4H-chromen-4-one (126 mg, 44%) as a white crystalline solid.

$[\alpha]^D_{20°}$: −15.2° (19.8 mg in 2 mL of acetonitrile).

Mass Spectrum: m/z [M+H]+=508.

Proton NMR Spectrum: (DMSO-d6) 1.81-1.93 (m, 1H), 1.97-2.10 (m, 2H), 2.50-2.59 (m partially hidden by DMSO-d5, 1H), 3.19-3.24 (m partially hidden by H2O, 1H), 3.34-3.42 (m, 4H), 3.44 (bs, 4H), 3.50-3.64 (m, 4H), 3.71-3.81 (m, 5H), 5.23 (d, 1H), 5.58 (s, 1H), 6.21-6.28 (m, 2H), 7.36 (ddd, 1H), 7.08 (dd, 1H), 7.10 (d, 1H), 7.82 (d, 1H)

EXAMPLE 1.08

6-(azetidine-1-carbonyl)-8-[(2R)-(1-(3-fluorophenyl)pyrrolidin-2-yl)]-2-morpholino-4H-chromen-4-one

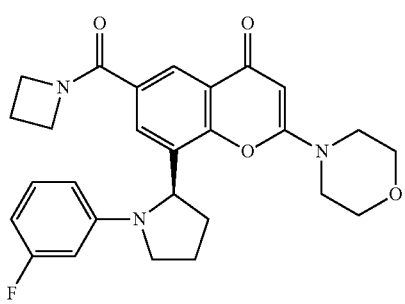

HATU (368 mg, 0.97 mmol) was added to a stirred solution of 8-[(2R)-(1-(3-fluorophenyl)pyrrolidin-2-yl)]-2-morpholino-4-oxo-4H-chromene-6-carboxylic acid (212 mg, 0.48 mmol >98% enantiomeric purity, see Example 1.06 for details of preparation) and DIPEA (0.674 mL, 3.87 mmol) dissolved in DCM (1 mL) under nitrogen. The resulting solution was stirred at room temperature for 1 h. Azetidine hydrochloride (271 mg, 2.90 mmol) was added and the mixture was stirred at room temperature for 15 h. The reaction mixture was purified by preparative HPLC. The fractions were evaporated to dryness to afford 6-(azetidine-1-carbonyl)-8-[(2R)-(1-(3-fluorophenyl)pyrrolidin-2-yl)]-2-morpholino-4H-chromen-4-one (28 mg, 12%) as a pale yellow foam.

Mass Spectrum: m/z [M+H]+=478.

Proton NMR Spectrum (CDCl3) 1.97-2.14 (m, 3H), 2.18-2.33 (m, 2H), 2.40-2.52 (m, 1H), 3.37-3.46 (m, 1H), 3.48-3.61 (m, 4H), 3.75-3.82 (m, 1H), 3.82-3-92 (m, 4H), 4.02-4.10 (m, 1H), 4.12-4.20 (m, 2H), 4.21-4.30 (m, 1H), 5.08 (d, 1H), 5.57 (s, 1H), 6.14 (ddd, 1H), 6.21 (dd, 1H), 6.37 (ddd, 1H), 7.08 (dd, 1H), 7.64 (d, 1H), 8.26 (d, 1H)

EXAMPLE 1.09

8-[(2R)-(1-(3,5-difluorophenyl)pyrrolidin-2-yl)]-6-(4-methylpiperazine-1-carbonyl)-2-morpholino-4H-chromen-4-one

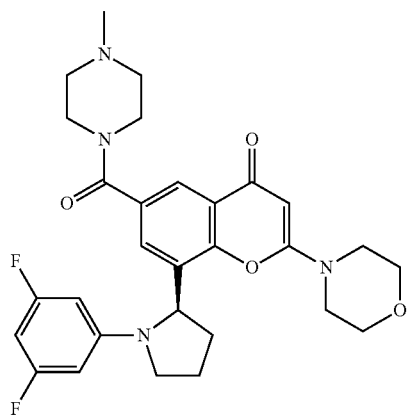 [SMILES: CN1CCN(C(=O)c2cc([C@H]3CCCN3c3cc(F)cc(F)c3)c3oc(N4CCOCC4)cc(=O)c3c2)CC1]

8-[(2R)-1-(3,5-difluorophenyl)pyrrolidin-2-yl]-2-morpholino-4-oxo-chromene-6-carboxylic acid (see Example 1.03b for preparation, 97 mg, 0.21 mmol), DIPEA (0.185 mL, 1.06 mmol) and 1-methylpiperazine (0.047 mL, 0.43 mmol) were mixed at room temperature in DCM (3 mL). N-propylphosphonic acid anhydride, cyclic trimer (50 wt % solution in EtAc) (0.633 mL, 1.08 mmol) was then added and the reaction mixture was stirred at 25° C. for 1 hour. The reaction mixture was purified by preparative HPLC to afford 8-[(2R)-(1-(3,5-difluorophenyl)pyrrolidin-2-yl)]-6-(4-methylpiperazine-1-carbonyl)-2-morpholino-4H-chromen-4-one (67 mg, 59%) as a white foam.

Mass Spectrum: m/z [M+H]+=539.

Proton NMR Spectrum: (DMSO-d6): 1.76-1.89 (m, 2H), 1.98-2.07 (m, 2H), 2.11 (s, 3H), 2.13-2.22 (m, 2H), 2.36 (br, 2H), 2.93-3.13 (br, 2H), 3.35-3.42 (m partially hidden by H2O, 2H), 3.51-3.67 (m, 4H), 3.70-3.78 (m, 6H), 5.26 (d, 1H), 5.62 (s, 1H), 6.14 (d, 2H), 6.33 (m, 1H), 7.02 (d, 1H), 7.78 (d, 1H)

EXAMPLE 1.10

8-[(2R)-(1-(3-fluorophenyl)pyrrolidin-2-yl)]-6-(4-methylpiperazine-1-carbonyl)-2-morpholino-4H-chromen-4-one

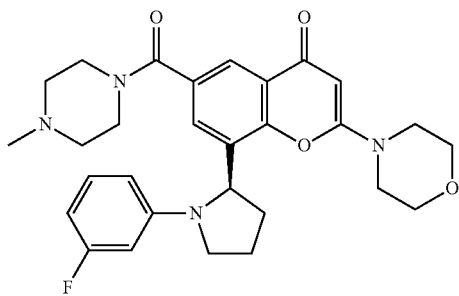 [SMILES: CN1CCN(C(=O)c2cc([C@H]3CCCN3c3cccc(F)c3)c3oc(N4CCOCC4)cc(=O)c3c2)CC1]

8-[(2R)-(1-(3-fluorophenyl)pyrrolidin-2-yl)]-2-morpholino-4-oxo-4H-chromene-6-carboxylic acid (see Example 1.06 for preparation; 100 mg, 0.23 mmol) was reacted with 1-methylpiperazine (0.076 ml, 0.68 mmol) using a procedure similar to the one described in example 1.00 to afford 8-[(2R)-(1-(3-fluorophenyl)pyrrolidin-2-yl)]-6-(4-methylpiperazine-1-carbonyl)-2-morpholino-4H-chromen-4-one (39 mg, 33%).

Mass Spectrum: m/z [M+H]+=521.

Proton NMR Spectrum: (CDCl$_3$): 1.97-2.13 (m, 4H), 2.24 (br s, 3H), 2.29-2.54 (m, 4H), 3.00-3.28 (m, 2H), 3.40-3.47 (m, 1H), 3.49-3.61 (m, 4H), 3.69-3.81 (m, 3H), 3.81-3.94 (m, 4H), 5.10 (d, 1H), 5.57 (s, 1H), 6.12 (d, 1H), 6.20 (d, 1H), 6.33-6.41 (m, 1H), 7.06-7.11 (m, 1H), 7.26 (s hidden by chloroform, 1H), 8.12 (d, 1H)

EXAMPLE 1.11

8-[(2R)-(1-(3-methoxyphenyl)pyrrolidin-2-yl)]-6-(morpholine-4-carbonyl)-2-morpholino-4H-chromen-4-one

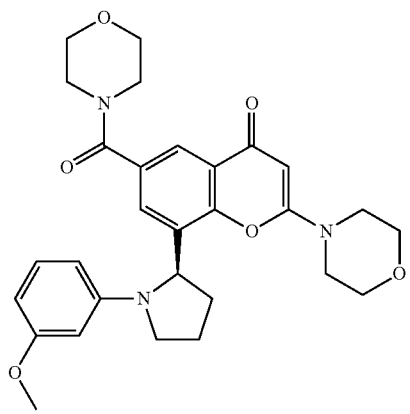 [SMILES: COc1cccc(N2CCC[C@@H]2c2cc(C(=O)N3CCOCC3)cc3c(=O)cc(N4CCOCC4)oc23)c1]

8-[(2R)-(1-(3-methoxyphenyl)pyrrolidin-2-yl)-2-morpholino-4-oxo-4H-chromene-6-carboxylic acid (63 mg, 0.14 mmol) was reacted with morpholine (0.12 mL, 0.14 mmol) using a procedure similar to the one described in example 1.04 to give 8-[(2R)-(1-(3-methoxyphenyl)pyrrolidin-2-yl)]-6-(morpholine-4-carbonyl)-2-morpholino-4H-chromen-4-one (37 mg, 51%) as a white foam.

Mass Spectrum: m/z [M+H]+=520.

Proton NMR Spectrum: (DMSO-d$_6$): 1.78-1.91 (m, 1H), 1.95-2.06 (m, 2H), 2.50-2.56 (m partially hidden by DMSO-d$_5$, 1H), 2.96-3.26 (m, 4H), 3.35-3.42 (m, 2H), 3.50-3.62 (m, 6H), 3.63 (s, 3H), 3.71-3.79 (m, 6H), 5.20 (d, 1H), 5.61 (s, 1H), 5.94-5.98 (m, 1H), 6.01 (dd, 1H), 6.21 (dd, 1H), 6.99 (dd, 1H), 7.12 (d, 1H), 7.81 (d, 1H) MMA-04957-98-01-109269

The 8-(1-(3-methoxyphenyl)pyrrolidin-2-yl)-2-morpholino-4-oxo-4H-chromene-6-carboxylic acid used as starting material was made using procedures similar to the ones described in example 1.05, with 1-bromo-3-methoxybenzene being used in place of 1-bromo-3-fluorobenzene:

Step 1

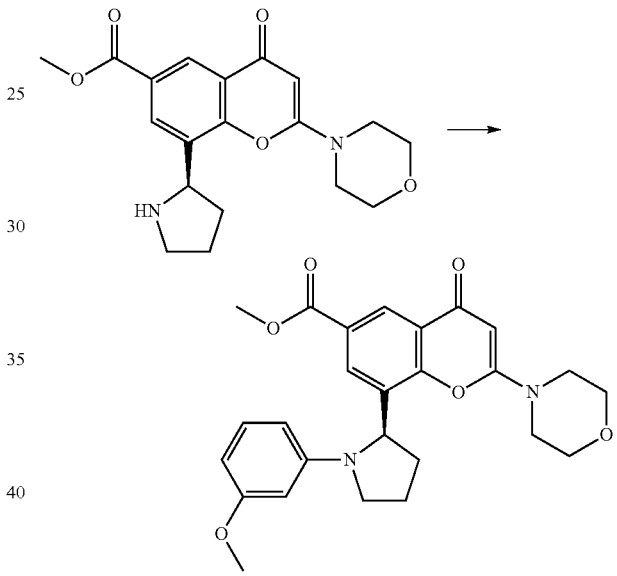

Methyl 2-morpholino-4-oxo-8-[(2R)-pyrrolidin-2-yl]chromene-6-carboxylate, preparation described in Example 1.03b, 125 mg, 0.35 mmol) was reacted with 1-bromo-3-methoxybenzene (0.049 ml, 0.38 mmol) using a procedure similar to that described in Example 1.0 to afford methyl 8-[(2R)-(1-(3-methoxyphenyl)pyrrolidin-2-yl)]-2-morpholino-4-oxo-4H-chromene-6-carboxylate (90 mg, 56%) as a yellow gum. Mass Spectrum: m/z [M+H]+=465.

Step 2

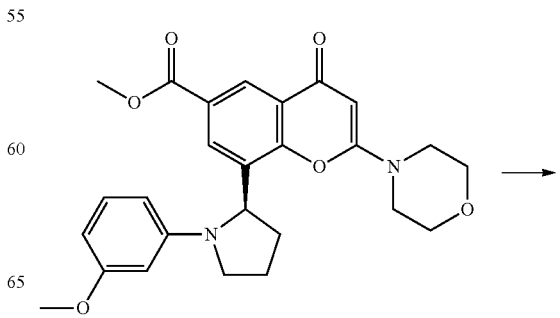

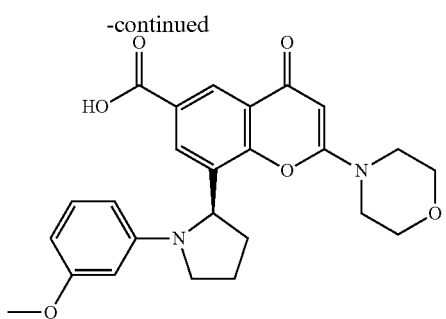

Methyl 8-[(2R)-(1-(3-methoxyphenyl)pyrrolidin-2-yl)]-2-morpholino-4-oxo-4H-chromene-6-carboxylate (90 mg, 0.19 mmol) was reacted with sodium hydroxide (38.7 mg, 0.97 mmol) to give 8-[(2R)-(1-(3-methoxyphenyl)pyrrolidin-2-yl)]-2-morpholino-4-oxo-4H-chromene-6-carboxylic acid (64 mg, 73%) as a beige solid. Mass Spectrum: m/z [M+H]+ =451.

EXAMPLE 1.12

8-(1-(4-fluorophenyl)pyrrolidin-2-yl)-6-(morpholine-4-carbonyl)-2-morpholino-4H-chromen-4-one

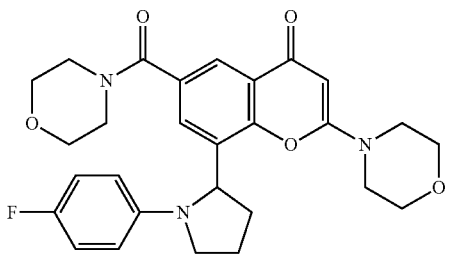 [SMILES: O=C(c1cc(C2CCCN2c2ccc(F)cc2)c2oc(N3CCOCC3)cc(=O)c2c1)N1CCOCC1]

Diacetoxypalladium (6.79 mg, 0.03 mmol) was added to a stirred mixture of 6-(morpholine-4-carbonyl)-2-morpholino-8-(pyrrolidin-2-yl)-4H-chromen-4-one (250 mg, 0.60 mmol), biphenyl-2-yldicyclohexylphosphine (21 mg, 0.06 mmol), 1-bromo-4-fluorobenzene (0.083 ml, 0.76 mmol) and cesium carbonate (296 mg, 0.91 mmol) dissolved in 1,4-dioxane (5 mL). The resulting suspension was degassed with argon and then stirred at 100° C. for 15 h. The reaction mixture was purified by preparative HPLC. The fractions containing the desired compound were evaporated to dryness to afford 8-(1-(4-fluorophenyl)pyrrolidin-2-yl)-6-(morpholine-4-carbonyl)-2-morpholino-4H-chromen-4-one (140 mg, 46%) as a gum.

Mass Spectrum: m/z [M+H]+=508.

Proton NMR Spectrum (DMSO-$d_6$): 1.79-1.92 (m, 1H), 1.95-2.07 (m, 2H), 2.52-2.57 (m partially hidden by DMSO-$d_5$, 1H), 2.92-3.28 (m, 4H), 3.39-3.67 (m, 1H), 3.48-3.67 (m, 6H), 3.70-3.80 (m, 6H), 5.17 (d, 1H), 5.61 (s, 1H), 6.41 (dd, 2H), 6.95 (dd, 2H), 7.13 (d, 1H), 7.81 (d, 1H).

The above racemic mixture was purified via chiral HPLC:

| Instrument | Gilson Prep (200 ml heads) |
| Column | Merck 50 mm 20 μm Chiralpak IC |
| Eluent | MeCN/MeOH/TEA 90/10/0.1 |
| Flow | 100 ml/min |
| Wavelength | 254 nm |
| Sample Conc. | 88 mg/30 ml in MeCN |
| Injection volume | 30 ml |
| Run Time | 40 mins |

Samples were both obtained as clear thin films, which when triturated with diethylether gave cream white solids. These materials were dried overnight in vacuo at 40° C.

1st eluted enantiomer: 30 mg (99% enantiomeric purity) example 1.12a

2nd eluted enantiomer: 26 mg (99% enantiomeric purity) example 1.12b

EXAMPLE 1.12a 8-(1-(4-fluorophenyl)pyrrolidin-2-yl)-6-(morpholine-4-carbonyl)-2-morpholino-4H-chromen-4-one (enantiomer 1)

Analysis Conditions:

| Instrument | HP1100 |
| Column | 3 μm Chiralpak IC 4.6 × 50 mm |
| Eluent | MeCN/MeOH/TEA 90/10/0.1 |
| Flow | 1 ml/min |
| Wavelength | 254 nm |
| Sample Conc | 1 mg/ml in EtOH |
| Injection volume | 10 ul |
| Run Time | 5 mins |

1st eluting enantiomer: example 1.12a retention time 2.92 min, 99.7% pure.

EXAMPLE 1.12b 8-(1-(4-fluorophenyl)pyrrolidin-2-yl)-6-(morpholine-4-carbonyl)-2-morpholino-4H-chromen-4-one (enantiomer 2)

Analysis Conditions:

| Instrument | HP1100 |
| Column | 3 μm Chiralpak IC 4.6 × 50 mm |
| Eluent | MeCN/MeOH/TEA 90/10/0.1 |
| Flow | 1 ml/min |
| Wavelength | 254 nm |
| Sample Conc | 1 mg/ml in EtOH |
| Injection volume | 10 ul |
| Run Time | 5 mins |

2nd eluting enantiomer: example 1.12b retention time 3.56 min, 99.6% pure.

The 6-(morpholine-4-carbonyl)-2-morpholino-8-(pyrrolidin-2-yl)-4H-chromen-4-one used as starting material was made as follows:—

Step 1

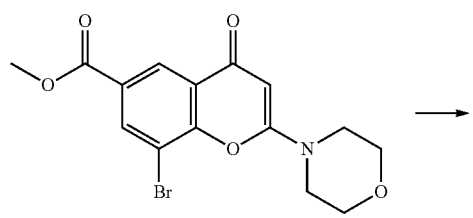

NaOH 2N (40.7 mL, 81.48 mmol) was added to methyl 8-bromo-2-morpholino-4-oxo-4H-chromene-6-carboxylate (10 g, 27.2 mmol) in a mixture of methanol (225 mL) and DCM (75 mL). The slurry was stirred at room temperature for 16 h. The solvents were evaporated, water (150 mL) was added to the slurry, the solution was cooled down to 0° C. and HCl 6N (15 mL, 89.6 mmol) solution was added dropwise to the reaction mixture until pH ~3.4. The formed solid was collected by filtration, washed with water (3×50 mL), then toluene (3×50 mL) followed by Diethyl ether (3×50 mL), dried at 55° C. under vacuum over P2O5 to afford 8-bromo-2-morpholino-4-oxo-4H-chromene-6-carboxylic acid (9.47 g, 98%) as a beige solid. The crude product was used without further purification.

Mass Spectrum: m/z [M+H]+=354.

Step 2

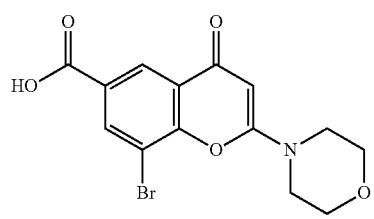

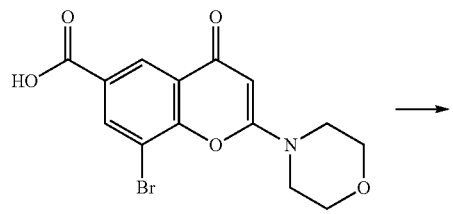

N-propylphosphonic acid anhydride, cyclic trimer (50 wt % solution in EtAc) (8.57 ml, 14.68 mmol) was added at room temperature in one portion to a stirred solution of 8-bromo-2-morpholino-4-oxo-4H-chromene-6-carboxylic acid (2 g, 5.65 mmol), DIPEA (4.9 mL, 28.2 mmol) and morpholine (0.543 mL, 6.2 mmol) in DCM (14 mL). The mixture was stirred at room temperature for 1 h then water (1 mL) was then added. The reaction mixture was stirred for 15 mins and extracted with DCM. The combined organic layers were washed with water; the organic layer was washed with brine, dried over magnesium sulfate and concentrated to afford 8-bromo-6-(morpholine-4-carbonyl)-2-morpholino-4H-chromen-4-one (1.90 g, 79%) as a beige solid. Mass Spectrum: m/z [M+H]+=423.

Step 3

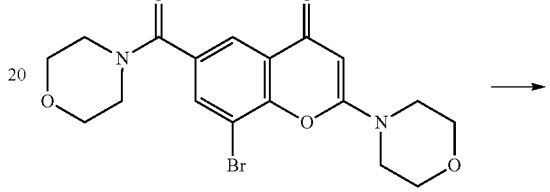

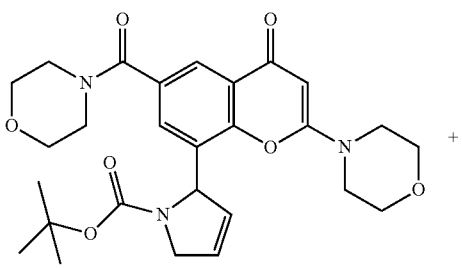

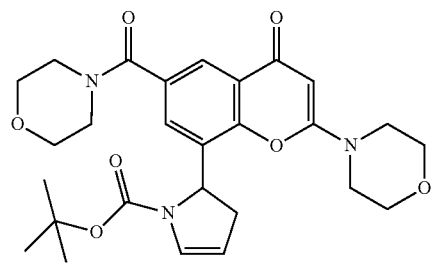

Diacetoxypalladium (0.095 g, 0.42 mmol) was added to a stirred suspension of 8-bromo-6-(morpholine-4-carbonyl)-2-morpholino-4H-chromen-4-one (1.79 g, 4.23 mmol), tert-butyl 2,3-dihydro-1H-pyrrole-1-carboxylate (1.431 g, 8.46 mmol), triphenylphosphine (0.222 g, 0.85 mmol) and potassium acetate (1.245 g, 12.69 mmol) dissolved in DMF (24.88 ml) under nitrogen. The resulting suspension was degassed under nitrogen and was stirred at 100° C. for 16 h. The mixture was evaporated, adsorbed on silica gel and was purified by flash chromatography on silica gel eluting with 5 to 8% methanol in DCM. The solvent was evaporated to dryness to afford a mixture of tert-butyl 2-(6-(morpholine-4-carbonyl)-2-morpholino-4-oxo-4H-chromen-8-yl)-2,5-dihydro-1H-pyrrole-1-carboxylate and tert-butyl 2-(6-(morpholine-4-carbonyl)-2-morpholino-4-oxo-4H-chromen-8-yl)-2,3-dihydro-1H-pyrrole-1-carboxylate (2.20 g, 102%) as an orange oil. Mass Spectrum: m/z [M+H]+=512.

Step 4

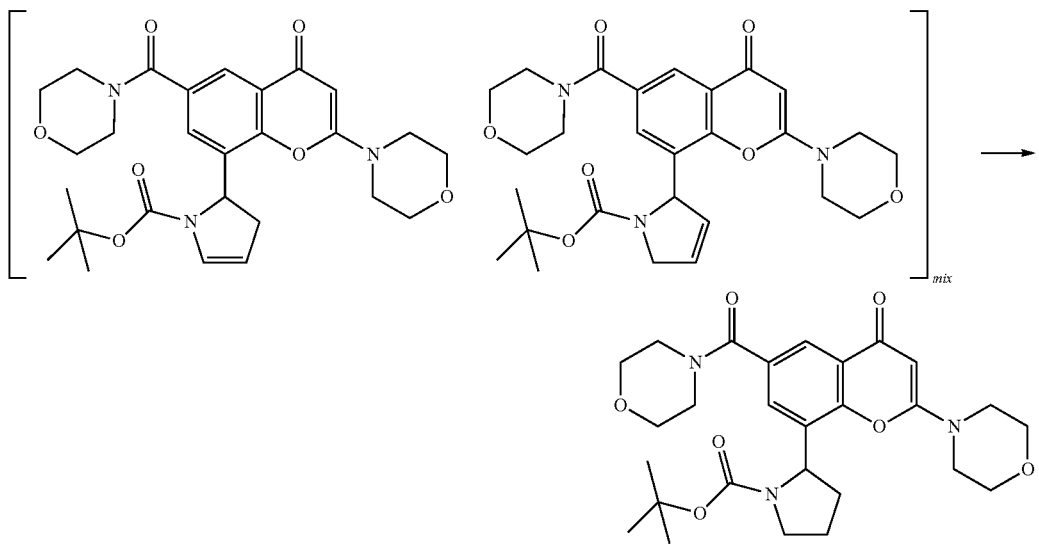

The above mixture of tert-butyl 2-(6-(morpholine-4-carbonyl)-2-morpholino-4-oxo-4H-chromen-8-yl)-2,3-dihydro-1H-pyrrole-1-carboxylate compound and tert-butyl 2-(6-(morpholine-4-carbonyl)-2-morpholino-4-oxo-4H-chromen-8-yl)-2,5-dihydro-1H-pyrrole-1-carboxylate (1:1) (2.1 g, 2.05 mmol) and platinum(IV) oxide (0.093 g, 0.41 mmol) in ethanol (30 ml) was hydrogenated under 1.2 atm at room temperature for 4 h. The resulting solution was filtered and the filtrate was concentrated to dryness to afford the crude tert-butyl 2-(6-(morpholine-4-carbonyl)-2-morpholino-4-oxo-4H-chromen-8-yl)pyrrolidine-1-carboxylate (1.60 g, 76%) as an orange solid. Mass Spectrum: m/z [M+H]+=514.

Step 5

HCl 4M (9.74 mL, 39 mmol) was added to a stirred solution of tert-butyl 2-(6-(morpholine-4-carbonyl)-2-morpholino-4-oxo-4H-chromen-8-yl)pyrrolidine-1-carboxylate (2 g, 3.89 mmol) dissolved in DCM (15 mL) at r.t and stirred over the week-end. After concentration, DCM (15 mL) and MeOH (15 mL) were added, followed by a solution of 10% methanolic ammonia (7 N) in DCM (10 mL). The crude product was adsorbed on silica gel and purified by flash chromatography on silica gel eluting with 0 to 10% methanol in DCM. The solvent was evaporated to dryness to give a solid and dried under vacuum to give 6-(morpholine-4-carbonyl)-2-morpholino-8-(pyrrolidin-2-yl)-4H-chromen-4-one (1.0 g, 62%) as a beige solid. Mass Spectrum: m/z [M+H]+=414.

EXAMPLE 2.00

8-(1-(3-fluorophenyl)pyrrolidin-2-yl)-N,N-dimethyl-2-morpholino-4-oxo-4H-chromene-6-carboxamide

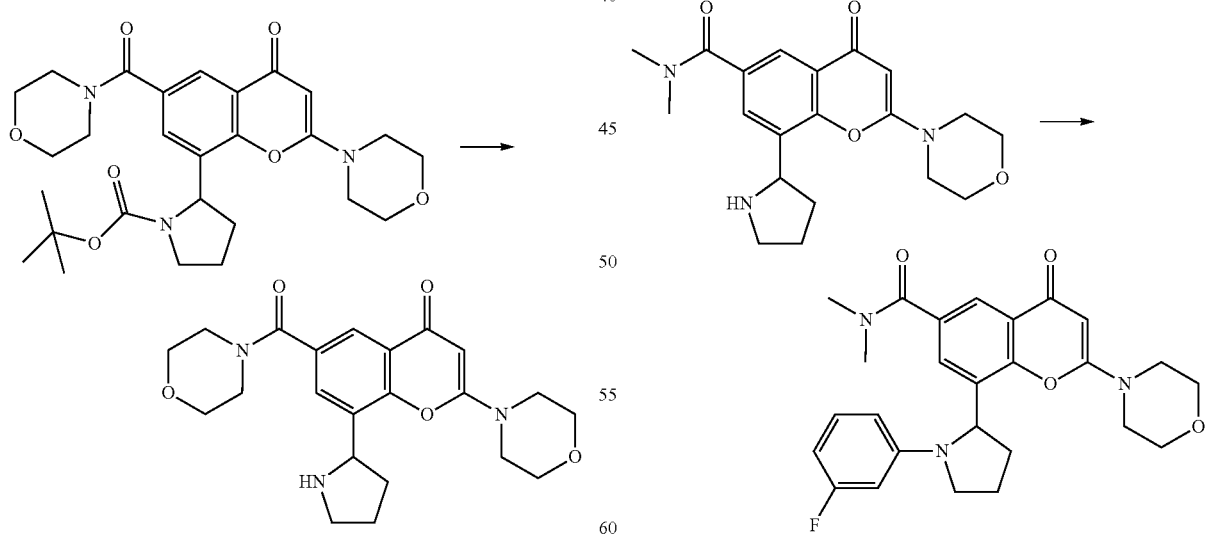

Diacetoxypalladium (3.9 mg, 0.02 mmol) was added to a stirred mixture of N,N-dimethyl-2-morpholino-4-oxo-8-(pyrrolidin-2-yl)-4H-chromene-6-carboxamide (130 mg, 0.35 mmol), 1-bromo-3-fluorobenzene (0.049 ml, 0.44 mmol), (9,9-dimethyl-9H-xanthene-4,5-diyl)bis(diphenylphosphine) (20.25 mg, 0.03 mmol) and cesium carbonate (171 mg, 0.52 mmol) dissolved in 1,4-dioxane (4 mL). The resulting suspension was degassed with argon and stirred at 100° C. for 16 h then cooled to room temperature, filtered and concentrated. The crude product was dissolved in DMA (2 mL) and purified by preparative HPLC. The fractions containing the desired compound were evaporated to dryness to afford 8-(1-(3-fluorophenyl)pyrrolidin-2-yl)-N,N-dimethyl-2-morpholino-4-oxo-4H-chromene-6-carboxamide (67 mg, 41%) as a solid.

Mass Spectrum: m/z [M+H]+=466.

Proton NMR Spectrum: (DMSO-d6) 1.78-1.90 (m, 1H), 1.97-2.08 (m, 2H), 2.52-2.60 (m partially hidden by DMSO-d5, 1H), 2.68 (s, 3H), 2.90 (s, 3H), 3.33-3.39 (m partially hidden by H2O, 1H), 3.50-3.57 (m, 2H), 3.57-3.64 (m, 2H), 3.71-3.79 (m, 5H), 5.23 (d, 1H), 5.61 (s, 1H), 6.22-6.29 (m, 2H), 6.37 (ddd, 1H), 7.09 (dd, 1H), 7.14 (d, 1H), 7.80 (d, 1H).

The N,N-dimethyl-2-morpholino-4-oxo-8-(pyrrolidin-2-yl)-4H-chromene-6-carboxamide used as starting material was made as follows:—

Step 1

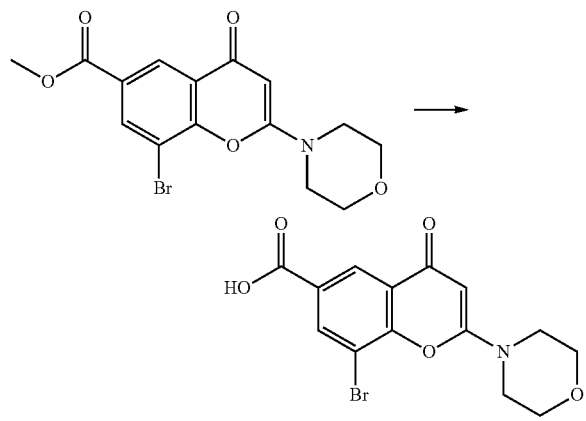

Sodium hydroxide (32.6 mL, 65.19 mmol) was added to a stirred suspension of methyl 8-bromo-2-morpholino-4-oxo-4H-chromene-6-carboxylate (8 g, 21.73 mmol) dissolved in MeOH (42 mL) and THF (21 mL) at 0° C. The resulting suspension was stirred at room temperature for 1 h. MeOH (60 mL), THF (10 mL) and water (10 mL) were then added to help stirring. Upon completion, the reaction was cooled to 0° C. and HCl 2N was added to the suspension until pH 2. The solid was collected by filtration, washed with water, AcOEt, diethyl ether and dried with P2O5 under vacuum at 50° C. to give 8-bromo-2-morpholino-4-oxo-4H-chromene-6-carboxylic acid (7.0 g, 91%). Mass Spectrum: m/z [M+H]+=354.

Step 2

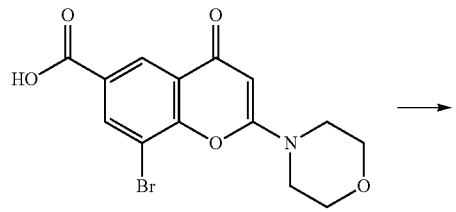

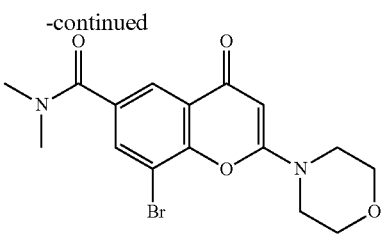

TSTU (6.55 g, 21.74 mmol) was added to a stirred solution of 8-bromo-2-morpholino-4-oxo-4H-chromene-6-carboxylic acid (7 g, 19.77 mmol) and DIPEA (3.79 mL, 21.74 mmol) dissolved in DCM (100 mL) under nitrogen. The resulting suspension was stirred at room temperature for 4 h. More TSTU (6.55 g, 21.74 mmol) and DIPEA (3.79 mL, 21.74 mmol) were added and stirring was pursued for a further 16 h. The reaction mixture was quenched with a saturated aqueous solution of sodium hydrogencarbonate and extracted with DCM and a little MeOH. The combined organic phases were dried over MgSO4, concentrated and purified by flash chromatography on silica gel eluting with 3 to 5% MeOH in DCM. The solvent was evaporated to dryness to afford 8-bromo-N,N-dimethyl-2-morpholino-4-oxo-4H-chromene-6-carboxamide (7.70 g, 102%) as a beige solid. Mass Spectrum: m/z [M+H]+=381.

8-bromo-N,N-dimethyl-2-morpholino-4-oxo-4H-chromene-6-carboxamide was also synthesised on a large scale according to the following procedure. Potassium hydroxide (39.8 mL, 518.37 mmol) was added at a constant rate over 30 min to methyl 8-bromo-2-morpholino-4-oxo-4H-chromene-6-carboxylate (99.3 g, 259.18 mmol) in water (572 mL) at 22° C. in a 3 litre jacketed vessel equipped with an overhead air stirrer (vessel 1). The resulting mixture was stirred at 22° C. for 4 h. Water (286 mL) was added in one portion and the mixture stirred at 22° C. for 2 h until saponification was complete. The reaction was filtered to remove insoluble particulates, water (95 mL) was charged to the vessel as a screen filter wash and the combined filtrates transferred into a 3 litre jacketed vessel (vessel 1). A solution of dimethylamine hydrochloride (64.4 g, 777.55 mmol) in water (191 mL) was added to vessel 1 and agitation continued.

In a separate 2 Litre jacketed vessel (vessel 2), 2-chloro-4,6-dimethoxy-1,3,5-triazine (208 g, 1.17 mol) and water (978 mL) were charged to vessel 2 and the temperature adjusted to approximately 8° C. 4-Methylmorpholine (214 mL, 1.94 mol) was charged at a rate to maintain the contents of vessel 2<12° C. and the contents agitated for 2.5 h at 12° C.

The contents of vessel 2 were transferred at a constant rate over 3.5 h to vessel 2, via a dropping funnel, and agitated at 22° C. for 6 h. The reaction mixture was then subjected to the following temperature cycling regime.

| Heat/cool operation for vessel 2 contents | Duration of operation (min) |
|---|---|
| Heat to 75° C. | 30 |
| Hold at 75° C. | 60 |
| Cool to 60° C. | 90 |
| Hold at 60° C. | 30 |
| Heat to 75° C. | 30 |
| Hold at 75° C. | 60 |
| Cool to 60° C. | 90 |
| Hold at 60° C. | 30 |
| Heat to 75° C. | 30 |
| Hold at 75° C. | 60 |
| Cool to 20° C. | 400 |
| Hold at 20° C. | 60 |

The reaction mixture was filtered and the solid washed with water (381 mL). The solid was washed with water (381 mL)

and dried in vacuo at 50° C. to give 8-bromo-N,N-dimethyl-2-morpholino-4-oxo-chromene-6-carboxamide (78 g, 78%) as a beige solid.

Mass Spectrum: m/z [M+H] 381.

Proton NMR Spectrum: (400 MHz, DMSO, 30° C.) 2.93 (3H, br. s), 2.99 (3H, br. s), 3.57-3.60 (4H, m), 3.74-3.76 (4H, m), 5.61 (1H, s), 7.87 (1H, d, J=1.9 Hz), 7.99 (1H, d, J=1.9 Hz);

Step 3

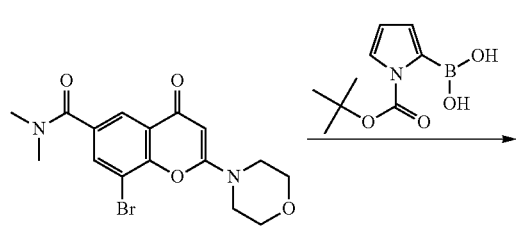

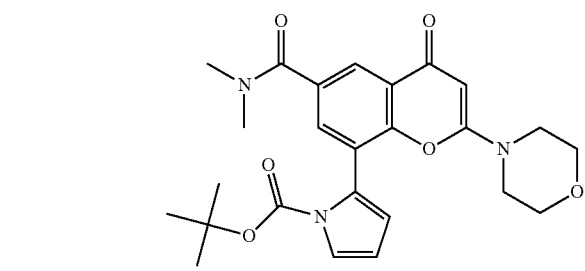

Bis(triphenylphosphine) palladium (II) chloride (0.116 g, 0.17 mmol) was added in one portion to a stirred slurry of 8-bromo-N,N-dimethyl-2-morpholino-4-oxo-4H-chromene-6-s carboxamide (3.15 g, 8.26 mmol), 1-(tert-butoxycarbonyl)-1H-pyrrol-2-ylboronic acid (2.1 g, 9.92 mmol) and sodium carbonate (2.63 g, 24.79 mmol) in DME (50 mL) and water (10 mL). The resulting mixture was stirred at 80° C. for 8 h. After cooling, water was added to the reaction mixture and extracted with DCM. The combined organic phases were washed with water and brine, dried over sodium sulfate and concentrated. The crude product was purified by flash chromatography on silica gel eluting with 5% MeOH in DCM. The solvents were evaporated to dryness to afford tert-butyl 2-(6-(dimethylcarbamoyl)-2-morpholino-4-oxo-4H-chromen-8-yl)-1H-pyrrole-1-carboxylate (2.40 g, 62%). Mass Spectrum: m/z [M+H]+=468.

Step 4

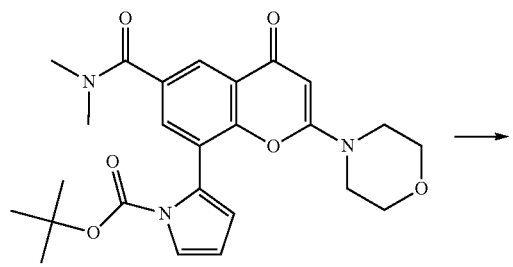

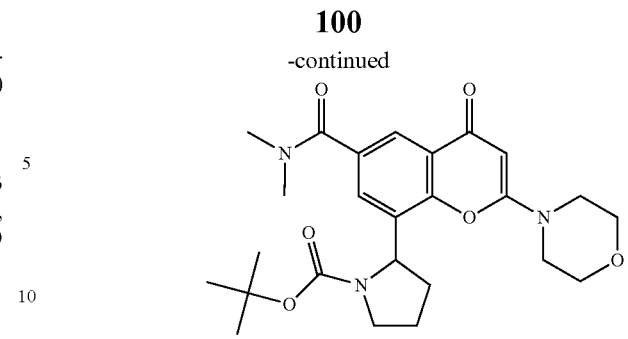

A solution of tert-butyl 2-(6-(dimethylcarbamoyl)-2-morpholino-4-oxo-4H-chromen-8-yl)-1H-pyrrole-1-carboxylate (0.6 g, 1.28 mmol) in MeOH (10 mL) was hydrogenated over 5% Rh/Al$_2$O$_3$ (NanoThales CatCart cartridge, product ID THS 02118) with the H-Cube (Continuous flow hydrogenation apparatus HC-2.5S from THALES Nanotechnology Inc. Budapest H-1031; Zahony u.7.; Hungaria) at 10 bars, 50° C. and a flow rate of 1 mL/min. for 3.5 h with continuous recycling. The cartridge was replaced by a 10% Pd/c cartridge and hydrogenation was pursued for 6 h at 60 bars and 60° C. The mixture was evaporated to dryness to give a solid which was triturated in diethyl ether, filtered and dried under vacuum at 50° C. to afford pure tert-butyl 2-(6-(dimethylcarbamoyl)-2-morpholino-4-oxo-4H-chromen-8-yl)pyrrolidine-1-carboxylate (0.30 g, 50%) as a white solid. The crude product was used as such for the next step. Mass Spectrum: m/z [M+H]+=472.

Step 5

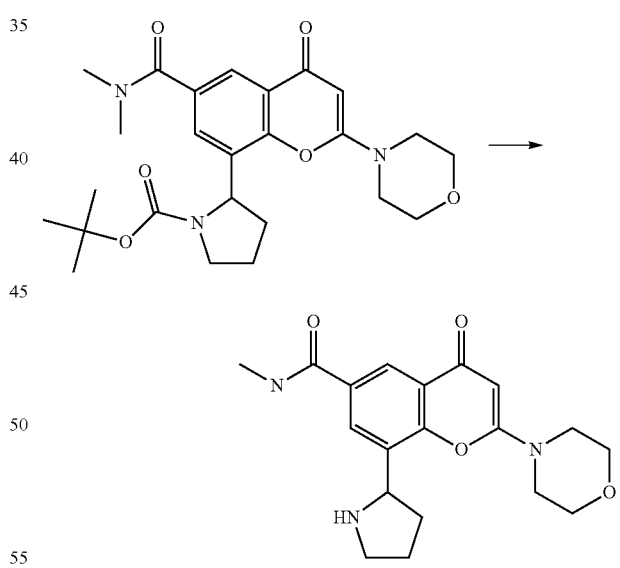

HCl (4.50 mL, 18 mmol, 4M solution) was added to a stirred solution of tert-butyl 2-(6-(dimethylcarbamoyl)-2-morpholino-4-oxo-4H-chromen-8-yl)pyrrolidine-1-carboxylate (850 mg, 1.80 mmol) dissolved in DCM (10 mL) at room temperature and stirred for 8 h. After evaporation of the volatile, DCM (5 mL) and MeOH (5 mL) were added followed by 10% methanolic ammonia (7 N, 5 mL) in DCM. The solid was filtered, washed with a 1:1 mixture of DCM and MeOH. The solvent was evaporated to dryness to afford after trituration with diethyl diethyl ether, N,N-dimethyl-2-morpholino-4-oxo-8-(pyrrolidin-2-yl)-4H-chromene-6-carboxamide (675 mg, 101%) as a pale beige solid. Mass Spectrum: m/z [M+H]+=372.

EXAMPLE 2.01

8-(1-(3-methoxyphenyl)pyrrolidin-2-yl)-N,N-dimethyl-2-morpholino-4-oxo-4H-chromene-6-carboxamide

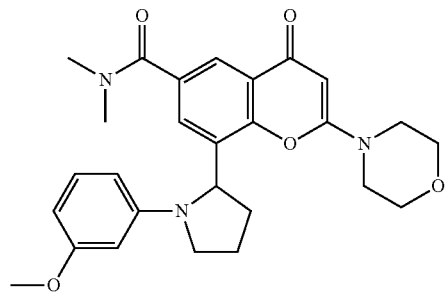 [SMILES: COc1cccc(N2CCCC2c2cc(C(=O)N(C)C)cc3c(=O)cc(N4CCOCC4)oc23)c1]

Title compound was prepared using an analogous procedure to that described in Example 2.00, except that 1-bromo-3-methoxybenzene (0.055 ml, 0.44 mmol) was used in place of 1-bromo-3-fluorobenzene to give 8-(1-(3-methoxyphenyl)pyrrolidin-2-yl)-N,N-dimethyl-2-morpholino-4-oxo-4H-chromene-6-carboxamide (46 mg, 28%) as a solid.

Mass Spectrum: m/z [M+H]+=478.

Proton NMR Spectrum: (DMSO-d6) 1.78-1.90 (m, 1H), 1.94-2.07 (m, 2H), 2.46-2.55 (m partially hidden by DMSO-d5, 1H), 2.70 (s, 3H), 2.90 (s, 3H), 3.33-3.39 (m partially hidden by H2O, 1H), 3.49-3.57 (m, 2H), 3.57-3.63 (m, 2H), 3.64 (s, 3H), 3.69-3.79 (m, 5H), 5.19 (d, 1H), 5.61 (s, 1H), 5.98 (s, 1H), 6.02 (dd, 1H), 6.20 (dd, 1H), 6.98 (dd, 1H), 7.17 (d, 1H), 7.79 (d, 1H)

EXAMPLE 2.02

8-(1-(3-cyano-5-fluorophenyl)pyrrolidin-2-yl)-N,N-dimethyl-2-morpholino-4-oxo-4H-chromene-6-carboxamide

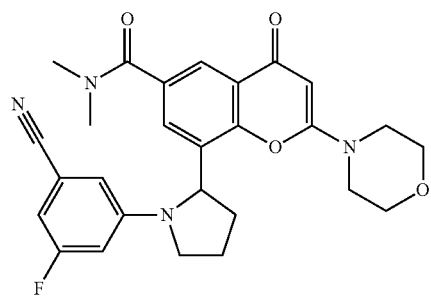 [SMILES: CN(C)C(=O)c1cc(C2CCCN2c2cc(F)cc(C#N)c2)c2oc(N3CCOCC3)cc(=O)c2c1]

Title compound was prepared using an analogous procedure to that described in Example 2.00, except that 3-bromo-5-fluorobenzonitrile (88 mg, 0.44 mmol) was used in place of 1-bromo-3-fluorobenzene to give 8-(1-(3-cyano-5-fluorophenyl)pyrrolidin-2-yl)-N,N-dimethyl-2-morpholino-4-oxo-4H-chromene-6-carboxamide (90 mg, 52%) as a solid.

Mass Spectrum: m/z [M+H]+=491.

Proton NMR Spectrum: (DMSO-d6) 1.74-1.88 (m, 1H), 1.99-2.10 (m, 2H), 2.45-2.56 (m partially hidden by DMSO-d5, 1H), 2.68 (s, 3H), 2.90 (s, 3H), 3.35-3.43 (m partially hidden by H2O, 1H), 3.49-3.58 (m, 2H), 3.58-3.66 (m, 2H), 3.71-3.77 (m, 4H), 3.77-3.85 (m, 1H), 5.31 (d, 1H), 5.62 (s, 1H), 6.61 (d, 1H), 6.75 (s, 1H), 6.92 (s, 1H), 7.07 (d, 1H), 7.80 (d, 1H)

EXAMPLE 2.03

N,N-dimethyl-2-morpholino-4-oxo-8-(1-phenylpyrrolidin-2-yl)-4H-chromene-6-carboxamide

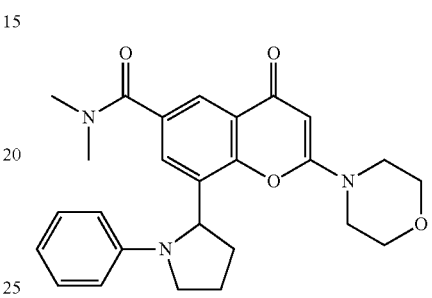

Title compound was prepared using an analogous procedure to that described in Example 2.00, except that bromobenzene (0.046 ml, 0.44 mmol) was used in place of 1-bromo-3-fluorobenzene to give N,N-dimethyl-2-morpholino-4-oxo-8-(1-phenylpyrrolidin-2-yl)-4H-chromene-6-carboxamide (59 mg, 38%) as a solid.

Mass Spectrum: m/z [M+H]+=448.

Proton NMR Spectrum: (DMSO-d6) 1.80-1.93 (m, 1H), 1.95-2.10 (m, 2H), 2.45-2.56 (m partially hidden by DMSO-d5, 1H), 2.67 (s, 3H), 2.89 (s, 3H), 3.33-3.40 (m partially hidden by H2O, 1H), 3.50-3.57 (m, 2H), 3.57-3.65 (m, 2H), 3.70-3.81 (m, 5H), 5.20 (d, 1H), 5.61 (s, 1H), 6.44 (d, 2H), 6.58 (t, 1H), 7.10 (dd, 2H), 7.17 (d, 1H), 7.79 (d, 1H)

EXAMPLE 2.04

8-(1-(4-fluorophenyl)pyrrolidin-2-yl)-N,N-dimethyl-2-morpholino-4-oxo-4H-chromene-6-carboxamide

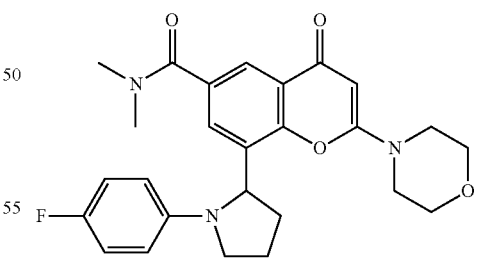

Title compound was prepared using an analogous procedure to that described in Example 2.00, except that 1-bromo-4-fluorobenzene (0.048 ml, 0.44 mmol) was used in place of 1-bromo-3-fluorobenzene to give 8-(1-(4-fluorophenyl)pyrrolidin-2-yl)-N,N-dimethyl-2-morpholino-4-oxo-4H-chromene-6-carboxamide (31 mg, 19%) as a solid.

Mass Spectrum: m/z [M+H]+=466.

Proton NMR Spectrum: (DMSO-d6) 1.79-1.91 (m, 1H), 1.93-2.07 (m, 2H), 2.45-2.56 (m partially hidden by DMSO-d5, 1H), 2.68 (s, 3H), 2.90 (s, 3H), 3.32-3.42 (m partially hidden by H2O, 1H), 3.49-3.57 (m, 2H), 3.57-3.64 (m, 2H), 3.70-3.80 (m, 5H), 5.16 (d, 1H), 5.61 (s, 1H), 6.42 (dd, 2H), 6.94 (dd, 2H), 7.18 (d, 1H), 7.79 (d, 1H)

The racemic 8-(1-(4-fluorophenyl)pyrrolidin-2-yl)-N,N-dimethyl-2-morpholino-4-oxo-4H-chromene-6-carboxamide (200 mg, Example 2.04) was separated by chiral HPLC to afford Examples 2.04a and 2.04b:

|  |  |
|---|---|
| Instrument | Gilson Prep (200 ml heads) |
| Column | Merck 50 mm 20 μm Chiralpak IC |
| Eluent | MeCN/MeOH 80/20 |
| Flow | 100 ml/min |
| Wavelength | 254 nm |
| Sample Conc | 140 mg/25 ml MeCN |
| Injection volume | 25 ml |
| Run Time | 25 mins |

Samples were both obtained as clear thin films, which when triturated with diethylether gave solids. These materials were dried overnight in vacuo at 40° C.

1st eluted enantiomer: 63 mg (99.7% enantiomeric purity) example 2.04a

2nd eluted enantiomer: 58 mg (99.0% enantiomeric purity) example 2.04b

EXAMPLE 2.04a

8-[(2S)-1-(4-fluorophenyl)pyrrolidin-2-yl]-N,N-dimethyl-2-morpholino-4-oxo-4H-chromene-6-carboxamide Mass Spectrum: m/z [M+H]+=466.

Proton NMR Spectrum (CDCl₃): 1.95-2.12 (m, 3H), 2.40-2.52 (m, 1H), 2.78 (s, 3H), 3.03 (s, 3H), 3.30-3.43 (m, 1H), 3.46-3.60 (m, 4H), 3.71-3.80 (m, 1H), 3.81-3.93 (m, 4H), 5.04 (d, 1H), 5.57 (s, 1H), 6.36 (dd, 2H), 6.86 (dd, 2H), 7.40 (d, 1H), 8.11 (d, 1H).

EXAMPLE 2.04b

8-[(2R)-1-(4-fluorophenyl)pyrrolidin-2-yl]-N,N-dimethyl-2-morpholino-4-oxo-4H-chromene-6-carboxamide Mass Spectrum: m/z [M+H]+=466.

Proton NMR Spectrum (CDCl₃): 1.95-2.12 (m, 3H), 2.40-2.52 (m, 1H), 2.78 (s, 3H), 3.03 (s, 3H), 3.30-3.43 (m, 1H), 3.46-3.60 (m, 4H), 3.71-3.80 (m, 1H), 3.81-3.93 (m, 4H), 5.04 (d, 1H), 5.57 (s, 1H), 6.36 (dd, 2H), 6.86 (dd, 2H), 7.40 (d, 1H), 8.11 (d, 1H).

The absolute stereochemistry of each of Examples 2.04a and 2.04b was determined by enantioselective synthesis in the following manner. Example 2.04b was prepared using a chiral starting material of known absolute chemistry (i.e. Methyl 2-morpholino-4-oxo-8-[(2R)-pyrrolidin-2-yl]chromene-6-carboxylate, the preparation of which was described in Example 1.03b). By analogy Example 2.04a was therefore assigned the (S)-configuration. Details for the enantioselective synthesis of Example 2.04b are as follows:

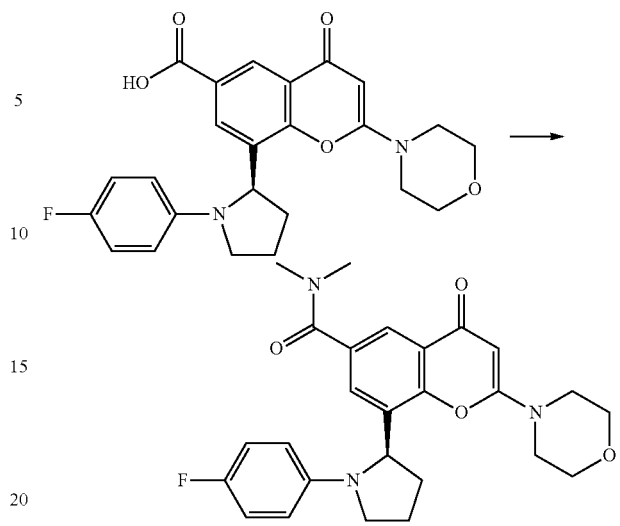

8-[(2R)-(1-(4-fluorophenyl)pyrrolidin-2-yl)]-2-morpholino-4-oxo-4H-chromene-6-carboxylic acid (56 mg, 0.13 mmol, see Example 1.03b for preparation) was reacted with dimethylamine hydrochloride (52 mg, 0.64 mmol) using a procedure similar to the one described in example 1.04 to give 8-(1-(4-fluorophenyl)pyrrolidin-2-yl)-N,N-dimethyl-2-morpholino-4-oxo-4H-chromene-6-carboxamide (9 mg, 15%), analysis data as above.

The 8-[(2R)-(1-(4-fluorophenyl)pyrrolidin-2-yl)]-2-morpholino-4-oxo-4H-chromene-6-carboxylic acid used as starting material was made using procedures similar to the ones described in example 1.05, with 1-bromo-4-fluorobenzene being used in place of 1-bromo-3-fluorobenzene:

Step 1

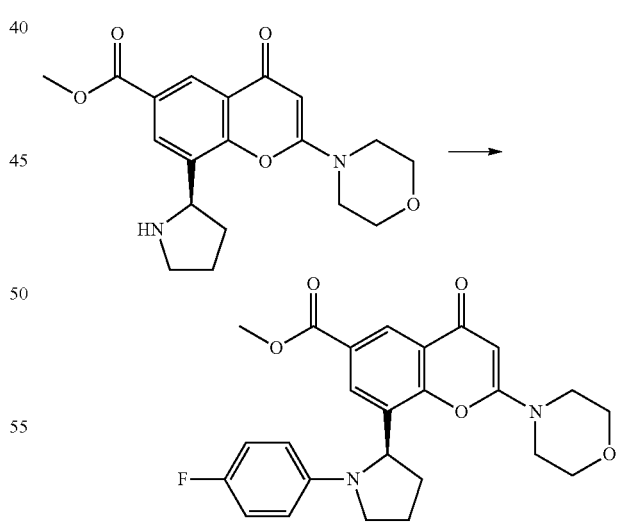

Methyl 2-morpholino-4-oxo-8-[(2R)-pyrrolidin-2-yl]chromene-6-carboxylate (130 mg, 0.36 mmol) was reacted with 1-bromo-4-fluorobenzene (0.239 ml, 2.18 mmol) to afford methyl 8-[(2R)-(1-(4-fluorophenyl)pyrrolidin-2-yl)]-2-morpholino-4-oxo-4H-chromene-6-carboxylate (enantiomer 2, 24 mg, 15%) as a beige solid. Mass Spectrum: m/z [M+H]+=453.

Step 2

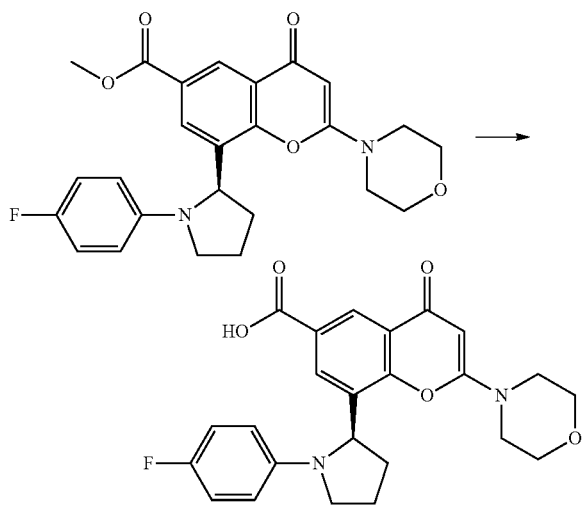

Methyl 8-[(2R)-(1-(4-fluorophenyl)pyrrolidin-2-yl)]-2-morpholino-4-oxo-4H-chromene-6-carboxylate (119 mg, 0.26 mmol from 2 different batches) was reacted with sodium hydroxide to give 8-(1-(4-fluorophenyl)pyrrolidin-2-yl)-2-morpholino-4-oxo-4H-chromene-6-carboxylic acid (enantiomer 2, 95 mg, 82%) as a yellow solid. Mass Spectrum: m/z [M+H]+=439.

EXAMPLE 3.00

8-(1-(3,5-difluorophenyl)pyrrolidin-2-yl)-2-((R)-2-methylmorpholino)-6-(morpholine-4-carbonyl)-4H-chromen-4-one

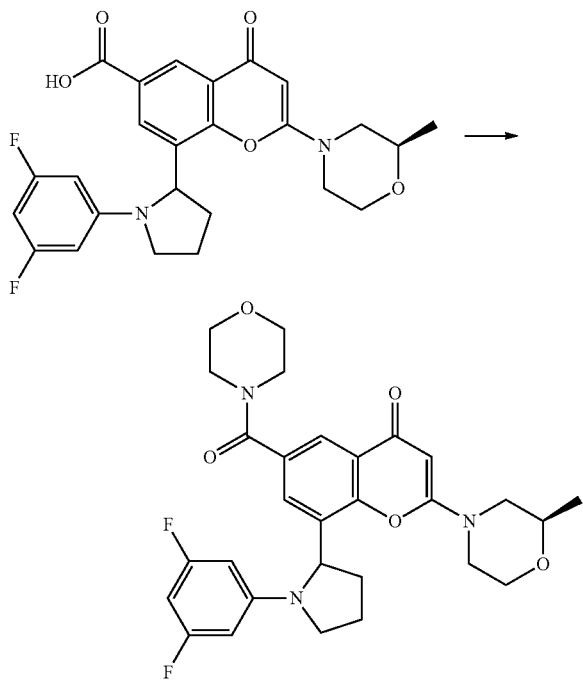

TBTU (154 mg, 0.48 mmol) was added to a stirred solution of 8-(1-(3,5-difluorophenyl)pyrrolidin-2-yl)-2-((R)-2-methylmorpholino)-4-oxo-4H-chromene-6-carboxylic acid (90 mg, 0.19 mmol), DIPEA (0.083 mL, 0.48 mmol) dissolved in DMA (2 mL) under nitrogen. The resulting solution was stirred at room temperature for 30 min. Morpholine (0.050 mL, 0.57 mmol) was added and the mixture was stirred at room temperature for 1 h. The reaction mixture was purified by preparative HPLC. The fractions containing the desired compound were evaporated to dryness to afford 8-(1-(3,5-difluorophenyl)pyrrolidin-2-yl)-2-((R)-2-methylmorpholino)-6-(morpholine-4-carbonyl)-4H-chromen-4-one (68 mg, 66%) as a yellow solid.

Mass Spectrum: m/z [M+H]+=540.

Proton NMR Spectrum: (DMSO-d6) 1.17 (d, 3H), 1.75-1.88 (m, 1H), 1.99-2.08 (m, 2H), 2.45-2.57 (m, partially hidden by DMSO-d6, 1H), 2.77-2.86 (m, 1H), 3.06 (bs, 2H), 3.09-3.19 (m, 1H), 3.23 (bs, 2H), 3.33-3.41 (m partially hidden by H2O, 1H), 3.44 (bs, 2H), 3.55 (bs, 2H), 3.58-3.71 (m, 2H), 3.73-3.80 (m, 1H), 3.85-4.06 (m, 3H), 5.26 (d, 1H), 5.64 (s, 1H), 6.13 (d, 2H), 6.34 (t, 1H), 7.06 (d, 0.5H), 7.07 (d, 0.5H), 7.82 (d, 1H)

The 8-(1-(3,5-difluorophenyl)pyrrolidin-2-yl)-2-((R)-2-methylmorpholino)-4-oxo-4H-chromene-6-carboxylic acid used as starting material was made as follows:—

Step 1

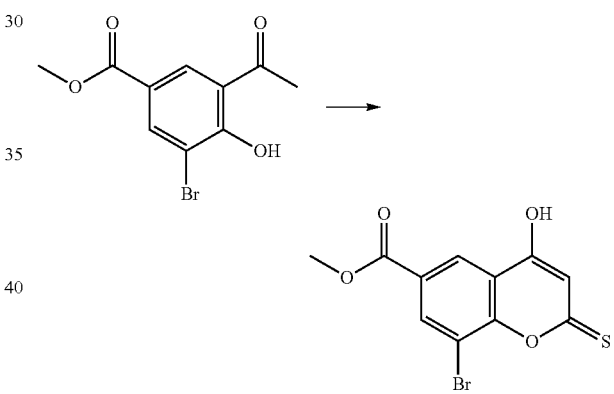

To a suspension of methyl 3-acetyl-5-bromo-4-hydroxybenzoate (70 g, 243.52 mmol) in THF (700 mL) at −50° C. under nitrogen (flask equipped with a bleach trap) was added lithium bis(trimethylsilyl)amide (828 ml, 828 mmol). The dark solution was allowed to warm to −5° C. and stirred for 2 h. Carbon disulfide (22 mL, 365 mmol) was added in one portion to the solution at −20° C. then the mixture was stirred at room temperature overnight. Water (700 mL) was added, the THF layers was washed with water (2×350 mL). The aqueous phases were combined and cooled to 0° C. and quenched with H$_2$SO$_4$ (108 ml, 1948 mmol) in a vessel equipped with a bleach trap to neutralize the H$_2$S formed. The mixture was stirred at room temperature for 3 h, DCM was added (700 mL) and mixture was stirred at room temperature overnight. The aqueous phase was extracted with DCM (2×). The organic phases were combined, washed with brine, dried over MgSO$_4$, filtered and evaporated to afford an orange solid. This solid was triturated in diethyl ether, filtered and dried to give methyl 8-bromo-4-hydroxy-2-thioxo-2H-chromene-6-carboxylate (48.7 g, 63%) as a yellow/orange solid. Mass Spectrum: m/z [M+H]+=317.

Step 2

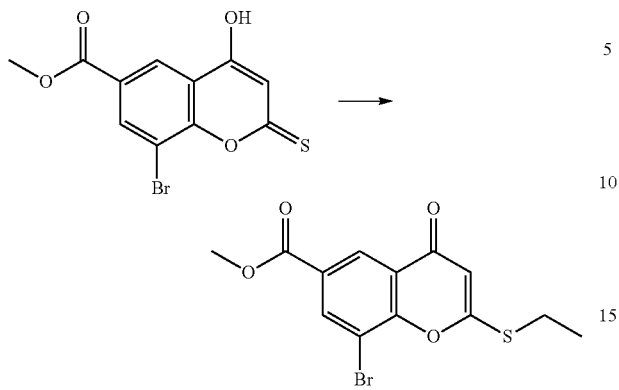

Iodoethane (37.1 mL, 463.51 mmol) was added in one portion to a stirred suspension of methyl 8-bromo-4-hydroxy-2-thioxo-2H-chromene-6-carboxylate (48.69 g, 154.5 mmol) and potassium carbonate (21.35 g, 154.50 mmol) in acetone (490 mL). The resulting suspension was stirred at reflux for 1 h under nitrogen in a flask equipped with a bleach trap. The reaction mixture was concentrated, the residue was diluted with DCM (980 mL)/water (490 mL). The phases were separated and the aqueous layer was extracted with DCM (490 mL). The combined organic phases were washed with brine, dried over MgSO$_4$ and concentrated. The residue was triturated with petroleum ether, filtered and dried under vacuum to give methyl 8-bromo-2-(ethylthio)-4-oxo-4H-chromene-6-carboxylate (52.9 g, 100%) as a pale brown solid. Mass Spectrum: m/z [M+H]+=345

Step 3

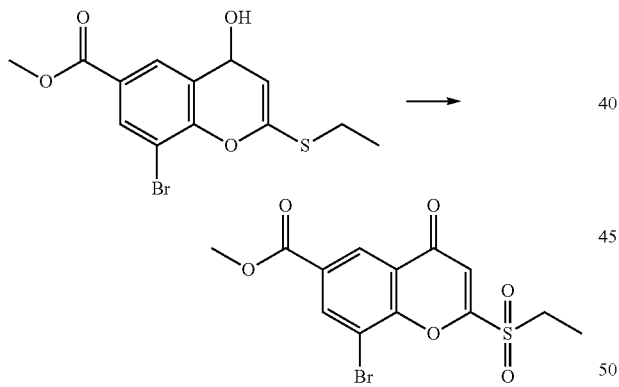

3-chlorobenzoperoxoic acid (76 g, 264.90 mmol) was added portionwise to a stirred solution of methyl 8-bromo-2-(ethylthio)-4-oxo-4H-chromene-6-carboxylate (47.35 g, 132.45 mmol) in DCM (420 mL) cooled with an ice bath. The resulting mixture was then stirred at room temperature for 2 h under nitrogen. The suspension was cooled to −15° C. and filtered, the solid was washed with cold DCM, the filtrate was then washed with a solution of sodium sulfothioate pentahydrate (16.44 g, 66.23 mmol) in water (290 mL), then with saturated solution of NaHCO$_3$ (2×300 mL). The organic layer was decanted, dried over MgSO$_4$ and evaporated to afford a red powder which was triturated with diethyl ether to give solid which was collected by filtration and dried to give methyl 8-bromo-2-(ethylsulfonyl)-4-oxo-4H-chromene-6-carboxylate (44.6 g, 90%) as an off-white material. Mass Spectrum: m/z [M+H]+=375.

Step 4

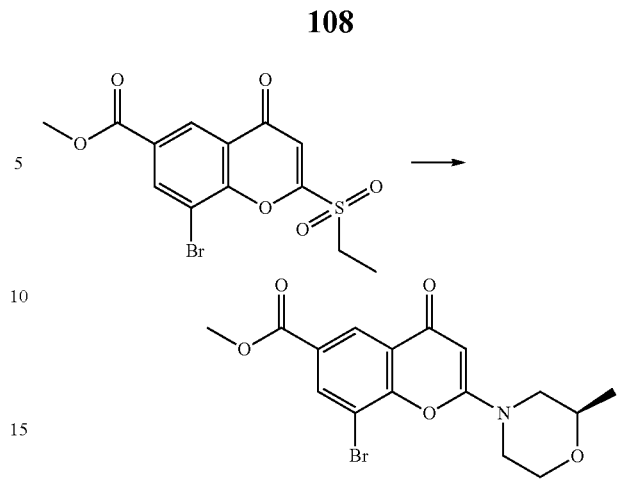

DIPEA (51.7 mL, 296.91 mmol) was added dropwise to a stirred solution of methyl 8-bromo-2-(ethylsulfonyl)-4-oxo-4H-chromene-6-carboxylate (44.56 g, 118.77 mmol) and (R)-2-methylmorpholine hydrochloride (22.88 g, 166.27 mmol) in DCM (430 mL) at 5° C. under nitrogen. The resulting suspension was stirred at room temperature for 1 h. The reaction mixture was diluted with water and quenched slowly with HCl 1M (119 mL, 118.77 mmol) (pH 7). The phases were separated and the organic phase was washed with water, brine, dried over MgSO$_4$ and concentrated. The crude product was triturated in EtAc for 1 h, the solid was collected by filtration and dried to afford methyl 8-bromo-2-((R)-2-methylmorpholino)-4-oxo-4H-chromene-6-carboxylate (32.6 g, 67%) as a white solid. Mass Spectrum: m/z [M+H]+=384.

Step 5

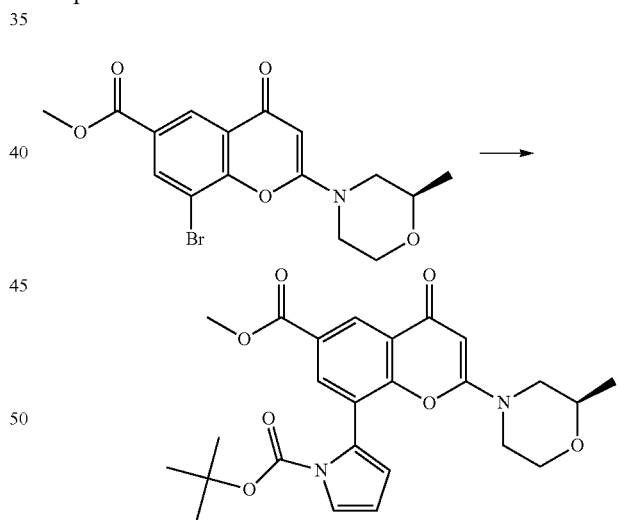

Bis(triphenylphosphine) palladium(II) chloride (0.448 g, 0.63 mmol) was added in one portion to a stirred slurry of (R)-methyl 8-bromo-2-(2-methylmorpholino)-4-oxo-4H-chromene-6-carboxylate (10.06 g, 25 mmol), 1-(tert-butoxycarbonyl)-1H-pyrrol-2-ylboronic acid (6.46 g, 30.00 mmol) and sodium carbonate (7.95 g, 75.00 mmol) in DME (140 mL) and water (28 mL). The mixture was degassed with argon for 15 mins then heated at 80° C. for 6 h. The solvent was evaporated, water was added to the residue and the mixture was extracted with DCM. The combined organic phases were washed with water, brine, dried over MgSO$_4$ and concentrated to give crude (R)-tert-butyl 2-(6-(methoxycarbonyl)-2-

(2-methylmorpholino)-4-oxo-4H-chromen-8-yl)-1H-pyrrole-1-carboxylate containing ~20% of starting material (13.98 g). Mass Spectrum: m/z [M+H]+=469.

Step 6

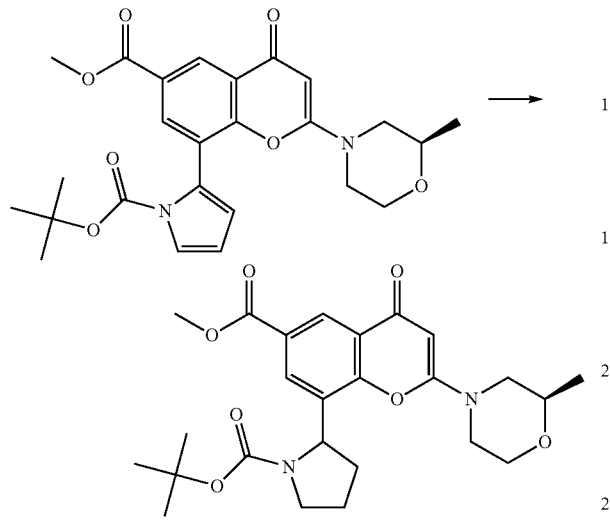

(R)-tert-Butyl 2-(6-(methoxycarbonyl)-2-(2-methylmorpholino)-4-oxo-4H-chromen-8-yl)-1H-pyrrole-1-carboxylate (2 g, 4.27 mmol) and 5% Rhodium on Alumina (50% wet) (0.4 g, 0.09 mmol) in MeOH (50 mL) were stirred under an atmosphere of hydrogen at 5 bar and 65° C. for 2 h. More catalyst was added and stirring continued overnight. 2 g of 5% Rh/C was then added followed by the same amount after 1 h then after another 2 h. The catalyst was filtered through celite and washed with MeOH/DCM and the solvent evaporated. The crude product was purified by flash chromatography on silica gel eluting with 10 to 15% MeOH in EtAc. The solvent was evaporated to dryness to afford tert-butyl 2-(6-(methoxycarbonyl)-2-((R)-2-methylmorpholino)-4-oxo-4H-chromen-8-yl)pyrrolidine-1-carboxylate (1.18 g, 59%) as a white solid. Mass Spectrum: m/z [M+H]+=473.

Step 7

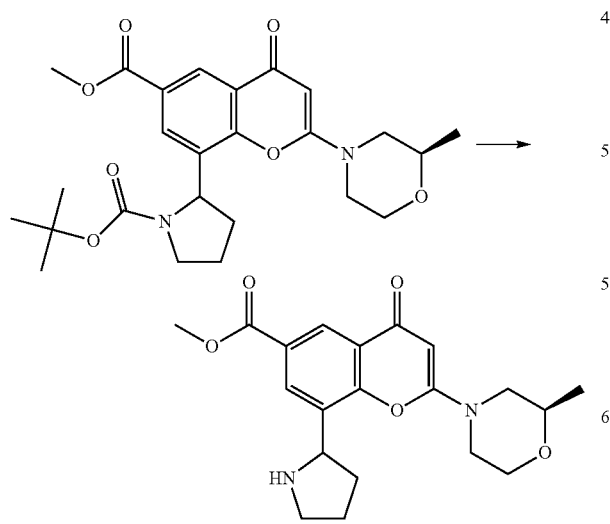

HCl 4N (6.24 mL, 24.97 mmol) was added to a stirred solution of tert-butyl 2-(6-(methoxycarbonyl)-2-((R)-2-methylmorpholino)-4-oxo-4H-chromen-8-yl)pyrrolidine-1-carboxylate (1.18 g, 2.50 mmol) in DCM (10 mL) at room temperature and stirred for 16 h. the solvents were evaporated and DCM (5 mL) and MeOH (5 mL) were added followed by 10% methanolic ammonia (7 N) in dichloromethane (5 mL). The solid was filtered and washed with a 1:1 mixture of DCM and MeOH. The solvent was evaporated to dryness and the crude product was purified by flash chromatography on silica gel eluting with 0 to 10% MeOH in DCM. The solvent was evaporated to dryness, triturated with diethyl ether to give a solid which was collected by filtration and dried under vacuum to give methyl 2-((R)-2-methylmorpholino)-4-oxo-8-(pyrrolidin-2-yl)-4H-chromene-6-carboxylate (0.760 g, 82%) as a white solid. Mass Spectrum: m/z [M+H]=373.

Step 8

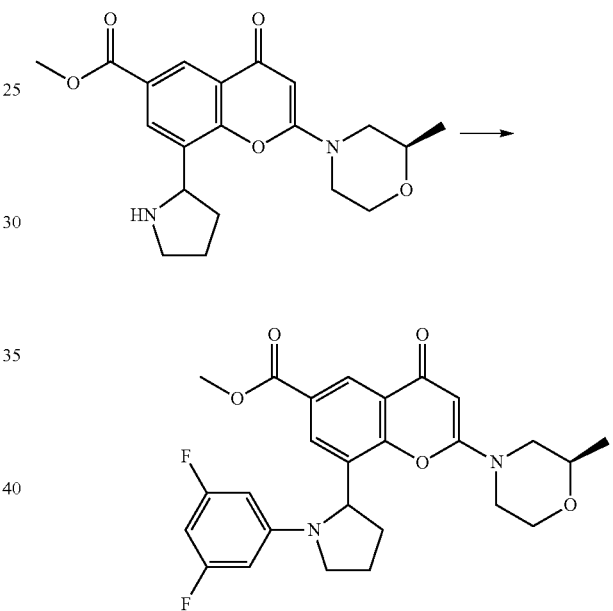

Diacetoxypalladium (4.58 mg, 0.02 mmol) was added to a stirred mixture of methyl 2-((R)-2-methylmorpholino)-4-oxo-8-(pyrrolidin-2-yl)-4H-chromene-6-carboxylate (190 mg, 0.51 mmol), (9,9-dimethyl-9H-xanthene-4,5-diyl)bis(diphenylphosphine) (25.09 mg, 0.04 mmol), 1-bromo-3,5-difluorobenzene (73.4 µl, 0.64 mmol) and cesium carbonate (249 mg, 0.77 mmol) suspended in 1,4-dioxane (5 mL). The resulting suspension was degassed with argon and then stirred at 100° C. for 20 h. The reaction mixture was allowed to cool to room temperature, the insoluble were removed by filtration and the filtrate concentrated. The crude product was adsorbed on silica gel and purified by flash chromatography on silica gel eluting with 0 to 6% MeOH in EtAc. The solvent was evaporated to dryness to afford methyl 8-(1-(3,5-difluorophenyl)pyrrolidin-2-yl)-2-((R)-2-methylmorpholino)-4-oxo-4H-chromene-6-carboxylate (150 mg, 61%) as a beige foam.

Mass Spectrum: m/z [M+H]+=485.

Step 9

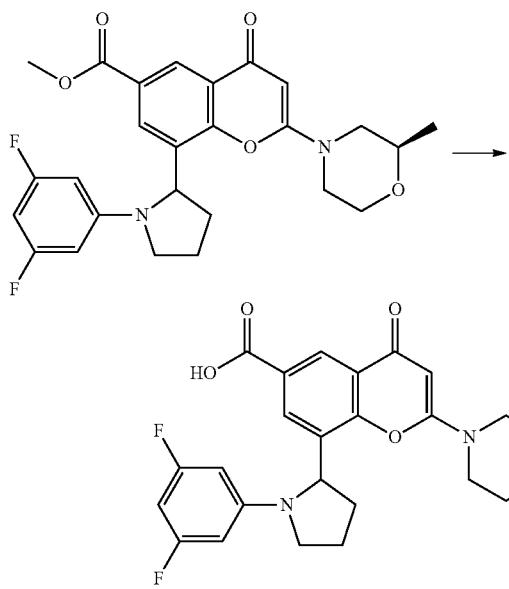

Sodium hydroxide (2N in water) (0.351 mL, 0.70 mmol) was added to a stirred suspension of methyl 2-((R)-2-methylmorpholino)-4-oxo-8-(1-phenylpyrrolidin-2-yl)-4H-chromene-6-carboxylate (136 mg, 0.28 mmol) in MeOH (2 mL)/water (2 mL). The resulting mixture was stirred at room temperature for 18 h then at 50° C. to complete the reaction. The reaction was acidified to pH 2-3 with HCl 2N (0.379 mL, 0.76 mmol) at 5° C. The resulting precipitate was collected by filtration, washed with water and diethyl ether and dried to a constant weight to afford 8-(1-(3,5-difluorophenyl)pyrrolidin-2-yl)-2-((R)-2-methylmorpholino)-4-oxo-4H-chromene-6-carboxylic acid (95 mg, 72%) which was used without further purification. Mass Spectrum: m/z [M+H]+=471.

The (R)-2-methylmorpholine hydrochloride used as starting material in step 4 above was made as follows:—

Step 1

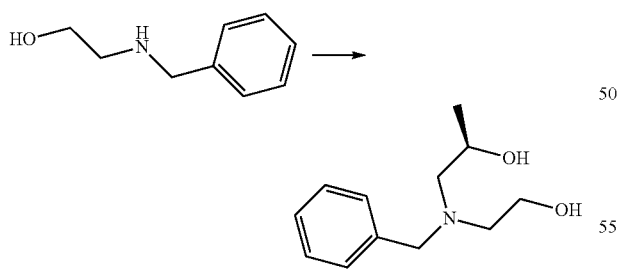

2-(benzylamino)ethanol (207 ml, 1454.97 mmol) and (R)-2-methyloxirane (153 ml, 2182.46 mmol) were mixed together and pumped at a flow rate of 1 mL/min through a 10 mL loop heated at 150° C. in a flow chemistry system. The back pressure regulator was adjusted in order to achieve a pressure inside the loop of 250 psi. Excess of propylene oxide was removed under vacuum to afford (R)-1-(benzyl(2-hydroxyethyl)amino)propan-2-ol (300 g, 99%) as a colourless liquid. Mass Spectrum: m/z [M+H]+=210.

Step 2

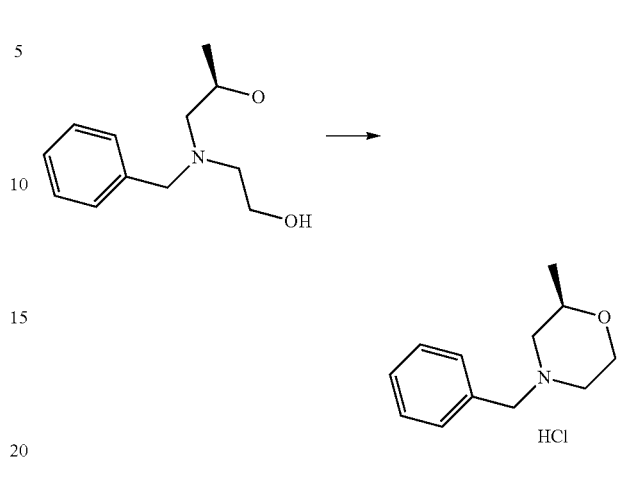

To a stirred solution of (R)-1-(benzyl(2-hydroxyethyl)amino)propan-2-ol (110 g, 525.60 mmol) in dioxane (500 mL) under nitrogen, potassium hydroxide powder (88 g, 1576.80 mmol) and tris(2-(2-methoxyethoxy)ethyl)amine (1.681 mL, 5.26 mmol) were successively added. The mixture was cooled to 0° C. and a solution of 4-methylbenzene-1-sulfonyl chloride (105 g, 551.88 mmol) in dioxane (500 mL) was added dropwise. The reaction mixture was stirred at 0° C. for 45 min then at room temperature for an additional 4 h. The mixture was filtered and filtrate evaporated. The residue was dissolved in DCM and purified on silica, eluting with 25% of EtAc in DCM. The solvents were evaporated to afford an oil which was diluted with EtAc (250 mL). A solution of 4N HCl in dioxane (0.066 L, 262.8 mmol) was then added dropwise under stirring. After 30 min, the formed solid was collected by filtration, washed with diethyl ether and dried to afford (R)-4-benzyl-2-methylmorpholine hydrochloride (40 g, 33%) as a white solid. Proton NMR Spectrum: (DMSO-d6): 1.09 (d, 3H), 2.67-2.77 (m, 1H), 2.93-3.04 (m, 1H), 3.14-3.23 (m, 2H), 3.83-4.00 (m, 3H), 4.29-4.34 (m, 2H), 7.43-7.49 (m, 3H), 7.60-7.68 (m, 2H), 11.62 (bs, 1H).

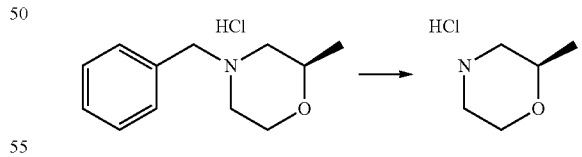

A solution of (R)-4-benzyl-2-methylmorpholine hydrochloride (40 g, 175.65 mmol) in ethanol (1 L) was hydrogenated in the presence of palladium 10%/C (3 g, 28.19 mmol) at room temperature overnight under 1 atm of hydrogen. The mixture was filtered and the filtrate concentrated to dryness to afford (R)-2-methylmorpholine hydrochloride (23 g, 95%) as a white solid. Proton NMR Spectrum: (DMSO-d6): 1.10 (d, 3H), 2.62 (dd, 1H), 2.85-2.95 (m, 1H), 3.08-3.20 (m, 2H), 3.70-3.77 (m, 1H), 3.78-3.83 (m, 1H), 3.90 (dd, 1H), 9.49 (bs, 2H).

EXAMPLE 3.01

2-((R)-2-methylmorpholino)-6-(morpholine-4-carbonyl)-8-(1-phenylpyrrolidin-2-yl)-4H-chromen-4-one

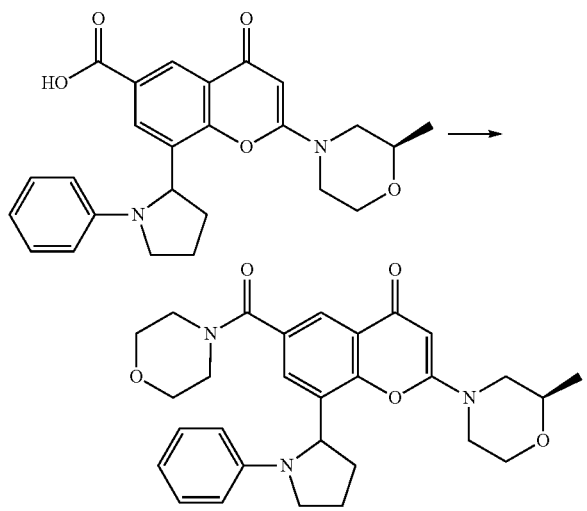

TBTU (148 mg, 0.46 mmol) was added to a stirred solution of 2-((R)-2-methylmorpholino)-4-oxo-8-(1-phenylpyrrolidin-2-yl)-4H-chromene-6-carboxylic acid (80 mg, 0.18 mmol), DIPEA (0.080 mL, 0.46 mmol) dissolved in DMA (2 mL) under nitrogen. The resulting solution was stirred at room temperature for 30 min. Morpholine (0.048 mL, 0.55 mmol) was added to the mixture and stirred at room temperature for 1 h. The reaction mixture was purified by preparative HPLC. The fractions containing the desired compound were evaporated to dryness to afford 2-((R)-2-methylmorpholino)-6-(morpholine-4-carbonyl)-8-(1-phenylpyrrolidin-2-yl)-4H-chromen-4-one (60 mg, 65%) as a gummy solid.

Mass Spectrum: m/z [M+H]+=504.

Proton NMR Spectrum: (DMSO-d6) 1.17 (d, 3H), 1.79-1.93 (m, 1H), 1.98-2.09 (m, 2H), 2.47-2.57 (m, partially hidden by DMSO-d6, 1H), 2.77-2.86 (m, 1H), 3.02 (bs, 2H), 3.09-3.18 (m, 1H), 3.19 (bs, 2H), 3.34-3.40 (m partially hidden by H2O, 1H), 3.42 (bs, 2H), 3.55 (bs, 2H), 3.58-3.71 (m, 2H), 3.72-3.81 (m, 1H), 3.85-4.07 (m, 3H), 5.22 (d, 1H), 5.64 (s, 1H), 6.44 (d, 2H), 6.53 (t, 1H), 7.10 (t, 2H), 7.12 (d, 1H), 7.81 (d, 1H)

The 2-((R)-2-methylmorpholino)-4-oxo-8-(1-phenylpyrrolidin-2-yl)-4H-chromene-6-carboxylic acid used as starting material was made as follows:—

Step 1

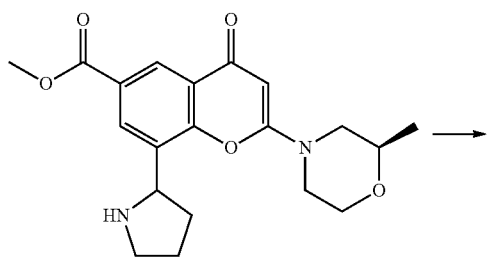

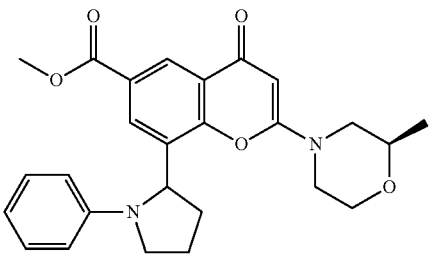

Diacetoxypalladium (4.58 mg, 0.02 mmol) was added to a stirred mixture of methyl 2-((R)-2-methylmorpholino)-4-oxo-8-(pyrrolidin-2-yl)-4H-chromene-6-carboxylate (190 mg, 0.51 mmol), (9,9-dimethyl-9H-xanthene-4,5-diyl)bis(diphenylphosphine) (25.09 mg, 0.04 mmol), bromobenzene (67 μl, 0.64 mmol) and cesium carbonate (249 mg, 0.77 mmol) suspended in 1,4-dioxane (5 mL). The resulting suspension was degassed with argon and stirred at 100° C. for 20 h. Upon cooling to room temperature, the insoluble were removed by filtration and the filtrate concentrated. The crude product was adsorbed on silica gel and purified by flash chromatography on silica gel eluting with 0 to 6% MeOH in EtAc. The solvent was evaporated to dryness to afford methyl 2-((R)-2-methylmorpholino)-4-oxo-8-(1-phenylpyrrolidin-2-yl)-4H-chromene-6-carboxylate (112 mg, 49%) as a beige foam. Mass Spectrum: m/z [M+H]+=449.

Step 2

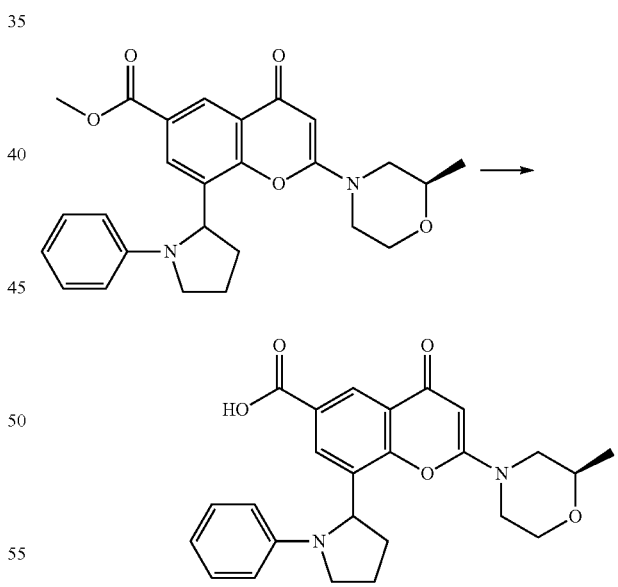

Sodium hydroxide (2N in water) (0.293 mL, 0.59 mmol) was added to a stirred suspension of methyl 2-((R)-2-methylmorpholino)-4-oxo-8-(1-phenylpyrrolidin-2-yl)-4H-chromene-6-carboxylate (105 mg, 0.23 mmol) in MeOH (2 mL)/water (2 mL) as described in example 3.00 to afford 2-((R)-2-methylmorpholino)-4-oxo-8-(1-phenylpyrrolidin-2-yl)-4H-chromene-6-carboxylic acid (87 mg, 86%) which was used without further purification. Mass Spectrum: m/z [M+H]+=435.

EXAMPLE 3.02

8-(1-(3-fluorophenyl)pyrrolidin-2-yl)-2-((R)-2-methylmorpholino)-6-(morpholine-4-carbonyl)-4H-chromen-4-one

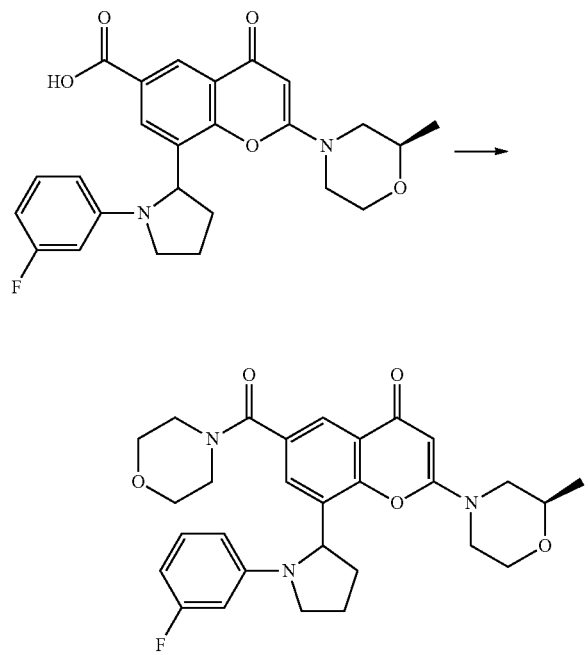 [SMILES: C[C@@H]1CN(c2cc(=O)c3cc(C(=O)O)cc(C4CCCN4c4cccc(F)c4)c3o2)CCO1 ; C[C@@H]1CN(c2cc(=O)c3cc(C(=O)N4CCOCC4)cc(C4CCCN4c4cccc(F)c4)c3o2)CCO1]

TBTU (138 mg, 0.43 mmol) was added to a stirred solution of 8-(1-(3-fluorophenyl)pyrrolidin-2-yl)-2-((R)-2-methylmorpholino)-4-oxo-4H-chromene-6-carboxylic acid (97 mg, 0.21 mmol), DIPEA (0.075 mL, 0.43 mmol) dissolved in DMF (1.5 mL) under nitrogen. The resulting solution was stirred at room temperature for 1.5 h. Morpholine (0.028 mL, 0.32 mmol) was added and the reaction mixture was stirred at room temperature for 1 h. The reaction mixture was purified by preparative HPLC. The fractions were evaporated to dryness, the residue was dissolved in DCM, dried over MgSO$_4$ and evaporated to dryness to afford 8-(1-(3-fluorophenyl)pyrrolidin-2-yl)-2-((R)-2-methylmorpholino)-6-(morpholine-4-carbonyl)-4H-chromen-4-one (63 mg, 56%) as a yellow foam.

Mass Spectrum: m/z [M+H]+=533.

Proton NMR Spectrum: (DMSO-d6) 1.17 (d, 3H), 1.77-1.90 (m, 1H), 1.98-2.10 (m, 2H), 2.47-2.57 (m, partially hidden by DMSO-d6, 1H), 2.78-2.86 (m, 1H), 3.04 (bs, 2H), 3.09-3.18 (m, 1H), 3.22 (bs, 2H), 3.34-3.41 (m partially hidden by H2O, 1H), 3.42 (bs, 2H), 3.54 (bs, 2H), 3.58-3.70 (m, 2H), 3.73-3.80 (m, 1H), 3.85-4.06 (m, 3H), 5.25 (d, 1H), 5.63 (s, 0.5H), 3.64 (s, 0.5H), 6.19-6.29 (m, 2H), 6.38 (ddd, 1H), 7.05-7.13 (m, 2H), 7.81 (d, 1H).

The 8-(1-(3-fluorophenyl)pyrrolidin-2-yl)-2-((R)-2-methylmorpholino)-4-oxo-4H-chromene-6-carboxylic acid used as starting material was made as follows:—

Step 1

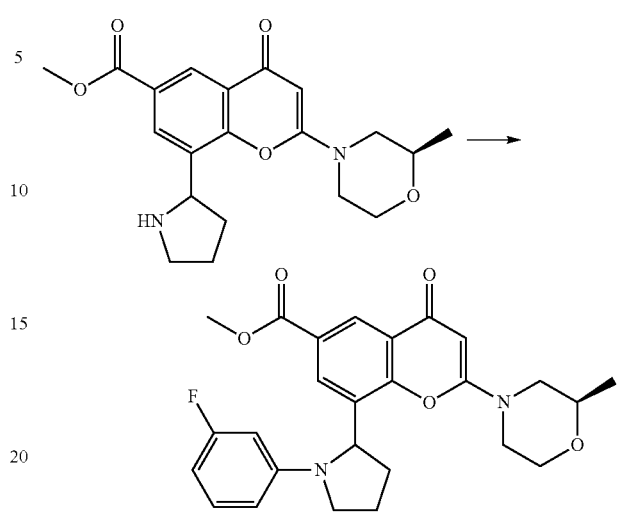

Diacetoxypalladium (8.44 mg, 0.04 mmol) was added to a stirred mixture of methyl 2-((R)-2-methylmorpholino)-4-oxo-8-(pyrrolidin-2-yl)-4H-chromene-6-carboxylate (0.35 g, 0.94 mmol), (9,9-dimethyl-9H-xanthene-4,5-diyl)bis(diphenylphosphine) (0.046 g, 0.08 mmol), 1-bromo-3-fluorobenzene (0.131 ml, 1.17 mmol) and cesium carbonate (0.459 g, 1.41 mmol) suspended in 1,4-dioxane (9 mL). The resulting suspension was degassed with argon and then stirred at 100° C. for 20 h. The reaction mixture was allowed to cool to room temperature, the insoluble were removed by filtration and the filtrate concentrated. The crude product was adsorbed on silica gel and purified by flash chromatography on silica gel eluting with 0 to 10% MeOH in EtAc. The solvents were evaporated to dryness to afford methyl 8-(1-(3-fluorophenyl)pyrrolidin-2-yl)-2-((R)-2-methylmorpholino)-4-oxo-4H-chromene-6-carboxylate (0.279 g, 64%) as a beige foam. Mass Spectrum: m/z [M+H]+=467.

Step 2

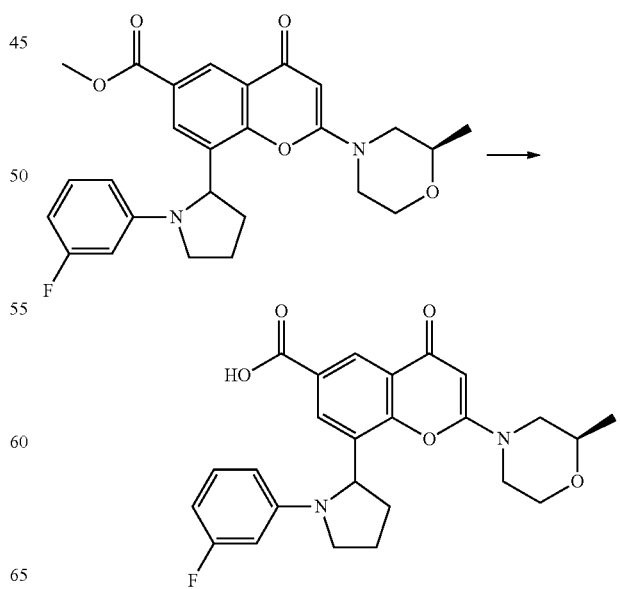

An aqueous NaOH 2N (0.804 ml, 1.61 mmol) solution was added to methyl 8-(1-(3-fluorophenyl)pyrrolidin-2-yl)-2-((R)-2-methylmorpholino)-4-oxo-4H-chromene-6-carboxylate (0.25 g, 0.54 mmol) suspended in MeOH (4 mL). The solution was stirred at 40° C. overnight then cooled to 0° C. and an aqueous HCl 2N (0.670 ml, 1.34 mmol) solution was added dropwise to the reaction mixture until pH ~3. The resulting precipitate was collected by filtration, washed with water and dried under vacuum at 50° C. in presence of $P_2O_5$ to a constant weight to afford 8-(1-(3-fluorophenyl)pyrrolidin-2-yl)-2-((R)-2-methylmorpholino)-4-oxo-4H-chromene-6-carboxylic acid (201 mg, 83%) as a beige solid.

Mass Spectrum: m/z [M+H]+=453.

EXAMPLE 3.03

8-(1-(3-fluorophenyl)pyrrolidin-2-yl)-N,N-dimethyl-2-((R)-2-methylmorpholino)-4-oxo-4H-chromene-6-carboxamide

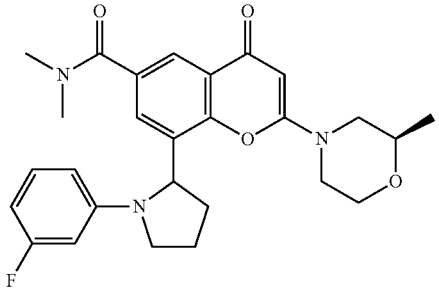 [SMILES: C[C@@H]1CN(c2cc(=O)c3cc(C(=O)N(C)C)cc(C4CCCN4c4cccc(F)c4)c3o2)CCO1]

8-(1-(3-fluorophenyl)pyrrolidin-2-yl)-2-((R)-2-methylmorpholino)-4-oxo-4H-chromene-6-carboxylic acid (102 mg, 0.23 mmol) was reacted with dimethylamine (2N in THF) (0.169 ml, 0.34 mmol) as described in Example 3.02 to give 8-(1-(3-fluorophenyl)pyrrolidin-2-yl)-N,N-dimethyl-2-((R)-2-methylmorpholino)-4-oxo-4H-chromene-6-carboxamide (51 mg, 47%) as a pale yellow foam.

Mass Spectrum: m/z [M+H]+=480.

Proton NMR Spectrum: (DMSO-d6) 1.17 (d, 3H), 1.77-1.90 (m, 1H), 1.98-2.08 (m, 2H), 2.45-2.58 (m, partially hidden by DMSO-d6, 1H), 2.69 (s, 3H), 2.78-2.86 (m, 1H), 2.90 (s, 3H), 3.09-3.18 (m, 1H), 3.33-3.39 (m partially hidden by H2O, 1H), 3.58-3.70 (m, 2H), 3.72-7.79 (m, 1H), 3.85-4.07 (m, 3H), 6.24 (d, 1H), 5.63 (s, 0.5H), 5.64 (s, 0.5H), 6.21-6.29 (m, 2H), 6.33-6.40 (m, 1H), 7.04 (ddd, 1H), 7.13 (d, 0.5H), 7.14 (d, 0.5H), 7.80 (d, 1H).

The invention claimed is:

1. A compound of the Formula I:

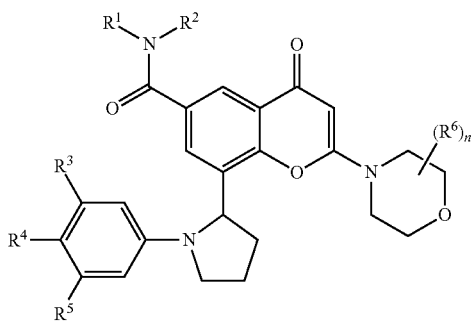

in which:
R$^1$ is (1-4C)alkyl optionally substituted by hydroxy;
R$^2$ is H or (1-4C)alkyl; or
R$^1$ and R$^2$ together form a 3 to 8 membered nitrogen containing heterocyclyl ring system, which optionally contains 1 or 2 further heteroatoms selected from oxygen, nitrogen and sulphur, wherein a ring sulphur atom is optionally oxidised to form the S-oxide(s), said ring being optionally substituted by hydroxy;
R$^3$ and R$^5$ are independently selected from H, halogeno, (1-3C)alkoxy and cyano;
R$^4$ is H or fluoro;
n is 0 or 1, and when n is 1, the R$^6$ group is methyl; or a pharmaceutically-acceptable salt thereof.

2. A compound of the Formula I according to claim 1, wherein:
R$^1$ is (1-4C)alkyl optionally substituted by hydroxy;
R$^2$ is (1-4C)alkyl; or
R$^1$ and R$^2$ together form a 4 to 6 membered nitrogen containing heterocyclyl ring system, which optionally contains 1 further heteroatom selected from oxygen, nitrogen and sulphur, wherein a ring sulphur atom is optionally oxidised to form the S-oxide(s), said ring being optionally substituted by hydroxy; or a pharmaceutically-acceptable salt thereof.

3. A compound of the Formula I according to claim 1, wherein R$^3$ and R$^5$ are independently selected from H, fluoro, methoxy and cyano; or a pharmaceutically-acceptable salt thereof.

4. A compound of the Formula I according to claim 1, wherein R$^4$ is H; or a pharmaceutically-acceptable salt thereof.

5. A compound of the Formula I according to claim 1, wherein n is 0; or a pharmaceutically-acceptable salt thereof.

6. A compound of the Formula I according to claim 1, wherein n is 1 and R$^6$ is methyl; or a pharmaceutically-acceptable salt thereof.

7. A compound of the Formula I according to claim 1, wherein:
R$^1$ is (1-4C)alkyl optionally substituted by hydroxy;
R$^2$ is (1-4C)alkyl; or
R$^1$ and R$^2$ together form a 4 to 6 membered nitrogen containing heterocyclyl ring system, which optionally contains 1 further heteroatom selected from oxygen, nitrogen and sulphur, wherein a ring sulphur atom is optionally oxidised to form the S-oxide(s), said ring being optionally substituted by hydroxy;
R$^3$ and R$^5$ are independently selected from H or halogeno and R$^4$ is H;
n is 0 or 1, and when n is 1, the R$^6$ group is methyl; or a pharmaceutically-acceptable salt thereof.

8. A compound of the Formula I according to claim 1 wherein:
R$^1$ is methyl, ethyl or 2-hydroxyethyl;
R$^2$ is methyl or ethyl; or
R$^1$ and R$^2$ together form a nitrogen containing heterocyclyl ring system; selected from azetidinyl, morpholinyl, 1-oxotetrahydro-1,4-thiazinyl and piperidinyl, said ring being optionally substituted by hydroxy;
R$^3$ and R$^5$ are independently selected from H or halogeno and R$^4$ is H;
n is 0 or 1, and when n is 1, the R$^6$ group is methyl; or a pharmaceutically-acceptable salt thereof.

9. A compound of the Formula I according to claim 1 wherein:
R$^1$ is methyl or 2-hydroxyethyl;
R$^2$ is methyl; or R¹ and R² together form a nitrogen containing heterocyclyl ring system, selected from azetidin-1-yl, morpholin-4-yl, 1-oxotetrahydro-1,4-thiazin-4-yl, piperidin-1-yl and 4-hydroxypiperidin-1-yl;

R³ and R⁵ are independently selected from H, fluoro, methoxy and cyano;

R⁴ is H or fluoro;

n is 0 or 1, and when n is 1, the R⁶ group is methyl; or a pharmaceutically-acceptable salt thereof.

10. A compound of the Formula I according to claim 1 selected from any one of the following:—

8-(1-(3,5-difluorophenyl)pyrrolidin-2-yl)-N,N-dimethyl-2-morpholino-4-oxo-4H-chromene-6-carboxamide;

8-(1-(3,5-difluorophenyl)pyrrolidin-2-yl)-6-(morpholine-4-carbonyl)-2-morpholino-4H-chromen-4-one;

8-[(2S)-1-(3,5-difluorophenyl)pyrrolidin-2-yl]-6-(morpholine-4-carbonyl)-2-morpholino-chromen-4-one;

8-[(2R)-1-(3,5-difluorophenyl)pyrrolidin-2-yl]-6-(morpholine-4-carbonyl)-2-morpholino-chromen-4-one;

6-(azetidine-1-carbonyl)-8-(1-(3,5-difluorophenyl)pyrrolidin-2-yl)-2-morpholino-4H-chromen-4-one;

6-(azetidine-1-carbonyl)-8-[(2S)-1-(3,5-difluorophenyl)pyrrolidin-2-yl]-2-morpholino-chromen-4-one;

6-(azetidine-1-carbonyl)-8-[(2R)-1-(3,5-difluorophenyl)pyrrolidin-2-yl]-2-morpholino-chromen-4-one;

8-(1-(3-fluorophenyl)pyrrolidin-2-yl)-N,N-dimethyl-2-morpholino-4-oxo-4H-chromene-6-carboxamide;

8-[(2S)-1-(3-fluorophenyl)pyrrolidin-2-yl]-N,N-dimethyl-2-morpholino-4-oxo-chromene-6-carboxamide;

8-[(2R)-1-(3-fluorophenyl)pyrrolidin-2-yl]-N,N-dimethyl-2-morpholino-4-oxo-chromene-6-carboxamide;

8-(1-(3-fluorophenyl)pyrrolidin-2-yl)-6-(morpholine-4-carbonyl)-2-morpholino-4H-chromen-4-one;

8-[(2S)-1-(3-fluorophenyl)pyrrolidin-2-yl]-6-(morpholine-4-carbonyl)-2-morpholino-chromen-4-one;

8-[(2R)-1-(3-fluorophenyl)pyrrolidin-2-yl]-6-(morpholine-4-carbonyl)-2-morpholino-chromen-4-one;

6-(azetidine-1-carbonyl)-8-(1-(3-fluorophenyl)pyrrolidin-2-yl)-2-morpholino-4H-chromen-4-one;

6-(azetidine-1-carbonyl)-8-[(2S)-1-(3-fluorophenyl)pyrrolidin-2-yl]-2-morpholino-chromen-4-one;

6-(azetidine-1-carbonyl)-8-[(2R)-1-(3-fluorophenyl)pyrrolidin-2-yl]-2-morpholino-chromen-4-one;

8-(1-(3-fluorophenyl)pyrrolidin-2-yl)-N,N-dimethyl-2-morpholino-4-oxo-4H-chromene-6-carboxamide;

8-(1-(3,5-difluorophenyl)pyrrolidin-2-yl)-2-((R)-2-methylmorpholino)-6-(morpholine-4-carbonyl)-4H-chromen-4-one;

8-(1-(3-fluorophenyl)pyrrolidin-2-yl)-2-((R)-2-methylmorpholino)-6-(morpholine-4-carbonyl)-4H-chromen-4-one; and 8-(1-(3-fluorophenyl)pyrrolidin-2-yl)-N,N-dimethyl-2-((R)-2-methylmorpholino)-4-oxo-4H-chromene-6-carboxamide; or a pharmaceutically-acceptable salt thereof.

11. A compound of the Formula I according to claim 1 which is 8-[(2R)-1-(3,5-difluorophenyl)pyrrolidin-2-yl]-6-(morpholine-4-carbonyl)-2-morpholino-chromen-4-one; or a pharmaceutically-acceptable salt thereof.

12. A compound of the Formula I according to claim 1 which is 8-[(2R)-1-(3,5-difluorophenyl)pyrrolidin-2-yl]-6-(morpholine-4-carbonyl)-2-morpholino-chromen-4-one.

13. A pharmaceutically-acceptable salt of a compound of the Formula I according to claim 1 which is 8-[(2R)-1-(3,5-difluorophenyl)pyrrolidin-2-yl]-6-(morpholine-4-carbonyl)-2-morpholino-chromen-4-one.

14. A compound of the Formula I according to claim 1 which is 8-[(2S)-1-(3,5-difluorophenyl)pyrrolidin-2-yl]-6-(morpholine-4-carbonyl)-2-morpholino-chromen-4-one; or a pharmaceutically-acceptable salt thereof.

15. A compound of the Formula I according to claim 1 which is 8-(1-(3,5-difluorophenyl)pyrrolidin-2-yl)-2-((R)-2-methylmorpholino)-6-(morpholine-4-carbonyl)-4H-chromen-4-one; or a pharmaceutically-acceptable salt thereof.

16. A pharmaceutical composition, which comprises a compound of the Formula I; or a pharmaceutically-acceptable salt thereof, according to claim 1 in association with a pharmaceutically-acceptable diluent or carrier.

17. A method for the treatment of tumours which are sensitive to inhibition of PI 3-kinase enzymes in a warm-blooded animal having such tumours, which comprises administering to said animal an effective amount of a compound of the Formula I, or a pharmaceutically-acceptable salt thereof, according to claim 1.

* * * * *